(12) United States Patent
Liu

(10) Patent No.: US 10,407,506 B2
(45) Date of Patent: Sep. 10, 2019

(54) ANTI-MCAM ANTIBODIES AND ASSOCIATED METHODS OF USE

(71) Applicant: PROTHENA BIOSCIENCES LIMITED, Dublin (IE)

(72) Inventor: Yue Liu, Foster City, CA (US)

(73) Assignee: PROTHENA BIOSCIENCES LIMITED, Dublin (IE)

( * ) Notice: Subject to any disclaimer, the term of this patent is extended or adjusted under 35 U.S.C. 154(b) by 0 days.

(21) Appl. No.: 15/125,570

(22) PCT Filed: Mar. 12, 2015

(86) PCT No.: PCT/IB2015/051786
§ 371 (c)(1),
(2) Date: Sep. 12, 2016

(87) PCT Pub. No.: WO2015/136469
PCT Pub. Date: Sep. 17, 2015

(65) Prior Publication Data
US 2017/0002089 A1    Jan. 5, 2017

Related U.S. Application Data

(60) Provisional application No. 61/952,123, filed on Mar. 12, 2014, provisional application No. 62/023,698, filed on Jul. 11, 2014, provisional application No. 62/068,438, filed on Oct. 24, 2014.

(51) Int. Cl.
| | | |
|---|---|---|
| C07K 16/00 | (2006.01) | |
| C07K 16/30 | (2006.01) | |
| C12P 21/00 | (2006.01) | |
| G01N 33/577 | (2006.01) | |
| G01N 33/68 | (2006.01) | |

(52) U.S. Cl.
CPC ........ C07K 16/3092 (2013.01); C12P 21/005 (2013.01); G01N 33/577 (2013.01); G01N 33/6854 (2013.01); *C07K 2317/24* (2013.01); *C07K 2317/34* (2013.01); *C07K 2317/56* (2013.01); *C07K 2317/565* (2013.01); *C07K 2317/567* (2013.01); *C07K 2317/76* (2013.01); *C07K 2317/92* (2013.01); *C07K 2319/30* (2013.01); *C07K 2319/32* (2013.01)

(58) Field of Classification Search
None
See application file for complete search history.

(56) References Cited

U.S. PATENT DOCUMENTS

| | | | | |
|---|---|---|---|---|
| 5,859,205 A * | 1/1999 | Adair | ...................... | C07K 16/18 530/387.1 |
| 7,090,844 B2 | 8/2006 | Bar-Eli et al. | | |
| 7,456,260 B2 * | 11/2008 | Rybak | ................ | C07K 16/2803 530/387.3 |
| 7,815,909 B2 | 10/2010 | Heavner et al. | | |
| 7,915,225 B2 | 3/2011 | Finck | | |
| 8,293,468 B2 | 10/2012 | Prat et al. | | |
| 9,017,682 B2 | 4/2015 | Prat et al. | | |
| 9,447,190 B2 | 9/2016 | Flanagan et al. | | |
| 10,059,761 B2 | 8/2018 | Tam et al. | | |
| 2003/0068319 A1 | 4/2003 | Bar Eli | | |
| 2003/0147809 A1 | 8/2003 | Gudas | | |
| 2004/0053850 A1 | 3/2004 | Krissansen et al. | | |
| 2005/0069541 A1 | 3/2005 | Karlik et al. | | |
| 2006/0088523 A1 * | 4/2006 | Andya et al. | ...... | C07K 16/2896 424/172.1 |
| 2006/0246077 A1 * | 11/2006 | Bar-Eli | .............. | A61K 51/1066 424/155.1 |
| 2008/0103107 A1 * | 5/2008 | Ward | ..................... | C12Q 1/485 514/44 A |
| 2011/0014183 A1 | 1/2011 | Prat et al. | | |
| 2011/0217237 A1 | 8/2011 | Chen et al. | | |
| 2013/0216556 A1 | 8/2013 | Fowler et al. | | |
| 2014/0314744 A1 | 10/2014 | Flanagan et al. | | |
| 2015/0218266 A1 | 8/2015 | Prat et al. | | |
| 2015/0239980 A1 | 8/2015 | Flanagan et al. | | |
| 2015/0259408 A1 | 9/2015 | Tam et al. | | |
| 2015/0259419 A1 | 9/2015 | Liu et al. | | |
| 2017/0002077 A1 | 1/2017 | Tam et al. | | |
| 2017/0037144 A1 | 2/2017 | Flanagan et al. | | |
| 2017/0101470 A1 | 4/2017 | Liu et al. | | |
| 2017/0129954 A1 | 5/2017 | Flanagan et al. | | |

(Continued)

FOREIGN PATENT DOCUMENTS

| | | |
|---|---|---|
| EP | 0 990 663 A2 | 4/2000 |
| EP | 2234600 A1 | 8/2014 |
| WO | WO 2009/054435 A1 | 4/2000 |
| WO | WO 2003/057006 A2 | 12/2002 |
| WO | WO 2003/057837 A1 | 7/2003 |
| WO | WO 2003/057838 A2 | 7/2003 |
| WO | WO 2007/058725 A2 | 5/2007 |
| WO | WO 2009/028663 A1 | 3/2009 |

(Continued)

OTHER PUBLICATIONS

Vajdos et al. Comprehensive functional maps of the antigen-binding site of an anti-ErbB2 antibody obtained with shotgun scanning mutagenesis. J. Mol. Biol. Jul. 5, 2002, 320(2):415-28. (Year: 2002).*

(Continued)

Primary Examiner — Maher M Haddad
(74) Attorney, Agent, or Firm — Alston & Bird LLP

(57) ABSTRACT

The invention provides anti-MCAM antibodies that inhibit the ability of human MCAM to bind a laminin alpha-4 chain. The invention also provides pharmaceutical compositions, methods of generating such antibodies, and their use in the manufacture of medicaments for treatment of neuroinflammatory disease, autoimmune disease, or cancer.

20 Claims, 3 Drawing Sheets
Specification includes a Sequence Listing.

(56) References Cited

U.S. PATENT DOCUMENTS

| | | |
|---|---|---|
| 2017/0145109 A1 | 5/2017 | Flanagan et al. |
| 2017/0158755 A1 | 6/2017 | Flanagan et al. |
| 2018/0105602 A1 | 4/2018 | Flanagan et al. |
| 2018/0208646 A1 | 7/2018 | Tam et al. |
| 2018/0371067 A1 | 12/2018 | Tam et al. |

FOREIGN PATENT DOCUMENTS

| | | | |
|---|---|---|---|
| WO | WO 2009/064854 A2 | 5/2009 | |
| WO | WO 2009/093138 A1 | 7/2009 | |
| WO | WO 2011/100477 A2 | 8/2011 | |
| WO | WO 2012/170071 A1 | 12/2012 | |
| WO | WO 2012/170071 A2 | 12/2012 | |
| WO | WO 2013/164789 A1 | 11/2013 | |
| WO | WO 2013/186700 A1 | 12/2013 | |
| WO | WO 2014/039975 A2 | 3/2014 | |
| WO | WO 2014/039975 A3 | 3/2014 | |
| WO | WO 2015/061584 A1 | 4/2015 | |
| WO | WO 2015/136468 A1 | 9/2015 | |
| WO | WO 2015/136469 A1 | 9/2015 | |
| WO | WO 2015/136472 A1 | 9/2015 | |
| WO | WO 2015/136570 A1 | 9/2015 | |
| WO | WO 2012/024187 A1 | 3/2017 | |
| WO | WO 2017/046774 A2 | 3/2017 | |
| WO | WO 2017/046776 A2 | 3/2017 | |
| WO | WO 2017/149513 A1 | 9/2017 | |
| WO | WO 2017/208210 A1 | 12/2017 | |
| WO | WO 2018/223140 A1 | 12/2018 | |

OTHER PUBLICATIONS

U.S. Appl. No. 15/222,849 Requirement for Restriction/Election dated Nov. 16, 2017.
U.S. Appl. No. 15/222,848 Requirement for Restriction/Election dated Nov. 16, 2017.
U.S. Appl. No. 14/656,619 Notice of Allowance dated Nov. 2, 2017.
U.S. Appl. No. 15/268,178 Requirement for Restriction/Election dated Dec. 7, 2017.
Awad, et al., "Cyclophosphamide in multiple sclerosis scientific rationale, history and novel treatment paradigms," *Ther Adv Neurol Disord*, 2(16) 357-368 (2009).
U.S. Appl. No. 14/124,620 Non/Final Office Action dated Jan. 19, 2018.
Archelos, et al., "Inhibition of Experimental Autoimmune Encephalomyelitis by an Antibody to the Intercellular Adhesion Molecule ICAM-1," Ann Neurol, 34:145-154 (1993).
Bardin, et al., "Identification of the S-Endo 1 endothelial-associated antigen," *Biochem Biophys Res Commun.*, 5;218(1):210-216, (Jan. 1996).
Bar-Eli, "Molecular mechanisms of melanoma metastasis," *J Cell Physiol*, 173(2):275-278, (Nov. 1997).
Bar-Eli, "Role of AP-2 in tumor growth and metastasis of human melanoma." *Cancer Metastasis Rev*,18(3):377-385, (1999).
Beutel, et al., "Possible Implications of MCAM Expression in Metastasis and Non-Metastatic of Primary Uveal Melanoma Patients," *Current Eve Research*, 34(11, 1004-1009, (2009).
Brucklacher-Waldert, et al., "Phenotypical and functional characterization of T helper 17 cells in multiple sclerosis," *Brain*, 132:3329-3341 (2009).
Bu, et al., "Anti-CD146 monoclonal antibody AA98 inhibits angiogenesis via suppression of nuclear factor-κB activation", *Mol Cancer Ther.*, 5(11)2872-2878 (Nov. 2006).
Chen, et al., "Is CD146 pivotal in neoplasm invasion and blastocyst embedding?" *Med Hypotheses*, 76(3):378-381, (Mar. 2001).
Dagur et al., "MCAM-expressing CD4(+) T cells in Peripheral Blood Secrete IL-17A and are Significantly Elevated in Inflammatory Autoimmune Diseases," *J Autoimmun*, 37(4):319-27 (Dec. 2011).
Dehahn, et al., "The α4 laminin subunit regulates endothelial cell survival", Experimental Cell Research, 294:281-289, (2004).

Denton, et al., "A study of adhesion molecules as markers of progression in malignant melanoma," *J Pathol*, 167(2):187-191, (Jun. 1992).
Despoix, et al., "Mouse CD146/MCAM is a marker of natural killer cell maturation," *Eur J Immunol*, 38(10):2855-64 (2008).
Duan, et al., "Targeting endothelial CD146 attenuates neuroinflammation by limiting lymphocyte extravasation to the CNS," *Sci Rep.* 3:1687:1-11, (2013).
Duda, et al., "Differential CD146 expression on circulating versus tissue endothelial cells in rectal cancer patients: implications for circulating endothelial and progenitor cells as biomarkers for antiangiogenic therapy," *J Clin Oncol.*, 20;24(9):1499-53, (Mar. 20, 2006).
Dye, et al., "hShroom1 links a membrane bound protein to the actin cytoskeleton. Cell Mol Life Sci," 66(4):681-696, (Feb. 2009).
Dye, et al., "Melanoma Biomolecules: Independently Identified but Functionally Intertwined," *Front Oncol.*, 3:252:1-17, (Sep. 24, 2013).
Elmageed, et al., "Clinical significance of CD146 and latexin during different stages of thyroid cancer," *Mol Cell Biochem*, 381:95-103 (2013).
Elshal, et al., "A unique population of effector memory lymphocytes identified by CD146 having a distinct immunophenotypic and genomic profile," *BMC Immunol.*, 8:29:1-15, (Nov. 13, 2007).
Elshal, et al., "CD146 (Mel-CAM), an adhesion marker of endothelial cells, is a novel marker of lymphocyte subset activation in normal peripheral blood," *Blood*,106(8):2923-2924, (Oct. 15, 2005).
EP Application No. 13836030.0 (Published as EP 2892562), Supplementary European Search Report and European Search Opinion, dated Apr. 4, 2016.
Feng, et al., "CD146 gene expression in clear cell renal cell carcinoma: a potential marker for of early recurrence after nephrectomy," *Int Urol Nephrol*, 44:1663-1669 (2012).
Filshie, et al., "MUC18, a member of the immunoglobulin superfamily, is expressed on bone marrow fibroblasts and a subset of hematological malignancies," *Leukemia*, 12:414-421 (1998).
Flanagan, et al., "Laminin-411 Is a Vascular Ligand for MCAM and Facilitates TH17 Cell Entry into the CNS," *PLoS One*, vol. 7, Issue 7, (2012).
Flanagan, et al., "Laminin-411 is a vascular ligand for MCAM and facilitates TH17 cell entry into the CNS," *PLoS One*, 7(7):1-11, (2012).
Freeman, et al., "Evaluation of a multi-marker immunomagnetic enrichment assay for the quantification of circulating melanoma cells," *J Transl Med.*, 10:192:1-9, (Sep. 15, 2012).
Geberhiwot, et al., "Rapid communication Erythromegakaryocytic Cells Synthesize Laminin-8 (α4β1γ1)", Experimental Cell Research, 254:189-195, (2000).
Gonzales, et al., "Structure and Function of a Vimentin-associated Matrix Adhesion in Endothelial Cells", Molecular biology of the Cell, vol. 12, 85-100 (Jan. 2001).
Gonzalez, et al., "Complex interactions between the laminin α4 subunit and integrins regulate endothelial cell behavior in vitro and angiogenesis in vivo", PNAS, vol. 99, No. 25, 16075-16080 (Dec. 10, 2002).
Gould Rothberg, et al., "Tissue biomarkers for prognosis in cutaneous melanoma: a systematic review and meta-analysis," *J Natl Cancer Inst*, 1;101(7):452-474, (Apr. 2009).
Grimm, et al., "Ectopic expression of carcinoembryonic antigen by a melanoma cell leads to changes in the transcription of two additional cell adhesion molecules," *Cancer Res.*, 55(15):3254-3257, (Aug. 1, 1995).
Guezguez, et al., "A dileucine motif targets MCAM-1 cell adhesion molecule to the basolateral membrane in MDCK cells," *FEBS Lett*, 580(15):3649-3656. (Jun. 26, 2006).
Guezguez, et al., "Dual role of Melanoma Cell Adhesion Molecule (MCAM)/CD146 in Lymphocyte Endothelium Interaction: MCAM/CD146 Promotes Rolling via Microvilli Induction in Lymphocyte and Is an Endothelial Adhesion Receptor," *Journal of Immunology*, 179:6673-6685 (2007).
Guezguez, et al., "Dual role of melanoma cell adhesion molecule MCAM)/CD146 in lymphocyte endothelium interaction: MCAM/

(56) References Cited

OTHER PUBLICATIONS

CD146 promotes rolling via microvilli induction in lymphocyte and is an endothelial adhesion receptor," *J Immunol.*, 79(10):6673-6685, (Nov. 15, 2007).

Hadjinicolaou, et al., "Relationship of CD146 expression to activation of circulating T cells: exploratory studies in healthy donors and patients with connective tissue disease," *Clin Exp Immunol.*, 174(1):73-88(Oct. 2013).

Hansen, et al., "Laminin-8/9 is synthesized by a rat glomerular mesangial cells and is required for PDGF-induced mesangial cell migration", Kidney International, vol. 64, pp. 110-118, (2003).

Heimberger, et al., "Loss of the AP-2alpha transcription factor is associated with the grade of human gliomas," *Clin Cancer Res.*, 11(1):267-272, (Jan. 1, 2005).

Huang, et al., "LAMA4, highly expressed in human hepatocellular carcinoma from Chinese patients, is a novel marker of tumor invasion and metastasis", J. Cancer Res. Clin. Oncol., 134:705-714, (2008).

Hung, et al., "The motor protein KIF14 inhibits tumor growth and cancer metastasis in lung adenocarcinoma," *PLoS One*, 8(4):1-14, (Apr. 23, 2013).

Imbert, et al., "CD146 expression in human breast cancer cell lines induces phenotypic and functional changes observed in Epithelial to Mesenchymal Transition," *PLoS One*, 7(8):1-8, (2012).

Ishikawa, et al., "Monoclonal antibodies to human laminin α4 chain globular domain inhibit tumor cell adhesion and migration on laminins 411 and 421, and binding of α6β1 integrin and MCAM to α4-laminins", Matrix Biology, 36:5-14 (2014).

Jean, et al., "Loss of AP-2 results in up-regulation of MCAM/MUC18 and an increase in tumor growth and metastasis of human melanoma cells," *J Biol Chem.*, 273(26):16501-16508, (Jun. 26, 1998).

Jean, et al., "Targeting the ATF-1/CREB transcription factors by single chain Fv fragment in human melanoma: potential modality for cancer therapy," *Crit Rev Immunol*, 21(1-3):275-86, (2001).

Jiang, et al., "CD146 is a coreceptor for VEGFR-2 in tumor angiogenesis. *Blood*," 120(11):2330-2339, (Sep. 13, 2012).

Johnson, "Cell adhesion molecules in the development and progression of malignant melanoma," Cancer Metastasis Rev,18(3):345-357,(1998).

Johnson, "Cell adhesion molecules of the immunoglobulin supergene family and their role in malignant transformation and progression to metastatic disease," Cancer Metastasis Rev. 10(1):11-22, (May 1991).

Johnson, et al, "MUC18: A cell adhesion molecule with a potential role in tumor growth and tumor cell dissemination," *Curr Top Microbiol Immunol*, 213 ( Pt 1):95-105, (1996).

Johnson, et al., "Functional aspects of three molecules associated with metastasis development in human malignant melanoma," *Invasion Metastasis*, 9(6):338-350, (1989).

Johnson, et al., "Melanoma Progression-Associated Glycoprotein MUC18/MCAM Mediates Homotypic Cell Adhesion Through Interaction With a Heterophilic Ligand," *Int. J. Cancer*, 73:769-774 (1997).

Johnson, et al., "The progression associated antigen MUC18: a unique member of the immunoglobulin supergene family," *Melanoma Res*, 3(5):337-340, (Oct. 1993).

Kamiyama, et al., Coexpression of CCR6 and CD146 (MCAM) is a marker of effector memory T-helper 17 cells, J Dermatol. 39(10):838-842, (Oct. 2012).

Kapoor, et al., "CD146 expression and its close relationship to tumor progression in systemic malignancies besides gall bladder carcinomas," *Tumour Biol.*, 34(2):1273-4 (Apr. 2013).

Katagiri, et al., "Screening of integrin-binding peptides from the laminin α4 and α5 chain G domain peptide library", Archives of Biochemistry and Biophysics, 521:32-42, (2012).

Kraus, et al, "Analysis of the expression of intercellular adhesion molecule-1 and MUC18 on benign and malignant melanocytic lesions using monoclonal antibodies directed against distinct epitopes and recognizing denatured, non-glycosylated antigen," *Melanoma Res*, Suppl 2:S75-81, (Aug. 1997).

Kristiansen, et al., "Expression of the cell adhesion molecule CD146/MCAM in non-small cell lung cancer," *Anal Cell Pathol.*, 25(2):77-81, (2003).

Lai, et al., "Expression and distribution of MUC18 in human uveal melanoma," *Virchows Arch*, 451(5):967-76, (Nov. 2007).

Larochelle, et al., "Melanoma cell adhesion molecule identifies encephalitogenic T lymphocytes and promotes their recruitment to the central nervous system," *Brain*, 135(Pt 10):2906-2924, (Oct. 2012).

Larochelle, et al., "Melanoma Cell Adhesion Molecule-jPositive CD8 T Lymphocytes Mediate Central Nervous System Inflammation", 78(1):39-53 (2015).

Lehmann, et al., "MUC18, a marker of tumor progression in human melanoma, shows sequence similarity to the neural cell adhesion molecules of the immunoglobulin superfamily," *Proc Natl Acad Sci U S A*, 1989 (24):9891-9895, (Dec. 1986).

Lei, et al., "The multifaceted role of CD146/MCAM in the promotion of melanoma progression", *Cancer Cell International*, 15:3 1-11 (2015).

Leslie, et al., "Immunization against MUC18/MCAM, a novel antigen that drives melanoma invasion and metastasis," *Gene Ther*, 14(4):316-323, (Oct. 5, 2006).

Leslie, et al., "Regulation of gene expression in melanoma: new approaches for treatment," *J Cell Biochem*, 94(1):25-38, (Jan. 2005).

Li, et al., "Increased expression of CD146 and microvessel density (MVD) in invasive micropapillary carcinoma of the breast: Comparative study with invasive ductal carcinoma-not otherwise specified," *Pathol Res Pract*, 207(12):739-746, (Dec. 15, 2011).

Li, et al., "Reciprocal regulation of MelCAM and AKT in human melanoma," *Oncogene*, 9;22(44):6891-6899. (Oct. 2003).

Lian, et al., "Identification of an active site on the laminin α4 chain globular domain that binds to αvβ3 integrin and promotes angiogenesis", Biochemical and Biophysical Research Communications, 347: 248-253, (2006).

Liu, et al., "Hypermethylation of MCAM gene is associated with advanced tumor stage in prostate cancer," *Prostate*, 68(4):418-426, (Mar. 1, 2008).

Ljubimova, et al., "Association between laminin-8 and glial tumor grade, recurrence, and patient survival," *Cancer*, 1;101(3):604-612, (Aug. 1, 2012).

Llie, et al., "Clinical value of circulating endothelial cells and of soluble CD146 levels in patients undergoing surgery for non-small cell lung cancer.," *Br J Cancer*, (Jan. 28, 2014).

Luca, et al., "Direct correlation between MUC18 expression and metastatic potential of human melanoma cells," *Melanoma Res*, 3(1):35-41. (Feb. 1993).

Luca, et al., "Molecular changes in human melanoma metastasis," *Histol Histopathol* 13(4):1225-1231 (Oct. 1998).

Luo, et al., "Recognition of CD146 as an ERM-binding protein offers novel mechanisms for melanoma cell migration," *Oncogene*, 31(3):306-321, (Jan. 19, 2012).

Ma, et al., "Synergistic killing effect between vorinostat and target of CD146 in malignant cells," *Clin Cancer Res*, 1;16(21):5165-5176, (Nov. 2010).

Maggi, et al., "CD161 is a marker of all human IL-17-producing T-cell subsets and is induced by RORC," *Eur J Immunol*, 40(8):2174-2181, (Aug. 2010).

Malpass, "Disease mechanisms in MS: Cell adhesion molecule MCAM on pathogenic T cells-a green light for CNS entry in multiple sclerosis," *Nat Rev Neurol*, 8(11):592, (Nov. 5, 2012).

Mantovani, "Inflaming metastasis," Nature, 457:36-37, (2009).

Matsuura, et al., "Localization of the Laminin αChain in the Skin and Identification of a Heparin-Dependent Cell Adhesion site within the Laminin α4 Chain C-Terminal LG 4 Module," The Journal of Investigative Dermatology, 122:614-620 (2004).

McGary, et al., "A fully human antimelanoma cellular adhesion molecule/MUC18 antibody inhibits spontaneous pulmonary metastasis of osteosarcoma cells in vivo," *Clin Cancer Res*, 15;9(17):6560-6566, (Dec. 2003).

(56) References Cited

OTHER PUBLICATIONS

McGary, et al., "Cellular adhesion pathways and metastatic potential of human melanoma," *Cancer Biol Ther*, 1(5):459-465, (Sep.-Oct. 2002).
Melnikova, et al., "Bioimmunotherapy for melanoma using fully human antibodies targeting MCAM/MUC18 and IL-8," *Pigment Cell Res*, 19(5):395-405, (Oct. 2006).
Mills, et al., "Fully human antibodies to MCAM/MUC18 inhibit tumor growth and metastasis of human melanoma," *Cancer Res*, 1;62(17):5106-5114, (Sep. 2002).
Minato, et al., "Comparative immunohistochemical analysis of IMP3, GLUT1, EMA, CD146, and desmin for distinguishing malignant mesothelioma from reactive mesothelial cells," *Am J Clin Pathol*, 141(1):85-93, (Jan. 2014).
Mintz-Weber, et al., "Identification of the elements regulating the expression of the cell adhesion molecule MCAM/MUC18. Loss of AP-2 is not required for MCAM expression in melanoma cell lines," *J Biol Chem*, 3;275(44):34672-34680, (Nov. 2000).
Neidhart, et al., "Synovial fluid CD146 (MUC18), a marker for synovial membrane angiogenesis in rheumatoid arthritis," *Arthritis Rheum*, 42(4):622-630, (Apr. 1999).
Nyormoi, et al., "Transcriptional regulation of metastasis-related genes in human melanoma," *Clin Exp Metastasis*, 20(3):251-63, (2003).
Ody et al., "Surface molecules involved in avian T-cell progenitor migration and differentiation," *Dev Immunol*, 7(2-4):267-277, (2007).
Oikawa, et al., "Melanoma cells produce multiple laminin isoforms and strongly migrate on α5 laminin(s) via several integrim receptors", Experimental Cell Research, 317:1110-1133, (2011).
Oka, et al., "The expression of CD146 predicts a poor overall survival in patients with adenocarcinoma of the lung," *Anticancer Res.*, 32(3):861-4 (2012).
Okazaki, et al., "CD146 and insulin-like growth factor 2 mRNA-binding protein 3 predict prognosis of asbestos-induced rat mesothelioma," *Cancer Sci*, 104(8):989-995, (Aug. 2013).
Okumura, et al., "Involvement of gicerin in the extension of microvilli," *Exp Cell Res*, 271(2):269-276, (Dec. 10, 2011).
Ouhtit, et al., "Towards understanding the mode of action of the multifaceted cell adhesion receptor CD146," *Biochim Biophys Acta*, 1795(2):130-136. (Apr. 2009).
Pacifico, et al., "Development of a tissue array for primary melanoma with long-term follow-up: discovering melanoma cell adhesion molecule as an important prognostic marker," *Plast Reconstr Surg.*, 115(2):367-75, (2005).
Pantel, et al., "Early metastasis of human solid tumours: expression of cell adhesion molecules," *Ciba Found Symp*, 189:157-170; (1995).
Pardo, et al., "The characterization of the invasion phenotype of uveal melanoma tumour cells shows the presence of MUC18 and HMG-1 metastasis markers and leads to the identification of DJ-1 as a serum biomarker," *Int J Cancer*, 1;119(5):1014-1022, (Sep. 2006).
PCT/IB2015/051785 International Search Report and Written Opinion dated Jul. 23, 2015.
PCT/IB2015/051863 International Search Report and Written Opinion dated Aug. 26, 2015.
PCT/IB2015/051863 Invitation to Pay Additional Fees and, Where Applicable, Protest Fee mailed Jun. 17, 2015.
PCT/IB2015/051787 International Search Report and Written Opinion dated Jun. 22, 2015.
PCT/IB2015/051789 International Search Report and Written Opinion dated Aug. 13, 2015.
PCT/IB2015/051790 International Search Report and Written Opinion dated Jun. 25, 2015.
PCT/US2012/000274 International Preliminary Report of Patentability and Written Opinion dated Dec. 10, 2013.
PCT/US2012/000274 International Search Report dated Sep. 26, 2012.
PCT/US2013/058773 International Search Report and Written Opinion dated Apr. 16, 2014.
PCT/US2013/058773 Invitation to Pay Additional Fees and, Where Applicable, Protest Fee mailed Jan. 23, 2014.
PCT/US2013/058773 Preliminary report on Patentability dated Mar. 19, 2015.
Perego, et al., "Heterogeneous phenotype of human melanoma cells with in vitro and in vivo features of tumor-initiating cells," *J Invest Dermatol*, 130(7):1877-1886, (Jul. 2010).
Petajaniemi, et al., "Localization of laminin alpha4-chain in developing and adult human tissues," *J Histochem Cytochem*, 50(8):1113-1130, (Aug. 2002).
Pickl, et al., "MUC18/MCAM (CD146), an activation antigen of human T lymphocytes," *J Immunol*, 158(5):2107-2115, (Mar. 1, 1997).
Pierce, et al., "Expression of Laminin α3, α4, and α5 Chains by Alveolar Epithelial Cells and Fibroblasts", American Journal of Respiratory Cell and Molecular Biology, vol. 19, pp. 237-244 (1998).
Pires, et al., "Mel-CAM (CD146) expression in parotid mucoepidermoid carcinoma," *Oral Oncology*, 39:277-281 (2003).
Pujades, et al., "Melanoma Cell Adhesion Molecule (MCAM) expression in the myogenic lineage during early chick embryonic development," *Int J Dev Biol*, 46(2):263-266, (Mar. 2002).
Rapanotti, et al., "Blood MUC-18/MCAM expression in patients with melanoma: a suitable marker of poor outcome," *Br J Dermatol*, 169(1):221-222, (Jul. 2013).
Rapanotti, et al., "Melanoma-associated markers expression in blood: MUC-18 is associated with advanced stages in melanoma patients," *Br J Dermatol*, 160(2):338-344, (Feb. 2008).
Reboldi, et al., "C-C chemokine receptor 6-regulated entry of TH-17 cells into the CNS through the choroid plexus is required for the initiation of EAE," *Nat Immunol*, 10(5):514-523, (May 2009).
Reid, et al., "Markers of circulating tumour cells in the peripheral blood of patients with melanoma correlate with disease recurrence and progression," *Br J Dermatol*,168(1):85-92. (Jan. 2013).
Rice, et al., "Anti-α4 integrin therapy for multiple sclerosis", *Neurology*, 64:1336-1342 (2005).
Roep, et al., "The problems and promises of research into human immunology and autoimmune disease", Nature Medicine, 18(1):48-53 (2012).
Romagnani, et al., "Properties and origin of human Th17 cells," *Mol Immunol*, 47(1):3-7, (Nov. 2009).
Rossi, et al., "Vascular inflammation in central nervous system diseases: adhesion receptors controlling leukocyte-endothelial interactions," Journal of Leukocyte Biology, 89:529-556 (2011).
Sato, et al., "Immunocytochemistry of CD146 is useful to discriminate between malignant pleural mesothelioma and reactive mesothelium," *Mod Pathol*, 23(11):1458-1466, (Nov. 2010).
Satyamoorthy, et al., "Mel-CAM-specific genetic suppressor elements inhibit melanoma growth and invasion through loss of gap junctional communication," *Oncogene*, 2;20(34):4676-4684, (Aug. 2001).
Schiano, et al., "Different expression of CD146 in human normal and osteosarcoma cell lines," *Med Oncol*, 29(4):2998-3002. (Dec. 2012).
Schlagbauer-Wadl, et al., "Influence of MUC18/MCAM/CD146 expression on human melanoma growth and metastasis in SCID mice," *Int J Cancer*, 11;81(6):951-955, (Jun. 1999).
Schrage, et al., "Murine CD146 is widely expressed on endothelial cells and is recognized by the monoclonal antibody ME-9F1," *Histochem Cell Biol*,129(4):441-451, (Apr. 2008).
Schwarz, et al., "Melanoma-associated adhesion molecule MUC18/MCAM (CD146) and transcriptional regulator mader in normal human CNS," *Neuroimmunomodulation*, 5(5):270-276, (Sep.-Oct. 1998).
Sers, et al., "Genomic organization of the melanoma-associated glycoprotein MUC18: implications for the evolution of the immunoglobulin domains," *Proc Natl Acad Sci USA*, 15;90(18):8514-8518, (Sep. 1993).
Sers, et al., "MUC18, a melanoma-progression associated molecule, and its potential role in tumor vascularization and hematogenous spread," *Cancer Res*, 1;54(21):5689-5694. (Nov. 1994).

(56) References Cited

OTHER PUBLICATIONS

Shih et al., "A New Mel-CAM (CD146)-Specific Monoclonal Antibody, MN-4, on Paraffin-Embedded Tissue", *Modern Pathology*, 11(11):1098-1106, (1998).

Shih, "The role of CD146 (Mel-CAM) in biology and pathology," *J Pathol*, 189(1):4-11, (Sep. 1999).

Shih, et al., "Melanoma cell-cell interactions are mediated through heterophilic Mel-CAM/ligand adhesion," *Cancer Res*, 1;57(17):3835-3840, (Sep. 1997).

Shih, et al., "Regulation of Mel-CAM/MUC18 expression on melanocytes of different stages of tumor progression by normal keratinocytes," *Am J Pathol*, 145(4):837-845, (Oct. 1994).

Shih, et al., "The cell-cell adhesion receptor Mel-CAM acts as a tumor suppressor in breast carcinoma," *Am J Pathol*, 151(3):745-751, (Sep. 1997).

Sixt, et al., "Endothelial cell laminin isoforms, laminins 8 and 10, play decisive roles in T cell recruitment across the blood-brain barrier in experimental autoimmune encephalomyelitis," *J Cell Biol*, 28;153(5):933-946, (May 2001).

Solovey, et al., "Identification and functional assessment of endothelial P1H12," *J Lab Clin Med*, 138(5):322-331, (Nov. 2001).

Takaha, et al., "Expression of gicerin in development, oncogenesis and regeneration of the chick kidney," *Differentiation*, 58(5):313-320, (Jun. 1995).

Talts, et al., "Structural and Functional Analysis of the Recombinant G. Domain of the Laminin α4 Chain and Its Proteolytic Processing in Tissues", The Journal of Biological Chemistry, vol. 275, No. 45, pp. 35192-35199, (Nov. 10, 2000).

Tian, et al., "CD146 protein as a marker to predict postoperative liver metastasis in colorectal cancer," *Cancer Biother Radiopharm*, 28(6):466-470, (Jul.-Aug. 2013).

Tsuchiya, et al., Gicerin, a cell adhesion molecule, promotes the metastasis of lymphoma cells of the chicken, *Cell Tissue Res*, 314(3):389-397, (Dec. 2003).

Tsukamoto, aet al., "Involvement of gicerin, a cell adhesion molecule, in development and regeneration of oviduct and metastasis of oviductal adenocarcinomas of the chicken," *Exp Cell Res*, 247(2):329-338, (Mar. 15, 1999).

Tsukamoto, et al., "E. Gicerin, an Ig-superfamily cell adhesion molecule, promotes the invasive and metastatic activities of a mouse fibroblast cell line," *J Cell Physiol*, 197(1):103-109, (Oct. 2003).

Tsukamoto, et al., "Expression of gicerin enhances the invasive and metastatic activities of a mouse mammary carcinoma cell line," *Int J Oncol*, 23(6):1671-1677, (Dec. 2003).

Tsukamoto, et al., The role of gicerin, a novel cell adhesion molecule, in development, regeneration and neoplasia, *Histol Histopathol*, 16(2):563-571, (Apr. 2001).

U.S. Appl. No. 14/021,777 Final Office Action dated Jan. 29, 2016.
U.S. Appl. No. 14/021,777 Notice of Allowance dated Apr. 25, 2016.
U.S. Appl. No. 14/021,777 Restriction Requirement dated Apr. 14, 2015.
U.S. Appl. No. 14/124,620 Final Office Action dated Sep. 22, 2016.
U.S. Appl. No. 14/124,620 Non-Final Office Action dated Feb. 24, 2016.
U.S. Appl. No. 14/021,777 Non-Final Office Action dated Sep. 16, 2015.
U.S. Appl. No. 14/124,620 Restriction Requirement dated Sep. 23, 2015.
U.S. Appl. No. 14/656,619 Restriction Requirement dated Aug. 11, 2016.

Vaninio, et al., "HEMCAM, an adhesion molecule expressed by c-kit+ hemopoietic progenitors," *J Cell Biol*, 135(6 Pt 1):1655-1668, (Dec. 1996).

Wang, et al., "A novel 'piipeline' system for downstream preparation of therapeutic monoclonal antibodies", *Biotechmol Lett*, 35:1411-1419, (2013).

Wang, et al., "CD146, a multi-functional molecule beyond adhesion," *Cancer Lett*, 330(2):150-162, (Apr. 28, 2013).

Wang, et al., "Identification of CD146 expression, angiogenesis, and lymphangiogenesis as progression, metastasis and poor-prognosis related markers for gallbladder adenocarcinoma," *Tumor biol.*, 33:173-182 (2012).

Waston-Hurst, et al., "The role of N-cadherin, MCAM and beta3 integrin in melanoma progression, proliferation, migration and invasion," *Cancer Biol Ther*, 5(10):1375-1382, (Oct. 2006).

Wellbrock, et al., "CD146: a new partner for VEGFR2," *Blood*, 13;120(11):2164-2165, (Sep. 2012).

Weninger, et al., "Keratinocytes express the CD146 (Muc18/S-endo) antigen in tissue culture and during inflammatory skin diseases," *J Invest Dermatol*, 115(2):219-224, (Aug. 2000).

Witze, et al., "Wnt5a control of cellpolarity and directional movement by polarized redistribution of adhesion receptors," *Science*, 320(5874):365-369, (Apr. 2008).

Wong, et al., "The role of immunoglobulin superfamily cell adhesion molecules in cancer metastasis," *Int J Cell Biol*, ;2012:340296, (2012).

Wu, et al., "Ectopical expression of human MUC18 increases metastasis of human prostate cancer cells," *Gene*, 327(2):201-213. (Mar. 2004).

Wu, et al., "Endothelial basement membrane laminin alpha5 selectively inhibits T lymphocyte extravasation into the brain," *Nat Med*, 15(5):519-27. (May 2009).

Wu, et al., "Enforced expression of MCAM/MUC18 increases invitro motility and invasiveness and in vivo metastasis of two mouse melanoma K1735 sublines in a syngeneic mouse model," *Mol Cancer Res*, 6(11):1666-1677 (Nov. 2008).

Wu, et al., "Enforced expression of METCAM/MUC18 increases tumorigenesis of human prostate cancer LNCaP cells in nude mice," *J Urol*, 185(4):1504-1512, (Apr. 2011).

Wu, et al., "Expression of a human cell adhesion molecule, MUC18, in prostate cancer cell lines and tissues," *Prostate*, 48(4):305-315 (Sep. 2001).

Wu, et al., "MCAM is a novel metastasis marker and regulates spreading, apoptosis and invasion of ovarian cancer cells," *Tumour Biol*, 33(5):1619-1628, (Oct. 2012).

Xie, et al., "Expression of MCAM/MUC18 by human melanoma cells leads to increased tumor growth and metastasis," *Cancer Res*, 1;57(11):2295-2303, (Jun. 1997).

Yamashita, et al., "Cryptic fragment α4 LEG4-5 derived from laminin α4 chain inhibits de novo adipogenesis by modulating the effect of fibroblast growth factor-2", Develop. Growth Differ., 50:97-107 (2008).

Yan, et al., "A novel anti-CD146 monoclonal antibody, AA98, inhibits angiogenesis and tumor growth," *Blood*, 1;102(l):184-191, (Jul. 2003).

Yang, et al., "Isolation and characterization of mouse MUC18 cDNA gene, and correlation of MUC18 expression in mouse melanoma cell lines with metastatic ability," *Gen*, 265(1-2):133-45, (Mar. 2001).

Yousif, et al., "Laminin isoforms in endothelial and perivascular basement membranes," *Cell Adh Migr*, 7(1):101-110, (Jan.-Feb. 2013).

Yun et al: "A Novel Antibody AA98 $V_H$/L Directed Against CD146 Efficiently Inhibits Angiogenesis", Anticancer Research, 27(6B):4219-4224, (2007).

Zabouo, et al., "CD146 expression is associated with a poor prognosis in human breast tumors and with enhanced motility in breast cancer cell lines," *Breast Cancer Res*, 11(1):R1, (2009).

Zeng, et al., "CD146, an epithelial-mesenchymal transition inducer, is associated with triple-negative breast cancer," *Proc Natl Acad Sci U S A*, 24;109(4):1127-1132, (Jan. 2012).

Zeng, et al., "Up-regulation of METCAM/MUCI8 promotes motility, invasion, and tumorigenesis of human breast cancer cells," *BMC Cancer*, 30;11:113, (Mar. 2011).

Zhang, et al., "CD146 is a potential marker for the diagnosis of malignancy in cervical and endometrial cancer," *Oncol Lett*, 5(4):1189-1194, (Apr. 2013).

Zhang, et al., "Generation and characterization of a panel of monoclonal antibodies against distinct epitopes of human CD146," *Hybridoma (Larchmt)*, 27(5):345-52, (Oct. 2008).

(56) References Cited

OTHER PUBLICATIONS

Zigler, et al., "Expression of Id-1 is regulated by MCAM/MUC18: a missing link in melanoma progression," *Cancer Res*, 15;71(10):3494-3504 (May 2011).

Zigler, et al., "Tumor immunotherapy in melanoma: strategies for overcoming mechanisms of resistance and escape," *Am J Clin Dermatol*, 9(5):307-311, (2008).

U.S. Appl. No. 14/656,619 Final Office Action dated Jun. 13, 2017.

Galvez, "Role of Th17 Cells in the Pathogenesis of Human IBD," *ISRN Inflammation*, vol. 201.4, Article ID 938461, 14 pages, retrieved from <http://dx.doi.org/10.1155/2014/928461> (2014).

Jarasch, et al., "Developability Assessment During the Selection of Novel Therapeutic Antibodies", *Journal of Pharmaceutical Sciences*, 104:1855-1898 (2015).

Loricera, et al., "Tocilizumab in giant cell arteritis: Multicenter open-label study of 22 patients", *Seminars in Arthritis and Rheumotisum*, 44:717-723 (2015).

Nobbmann, et al., "Dynamic light scattering as a relative tool for assessing the molecular integrity and stability of monoclonal antibodies", *Biotechnology and Genetic Engineering Review*, vol. 24, 117-128 (2007).

PCT/IB2015/051785 International Preliminary Report on Patentability and Written Opinion dated Sep. 13, 2016.

PCT/IB2015/051786 International Preliminary Report on Patentability and Written Opinion dated Sep. 13, 2016.

PCT/IB2015/051787 International Preliminary Report on Patentability and Written Opinion dated Sep. 13, 2016.

PCT/IB2015/051790 International Preliminary Report on Patentability and Written Opinion dated Sep. 13, 2016.

PCT/IB2016/055557 Invitation to Pay Additional Fees and, Where Applicable, Protest Fee mailed Dec. 6, 2016.

U.S. Appl. No. 14/427,290 Final Office Action dated Feb. 2, 2017.

U.S. Appl. No. 14/656,619 Non-Final Office Action dated Dec. 28, 2016.

Zheng, et al., "Endothelial CD146 is required for in vitro tumor-induced angiogenesis: The role of a disulfide bond in signaling and dimerization," *The International Journal of Biochemistry & Cell Biology*, 41:2163-2172 (2009).

U.S. Appl. No. 14/656,596 Restriction Requirement dated Feb. 14, 2017.

PCT/IB2016/055559 International Preliminary Report on Patentability and Written Opinion dated Mar. 31, 2017.

PCT/IB2016/055559 Invitation to Pay Additional Fees, and, Where Applicable, Protest Fee mailed Dec. 5, 2016.

PCT/IB2016/055557 International Search Report and Written Opinion dated Apr. 7, 2017.

U.S. Appl. No. 14/656,596 Restriction Requirement dated May 11, 2017.

PCT/IB2017/051264 Invitation to Pay Additional Fees and, Where Applicable, Protest Fee mailed May 22, 2017.

Mukhopadhyay, "Granulomatous Lung Disease," *Arch Pathol Lab Med*, vol. 134, pp. 667-690, (May 2010).

PCT/IB2017/05142 Invitation to Pay Additional Fees and, Where Applicable, Protest Fee mailed Jun. 2, 2017.

Flanagan, " Prothena to Present Precinical Data for PRX003 at 2016 AAAAI Annual Meeting," (Mar. 6, 2016).

U.S. Appl. No. 14/656,596 Non-Final Office Action dated Aug. 0, 2017.

PCT/IB2017/05142 International Search Report and Written Opinion dated Aug. 8, 2017.

Wouters, et al., "Blau Syndrome, the prototypic auto-inflammatory granulomatous disease," *Pediatrk Pheumotology*, 12:33 (2014).

PCT/IB2017051264 International Search Report and Written Opinion dated Aug. 8, 2017.

PCT/IB2017/053289 International Search Report and Written Opinion dated Aug. 8, 2017.

Flanagan, "Anti-Mcam Monoclonal Antibody PRX003 Inhibits the Unique Migratory Potential of Pathogenic IL-17-Producing T Cellls," *J Allergy Clin Immunol*, AB190 Abtracts, (Fed 2016).

Prothena, "Prothena Reports Results of Phase 1 Single Ascending Dose Study of PRX003, Demonstrating Target Engagement of the Novel Anti-MCAM Antibody for Inflammatory Disease", Jun. 9, 2016, Retrieved from the Internet: URL:http://files.shareholder.com/downloads/AMDA-1GZ5QD/4888716237x0x895935/C889B509-F11C-4742-PFFD-AD031305F573/PRTA_News_2016_6_9_General_Releases.pdf retrieved on Jul. 31, 2017.

Koller, et al., "OPO205 Clinical and Preclinical Assessment of the Anti-MCAM Monoclonal Antibody PRX003, A Potential Novel Treatment for Th17-Mediated Inflammatory Disease," *Annals of the Rheumatic Diseases*, vol. 75, No. Suppl 2 (Jun. 2016).

Kinney, et al., "Clinical Assessment of the Monoclonal Antibody, PRX003, a Potential Novel Treatment for Th17-Mediated Inflammatory Disease," *Arthritis Rgeumatol*, vol. 68, No. Suppl 10, (Sep. 28, 2016).

U.S. Appl. No. 15/222,848, filed Jul. 28, 2016.
U.S. Appl. No. 15/222,849, filed Jul. 28, 2016.
U.S. Appl. No. 15/726,170, filed Oct. 5, 2017.
U.S. Appl. No. 15/125,569, filed Sep. 12, 2016.
U.S. Appl. No. 14/656,619, filed Mar. 12, 2015.
U.S. Appl. No. 14/656,596, filed Mar. 12, 2015.
U.S. Appl. No. 15/268,178, filed Sep. 12, 2016.
U.S. Appl. No. 15/268,295, filed Sep. 12, 2016.
PCT/IB2016/055559 filed Sep. 16, 2016.
PCT/IB2016/055557 filed Sep. 16, 2016.
PCT/IB2017/051264 filed Mar. 3, 2017; and.
PCT/IB2017/053289 filed Jun. 2, 2017.
U.S. Appl. No. 12/125,568, filed Sep. 12, 2016.
U.S. Appl. No. 61/527,481, filed Aug. 25, 2011.
U.S. Appl. No. 61/493,780, filed Jun. 6, 2011.
PCT/US2012/000274 filed Jun. 6, 2012.
U.S. Appl. No. 61/698,916, filed Sep. 10, 2012.
U.S. Appl. No. 61/797,179, filed Nov. 30, 2012.
U.S. Appl. No. 61/797,356, filed Dec. 5, 2012.
PCT/US2013/058773 filed Sep. 9, 2013.
U.S. Appl. No. 61/952,129, filed Mar. 12, 2014.
U.S. Appl. No. 62/023,753, filed Jul. 11, 2014.
U.S. Appl. No. 62/068,286, filed Oct. 24, 2014.
U.S. Appl. No. 62/086,600, filed Dec. 2, 2014.
PCT/IB2015/051789 filed Mar. 12, 2015.
U.S. Appl. No. 61/952,132, filed Mar. 12, 2014.
U.S. Appl. No. 62/023,760, filed Jul. 11, 2014.
U.S. Appl. No. 62/068,349, filed Oct. 24, 2014.
U.S. Appl. No. 14/656,501, filed Mar. 12, 2015.
PCT/IB2015/051790 filed Mar. 12, 2015.
U.S. Appl. No. 61/952,123, filed Mar. 12, 2014.
U.S. Appl. No. 62/023,698, filed Jul. 11, 2014.
U.S. Appl. No. 62/068,438, filed Oct. 24, 2014.
PCT/IB2015/051786 filed Mar. 12, 2015.
U.S. Appl. No. 61/952,116, filed Mar. 12, 2014.
U.S. Appl. No. 61/952,833, filed Mar. 13, 2014.
U.S. Appl. No. 62/023,724, filed Jul. 11, 2014.
U.S. Appl. No. 62/068,419, filed Oct. 24, 2014.
PCT/IB2015/051787 filed Mar. 12, 2105.
U.S. Appl. No. 62/219,599, filed Sep. 16, 2015.
U.S. Appl. No. 62/219,611, filed Sep. 16, 2015.
U.S. Appl. No. 14/427,290, filed Mar. 10, 2015.
U.S. Appl. No. 62/303,360, filed Mar. 3, 2016.
U.S. Appl. No. 62/303,369, filed Mar. 3, 2016; and.
U.S. Appl. No. 62/345,732, filed Jun. 3, 2016.
U.S. Appl. No. 61/952,835, filed Mar. 13, 2014.
U.S. Appl. No. 62/023,577, filed Jul. 11, 2014; and.
PCT/IB2015/051785 filed Mar. 12, 2015.
U.S. Appl. No. 14/656,596 Non/Final Office Action dated Feb. 1, 2018.

Van Regenmortel, "Mapping Epitope Structure and Activity: From One-Dimensional Prediction to Four-Dimensional Description of Antigenic Specificity," *Methods: A Comparison to Methods in Enzymology*, 9(3), 465-472, (1996).

Abaza, et al., "Effects of Amino Acid Substitutions Outside an Antigenic Site on Protein Binding to Monoclonal Antibodies of Predetermined Specificity Obtained by Peptide Immunization: Dem-

(56) References Cited

OTHER PUBLICATIONS onstration with Region 94-100 (Antigenic Site 3) of Myoglobin," *Journal of Protein Chemistry*, vol. 11, No. 5, pp. 433-444, (1992).
PCT/IB2016/055559 International Preliminary Report on Patentability dated Mar. 29, 2018.
PCT/IB2016/055557 International Preliminary Report on Patentability dated Mar. 29, 2018.
U.S. Appl. No. 15/125,270 Non-Final Office Action dated Apr. 27, 2018.
U.S. Appl. No. 15/268,178 Non-Final Office Action dated Apr. 27, 2018.
Wu, et al., "Relationship of CD146 expression to secretion of interleukin (IL)-17, IL-22 and interferon-y by CD4+ T cells in patients with inflammatory arthritis," *Clin Exp Immunol.*, 179(3): 378-391, (2015).
Zhang, et al., "Elevated Levels of soluble and Neurtrophil CD 146 in Active Systemic Vasculitis," *Science*, vol. 40, No. 6, pp. 351-356, (Jun. 2009).
Rose, "Prothena Ends an early Stage Psoriasis Drug After Data Failed to Wow its Researchers," *Filter News*, pp. 1-6, (Sep. 29, 2017).
Rose, Prothena Reports Results from Phase 1b Multiple Ascending Dose Study of PRX003 in Patients with Psoriasis,Press Release, Sep. 28, 2017.
U.S. Appl. No. 15/222,484 Non-Final Office Action dated Apr. 27, 2018.
Taylor, "Prothena scratches MCAM psoriasis antibody after negative trial," *Gene Therapy & Immunotherapy; Alphabetical Glossary of Terms*, revised 22nd Edition, Sep. 29, 2017.
U.S. Appl. No. 15/222,849 Non-Final Office Action dated May 4, 2018.
Hafner, et al., "Selection of Mimotopes of the Cell Surface Adhersion Molecule Mel-CAM from a Random pVIII-28aa Phage Peptide Library," *The Journal of Investigative Dermatology*, vol. 119, No. 4, pp. 865-869, (Oct. 2002).
Stalin, et la., "Therapeutic and Diagnostic Antibodies to CD146: Thirty Years of Research on Its Potential for Detection and Treatment of Tumors," *Antibodies*, 6, 17, doi:10.33090/antib6040017, (2017.
U.S. Appl. No. 15/268,295 Restriction Requirement dated Mar. 12, 2018.
U.S. Appl. No. 14/124,620 Non-Final Office Action dated May 23, 2018.
U.S. Appl. No. 14/656,619 Notice of Allowance dated Feb. 27, 2018.
PCT/IB2015/051789 International Preliminary Report of Patentability and Written Opinion dated Sep. 10, 2016.
PCT/IB2017/051402 International Search Report and Written Opinion dated Aug. 8, 2017.
U.S. Appl. No. 15/125,568 Restriction Requirement dated Sep. 21, 2018.
U.S. Appl. No. 15/125,570 Final Office Action dated Sep. 24, 2018.
U.S. Appl. No. 15/222,849 Final Office Action dated Sep. 24, 2018.
PCT/IB2017/051402 International Preliminary Report on Patentability dated Sep. 20, 2018.
PCT/IB2017/051400 International Preliminary Report on Patentability dated Sep. 20, 2018.
Dajur, et al., "Secretion of interleukin-17 by CD8+ T cells expressing CD146 (MCAM)," *Clinical Immunology*, 152, 36-47, (2014).
Mayer, et al., "Sarcoidosis and Chronic Beryllium Disease: Similarities and Differences," *Semin Respir Crit Care Med*, 35:316-329, (2014).
Li, et al., "D38. Flying: Reaching New Heights in Sarconidosis," *American Journal of Respiratory and Critical Care Medicine*, 191, A5822, (2015).
PCT/US2013/058773 International Preliminary Report on Patentability dated Mar. 10, 2015.
U.S. Appl. No. 14/124,620 Final Office Action dated Oct. 16, 2018.
U.S. Appl. No. 14/124,620 Advisory Action dated Jan. 25, 2019.
U.S. Appl. No. 15/125,570 Advisory Action dated Jan. 31, 2019.
U.S. Appl. No. 15/222,848 Final Office Action dated Oct. 26, 2018.
U.S. Appl. No. 15/726,170 Non-Final Office Action dated Jan. 15, 2019.
U.S. Appl. No. 15/125,568 Non-Final Office Action dated Mar. 14, 2019.
Colman, "Effects of amino acid sequence changes on antibody-antigen interactions," *Research in Immunology*, 145:33-36, (1994).
Harding, et al., "The immunogenicity of humanized and fully human antibodies," *mAbs*, vol. 2, Issue 3, 256-265, (2010).
Chen, et al., "Enhancement and destruction of antibody function by somatic mutation: unequal occurrence is controlled by V gene combinatorial associations," *The EMBO Journal*, vol. 14, No. 12, pp. 2784-2794, (1995).
Kussie, et al., "A Single Engineered Amino Acid Substitution Changes Antibody Fine Specificity," *Journal of Immunology*, pp. 146-152, (1994).
Rudidof, et al., "Single amino acid substitution altering antigen-binding specificity," *PNAS*, 79: 1979-1983, (1982).

\* cited by examiner

Figure 3A

[Sequence alignment of 1749VL protein, 2LTQVL, ABA71407.1, CAI99800.1, and hul749VLv3 protein against Majority consensus, residues 1-113]

Figure 3B

[Sequence alignment of 1749VH protein, 1RIIVH, AAK82494.1, ADX65676.1, and hul749VHv3 protein against Majority consensus, residues 1-120]

Decoration 'Decoration #1': Box residues that differ from the Consensus.

ANTI-MCAM ANTIBODIES AND ASSOCIATED METHODS OF USE

CROSS REFERENCE TO RELATED APPLICATIONS

This application is a US National Stage of PCT/IB2015/051786 filed Mar. 12, 2015, which claims priority to U.S. Provisional Application No. 61/952,123, filed Mar. 12, 2014, U.S. Provisional Application No. 62/023,698, filed Jul. 11, 2014, and U.S. Provisional Application No. 62/068,438, filed Oct. 24, 2014, each of the aforementioned applications is incorporated in its entirety herein for all purposes.

REFERENCE TO A SEQUENCE LISTING

The Sequence Listing written in file 481067SEQLIST.txt, created on Sep. 12, 2016, for "ANTI-MCAM ANTIBODIES AND ASSOCIATED METHODS OF USE" is 153 kilobytes. The information contained in this file is hereby incorporated by reference.

BACKGROUND

A subset of CD4+ T cells, termed TH17 cells (T helper 17 cells), has been implicated in the pathogenesis of a number of autoimmune diseases, particularly those neuroinflammatory conditions involving CNS infiltration of T cells, such as multiple sclerosis and the animal model, experimental autoimmune encephalomyelitis (EAE). TH17 cells have been reported to secrete a number of select cytokines including IL-17 and IL-22. TH17 cells have been reported to undergo specific recruitment and infiltration of tissue. MCAM has been reported to be expressed on TH17 cells and to bind laminin alpha-4 as a ligand.

SUMMARY OF THE CLAIMED INVENTION

The invention provides humanized antibodies comprising a mature heavy chain variable region comprising the three Kabat CDRs of SEQ ID NO:156, and being at least 97% identical to SEQ ID NO:156, and a mature light chain variable region comprising the three Kabat CDRs of SEQ ID NO:160, and being at least 97% identical to SEQ ID NO:160. In some antibodies, the mature heavy chain variable region is at least 98% or 99% identical to SEQ ID NO:156 and the mature light chain variable region is at least 98% or 99% identical to SEQ ID NO:160. In some antibodies, the mature heavy chain variable region has the amino acid sequence of SEQ ID NO:156 and the mature light chain variable region has the amino acid sequence of SEQ ID NO:160. In some antibodies, position 93 (Kabat numbering) of the mature heavy chain variable region is occupied by T; position 42 (Kabat numbering) of the mature heavy chain variable region is occupied by E; position 43 (Kabat numbering) of the mature light chain variable region is occupied by S; position 9 (Kabat numbering) of the mature light heavy chain variable region is occupied by S; position 19 (Kabat numbering) of the mature light heavy chain variable region is occupied by V. In some antibodies, position 93 (Kabat numbering) of the mature heavy chain variable region is occupied by T; position 42 (Kabat numbering) of the mature heavy chain variable region is occupied by E; position 3 (Kabat numbering) of the mature heavy chain variable region is occupied by K, position 43 (Kabat numbering) of the mature light chain variable region is occupied by S; position 9 (Kabat numbering) of the mature light heavy chain variable region is occupied by S; position 19 (Kabat numbering) of the mature light heavy chain variable region is occupied by V. In some antibodies, the heavy chain constant region has the amino acid sequence of SEQ ID NO: 173 or 174 and/or the light chain constant region has the amino acid sequence of SEQ ID NO: 170 or 171.

Then invention further provides anti-MCAM antibodies that bind to human MCAM (SEQ ID NO:11) at an epitope including amino acid residue 318. In some such antibodies, the epitope comprises amino acid residue 324. In some such antibodies, the epitope comprises amino acid residue 326. In some antibodies, the epitope comprises at least five contiguous amino acids residues of human MCAM including amino acid residue 318. In some such antibodies, the antibody is not an antibody selected from the group consisting of:
(a) clone 15 having a mature heavy chain variable region corresponding to SEQ ID NO:18 and a mature light chain variable region corresponding to SEQ ID NO:13;
(b) clone 17 having a mature heavy chain variable region corresponding to SEQ ID NO:7 and a mature light chain variable region corresponding to SEQ ID NO:2;
(c) 1174.1.3 having a mature heavy chain variable region corresponding to SEQ ID NO:35 and a mature light chain variable region corresponding to SEQ ID NO:30;
(d) 1414.1.2 having a mature heavy chain variable region corresponding to SEQ ID NO:45 and a mature light chain variable region corresponding to SEQ ID NO:40;
(e) 1415.1.1 having a mature heavy chain variable region corresponding to SEQ ID NO:55 and a mature light chain variable region corresponding to SEQ ID NO:50;
(f) 1749.1.3 having a mature heavy chain variable region corresponding to SEQ ID NO:65 and a mature light chain variable region corresponding to SEQ ID NO:60;
(g) 2120.4.19 having a mature heavy chain variable region corresponding to SEQ ID NO:77 and a mature light chain variable region corresponding to SEQ ID NO:70;
(h) 2107.4.10 having a mature heavy chain variable region corresponding to SEQ ID NO:89 and a mature light chain variable region corresponding to SEQ ID NO:84: and
(i) an antibody comprising CDRs substantially from the monoclonal antibodies 1174.1.3, 1414.1.2, 1415.1.1, 1749.1.3, 2120.4.19, and 2107.4.10. In some such antibodies, the antibody is monoclonal. In some such antibodies, the antibody is chimeric, humanized, veneered, or human.

In some such antibodies, the antibody is not an antibody selected from the group consisting of:
(a) clone 15 having a mature heavy chain variable region corresponding to SEQ ID NO:18 and a mature light chain variable region corresponding to SEQ ID NO:13;
(b) clone 17 having a mature heavy chain variable region corresponding to SEQ ID NO:7 and a mature light chain variable region corresponding to SEQ ID NO:2;
(c) 1174.1.3 having a mature heavy chain variable region corresponding to SEQ ID NO:35 and a mature light chain variable region corresponding to SEQ ID NO:30;
(d) 1414.1.2 having a mature heavy chain variable region corresponding to SEQ ID NO:45 and a mature light chain variable region corresponding to SEQ ID NO:40;
(e) 1415.1.1 having a mature heavy chain variable region corresponding to SEQ ID NO:55 and a mature light chain variable region corresponding to SEQ ID NO:50;
(f) 1749.1.3 having a mature heavy chain variable region corresponding to SEQ ID NO:65 and a mature light chain variable region corresponding to SEQ ID NO:60;

(g) 2120.4.19 having a mature heavy chain variable region corresponding to SEQ ID NO:77 and a mature light chain variable region corresponding to SEQ ID NO:70, 71, or 72;

(h) 2107.4.10 having a mature heavy chain variable region corresponding to SEQ ID NO:89 and a mature light chain variable region corresponding to SEQ ID NO:82 or 84: and (i) an antibody comprising CDRs substantially from the monoclonal antibodies 1174.1.3, 1414.1.2, 1415.1.1, 1749.1.3, 2120.4.19, and 2107.4.10. In some such antibodies, the antibody is monoclonal. In some such antibodies, the antibody is chimeric, humanized, veneered, or human.

The invention further provides a pharmaceutical composition comprising any of the above-mentioned antibodies.

The invention further provides the use of any of the above-mentioned antibodies in the manufacture of a medicament for the treatment of an inflammatory disorder characterized by infiltration of MCAM-expressing cells into a site of inflammation in the body. Such an inflammatory disorder may be a central nervous system (CNS) inflammatory disorder characterized by infiltration of MCAM-expressing cells into the CNS.

The invention further provides the use of any of the above-mentioned antibodies in the manufacture of a medicament for the treatment of multiple sclerosis, Parkinson's disease, allergic contact dermatitis, psoriasis, psoriatic arthritis, rheumatoid arthritis, sarcoidosis, inflammatory bowel disease, Crohn's disease, or cancer (e.g. solid or haematologic tumors), such as melanoma.

The invention further provides a method of treating an inflammatory disorder characterized by infiltration of MCAM-expressing cells to a site of inflammation, the method comprising administering to a mammalian subject in need thereof an effective amount of any of the above-mentioned antibodies. In some methods, the disease is multiple sclerosis, Parkinson's disease, allergic contact dermatitis, psoriasis, psoriatic arthritis, rheumatoid arthritis, sarcoidosis, inflammatory bowel disease, Crohn's disease, or cancer (e.g. solid or haematologic tumors), such as melanoma. In some methods, the MCAM-expressing cells are TH17 cells. In some methods, the mammalian subject is a human. In some of the methods, the antibody inhibits the binding of MCAM to a protein comprising a laminin α-4 chain. In some of the methods, the mammalian subject is a human. In some of the methods, the MCAM-expressing cells are TH17 cells.

The invention further provides an isolated peptide comprising an epitope for binding an anti-MCAM monoclonal antibody, wherein the peptide comprises 5-50 contiguous amino acid residues of human MCAM (SEQ ID NO:11) including amino acid residue 318. In some of these peptides, the peptide is linked to a carrier polypeptide. In some of these peptides, the peptide is combined with an adjuvant.

The invention further provides for a method of generating an antibody that inhibits binding of human MCAM to a laminin α-4 chain, comprising:
  (a) immunizing a subject with a peptide described above;
  (b) isolating B-cells from the subject, wherein the B-cells secrete antibodies;
  (c) screening the antibodies to identify an antibody that inhibits binding of human MCAM to a laminin α-4 chain. In some of the methods, the method further comprises:
  (d) fusing the B-cells with immortalized cells in culture to form monoclonal antibody-producing hybridoma cells;
  (e) culturing the hybridoma cells; and,
  (f) isolating monoclonal antibodies from culture.

BRIEF DESCRIPTION OF THE DRAWINGS

FIG. 3A depicts an alignment of the amino acid sequences of 1749.1.3 with the humanized 1749 light chain mature variable regions (SEQ ID NOS.161 and 160). ABA71407.1 and CAI99800.1 are the human acceptor $V_L$ sequence (SEQ ID NOS.162 and 163). CDR regions according to Kabat definition are highlighted in gray.

FIG. 3B depicts an alignment of the amino acid sequences of 1749.1.3 with the humanized 1749 heavy chain mature variable regions (SEQ ID NOS. 157 and 156). AAX82494.1 and ADX65676.1 are the human acceptor $V_H$ sequence (SEQ ID NOS.158 and 159). CDR regions according to Kabat definition are highlighted in gray.

BRIEF DESCRIPTION OF THE SEQUENCES

Figure 1:
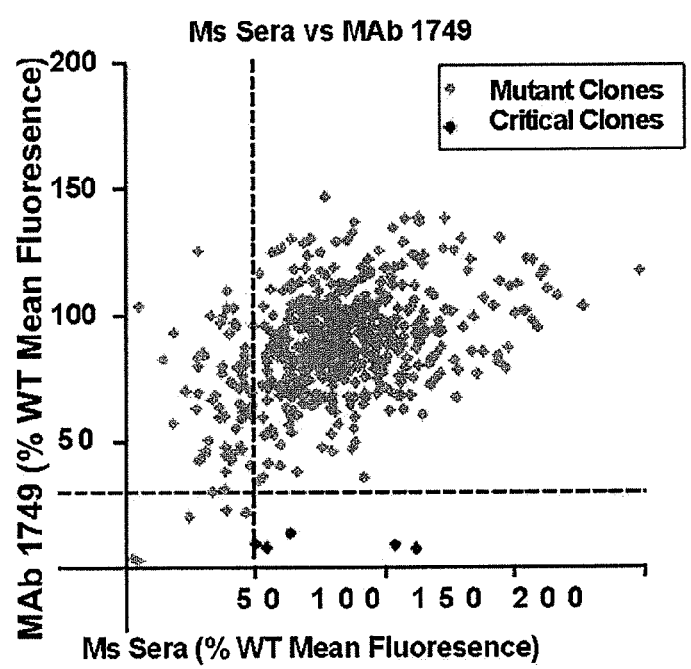
FIG. 1 depicts the identification of critical clones. The mean 1749.1.3 binding value plotted as a function of its mean surface expression value (gray diamonds). Thresholds of <30% monoclonal antibody reactivity and >50% mouse sera binding were applied to identify clones (black diamonds) that were negative for antibody binding but positive for surface expression

SEQ ID NO:1 is the nucleic acid sequence encoding the mature light chain variable region of antibody clone 17.

SEQ ID NO:2 is the amino acid sequence of the mature light chain variable region of antibody clone 17.

SEQ ID NO:3 is the amino acid sequence of CDRL1 of the antibody clone 17.

SEQ ID NO:4 is the amino acid sequence of CDRL2 of the antibody clone 17.

SEQ ID NO:5 is the amino acid sequence of CDRL3 of the antibody clone 17.

SEQ ID NO:6 is the nucleic acid sequence encoding the mature heavy chain variable region of antibody clone 17.

SEQ ID NO:7 is the amino acid sequence of the mature heavy chain variable region of antibody clone 17.

SEQ ID NO:8 is the amino acid sequence of CDRH1 of the antibody clone 17.

SEQ ID NO:9 is the amino acid sequence of CDRH2 of the antibody clone 17.

SEQ ID NO:10 is the amino acid sequence of CDRH3 of the antibody clone 17.

SEQ ID NO:11 is the amino acid sequence of human MCAM Accession No. CAA48332.

SEQ ID NO:12 is the nucleic acid sequence encoding the mature light chain variable region of antibody clone 15.

SEQ ID NO:13 is the amino acid sequence of the mature light chain variable region of antibody clone 15.

SEQ ID NO:14 is the amino acid sequence of CDRL1 of the antibody clone 15.

SEQ ID NO:15 is the amino acid sequence of CDRL2 of the antibody clone 15.

SEQ ID NO:16 is the amino acid sequence of CDRL3 of the antibody clone 15.

SEQ ID NO:17 is the nucleic acid sequence encoding the mature heavy chain variable region of antibody clone 15.

SEQ ID NO:18 is the amino acid sequence of the mature heavy chain variable region of antibody clone 15.

SEQ ID NO:19 is the amino acid sequence of CDRH1 of the antibody clone 15.
SEQ ID NO:20 is the amino acid sequence of CDRH2 of the antibody clone 15.
SEQ ID NO:21 is the amino acid sequence of CDRH3 of the antibody clone 15.
SEQ ID NO:22 is the amino acid sequence of human MCAM domain 1 (residues 19-129).
SEQ ID NO:23 is the amino acid sequence of human MCAM domain 2 (residues 139-242).
SEQ ID NO:24 is the amino acid sequence of human MCAM domain 3 (residues 244-321).
SEQ ID NO:25 is the amino acid sequence of human MCAM domain 4 (residues 355-424).
SEQ ID NO:26 is the amino acid sequence of human MCAM domain 5 (residues 430-510).
SEQ ID NO:27 is the amino acid sequence of an α4-chain isoform of human laminin 411 (Accession No. NP001098676).
SEQ ID NO:28 is the amino acid sequence of an α4-chain isoform of human laminin 411 (Accession No. CAA48332).
SEQ ID NO:29 is the nucleic acid sequence encoding the mature light chain variable region of antibody 1174.1.3.
SEQ ID NO:30 is the amino acid sequence of the mature light chain variable region of antibody 1174.1.3.
SEQ ID NO:31 is the amino acid sequence of CDRL1 of antibody 1174.1.3.
SEQ ID NO:32 is the amino acid sequence of CDRL2 of antibody 1174.1.3.
SEQ ID NO:33 is the amino acid sequence of CDRL3 of antibody 1174.1.3.
SEQ ID NO:34 is the nucleic acid sequence encoding the mature heavy chain variable region of antibody 1174.1.3.
SEQ ID NO:35 is the amino acid sequence of the mature heavy chain variable region of antibody 1174.1.3.
SEQ ID NO:36 is the amino acid sequence of CDRH1 of antibody 1174.1.3.
SEQ ID NO:37 is the amino acid sequence of CDRH2 of antibody 1174.1.3.
SEQ ID NO:38 is the amino acid sequence of CDRH3 of antibody 1174.1.3.
SEQ ID NO:39 is the nucleic acid sequence encoding the mature light chain variable region of antibody 1414.1.2.
SEQ ID NO:40 is the amino acid sequence of the mature light chain variable region of antibody 1414.1.2.
SEQ ID NO:41 is the amino acid sequence of CDRL1 of antibody 1414.1.2.
SEQ ID NO:42 is the amino acid sequence of CDRL2 of antibody 1414.1.2.
SEQ ID NO:43 is the amino acid sequence of CDRL3 of antibody 1414.1.2.
SEQ ID NO:44 is the nucleic acid sequence encoding the mature heavy chain variable region of antibody 1414.1.2.
SEQ ID NO:45 is the amino acid sequence of the mature heavy chain variable region of antibody 1414.1.2.
SEQ ID NO:46 is the amino acid sequence of CDRH1 of antibody 1414.1.2.
SEQ ID NO:47 is the amino acid sequence of CDRH2 of antibody 1414.1.2.
SEQ ID NO:48 is the amino acid sequence of CDRH3 of antibody 1414.1.2.
SEQ ID NO:49 is the nucleic acid sequence encoding the mature light chain variable region of antibody 1415.1.1.
SEQ ID NO:50 is the amino acid sequence of the mature light chain variable region of antibody 1415.1.1.
SEQ ID NO:51 is the amino acid sequence of CDRL1 of antibody 1415.1.1.
SEQ ID NO:52 is the amino acid sequence of CDRL2 of antibody 1415.1.1.
SEQ ID NO:53 is the amino acid sequence of CDRL3 of antibody 1415.1.1.
SEQ ID NO:54 is the nucleic acid sequence encoding the mature heavy chain variable region of antibody 1415.1.1.
SEQ ID NO:55 is the amino acid sequence of the mature heavy chain variable region of antibody 1415.1.1.
SEQ ID NO:56 is the amino acid sequence of CDRH1 of antibody 1415.1.1.
SEQ ID NO:57 is the amino acid sequence of CDRH2 of antibody 1415.1.1.
SEQ ID NO:58 is the amino acid sequence of CDRH3 of antibody 1415.1.1.
SEQ ID NO:59 is the nucleic acid sequence encoding the mature light chain variable region of antibody 1749.1.3.
SEQ ID NO:60 is the amino acid sequence of the mature light chain variable region of antibody 1749.1.3.
SEQ ID NO:61 is the amino acid sequence of CDRL1 of antibody 1749.1.3.
SEQ ID NO:62 is the amino acid sequence of CDRL2 of antibody 1749.1.3.
SEQ ID NO:63 is the amino acid sequence of CDRL3 of antibody 1749.1.3.
SEQ ID NO:64 is the nucleic acid sequence encoding the mature heavy chain variable region of antibody 1749.1.3.
SEQ ID NO:65 is the amino acid sequence of the mature heavy chain variable region of antibody 1749.1.3.
SEQ ID NO:66 is the amino acid sequence of CDRH1 of antibody 1749.1.3.
SEQ ID NO:67 is the amino acid sequence of CDRH2 of antibody 1749.1.3.
SEQ ID NO:68 is the amino acid sequence of CDRH3 of antibody 1749.1.3.
SEQ ID NO:69 is the nucleic acid sequence encoding a mature light chain variable region of antibody 2120.4.19.
SEQ ID NO:70 is the amino acid sequence of the mature light chain variable region of antibody 2120.4.19 set forth in SEQ ID NO:69.
SEQ ID NO:71 is the amino acid sequence of a mature light chain variable region of antibody 2120.4.19.
SEQ ID NO:72 is the amino acid sequence of a mature light chain variable region of antibody 2120.4.19.
SEQ ID NO:73 is the amino acid sequence of CDRL1 of antibody 2120.4.19.
SEQ ID NO:74 is the amino acid sequence of CDRL2 of antibody 2120.4.19.
SEQ ID NO:75 is the amino acid sequence of CDRL3 of antibody 2120.4.19.
SEQ ID NO:76 is the nucleic acid sequence encoding the mature heavy chain variable region of antibody 2120.4.19.
SEQ ID NO:77 is the amino acid sequence of the mature heavy chain variable region of antibody 2120.4.19.
SEQ ID NO:78 is the amino acid sequence of CDRH1 of antibody 2120.4.19.
SEQ ID NO:79 is the amino acid sequence of CDRH2 of antibody 2120.4.19.
SEQ ID NO:80 is the amino acid sequence of CDRH3 of antibody 2120.4.19.
SEQ ID NO:81 is a nucleic acid sequence encoding a mature light chain variable region of antibody 2107.4.10.
SEQ ID NO:82 is the amino acid sequence of the mature light chain variable region of antibody 2107.4.10 set forth in SEQ ID NO:81.
SEQ ID NO:83 is a nucleic acid sequence encoding a mature light chain variable region of antibody 2107.4.10.

SEQ ID NO:84 is the amino acid sequence of the mature light chain variable region of antibody 2107.4.10 set forth in SEQ ID NO:83.

SEQ ID NO:85 is the amino acid sequence of CDRL1 of antibody 2107.4.10.

SEQ ID NO:86 is the amino acid sequence of CDRL2 of antibody 2107.4.10.

SEQ ID NO:87 is the amino acid sequence of CDRL3 of antibody 2107.4.10.

SEQ ID NO:88 is the nucleic acid sequence encoding the mature heavy chain variable region of antibody 2107.4.10.

SEQ ID NO:89 is the amino acid sequence of the mature heavy chain variable region of antibody 2107.4.10.

SEQ ID NO:90 is the amino acid sequence of CDRH1 of antibody 2107.4.10.

SEQ ID NO:91 is the amino acid sequence of CDRH2 of antibody 2107.4.10.

SEQ ID NO:92 is the amino acid sequence of CDRH3 of antibody 2107.4.10.

SEQ ID NO:93 is the amino acid sequence of the mature heavy chain variable region of antibody 1749.1.3.

SEQ ID NO:94 is the amino acid sequence of the mature heavy chain variable region of humanized antibody 1749 version 1 (VH1).

SEQ ID NO:95 is the amino acid sequence of the mature heavy chain variable region of humanized antibody 1749 version 2 (VH2).

SEQ ID NO:96 is the amino acid sequence of the heavy chain variable framework donor U96282_VH.

SEQ ID NO:97 is the amino acid sequence of the mature light chain variable region of antibody 1749.1.3.

SEQ ID NO:98 is the amino acid sequence of the mature light chain variable region of humanized antibody 1749 version 1 (VL1).

SEQ ID NO:99 is the amino acid sequence of the mature light chain variable region of humanized antibody 1749 version 2 (VL2).

SEQ ID NO:100 is the amino acid sequence of the light chain variable framework donor X02990_VL.

SEQ ID NO:101 is the amino acid sequence of the mature heavy chain variable region of antibody 2107.4.10.18.

SEQ ID NO:102 is the amino acid sequence of the mature heavy chain variable region of humanized antibody 2107 version 1 (VH1).

SEQ ID NO:103 is the amino acid sequence of the mature heavy chain variable region of humanized antibody 2107 version 2 (VH2).

SEQ ID NO:104 is the amino acid sequence of the mature heavy chain variable region of humanized antibody 2107 version 3 (VH3).

SEQ ID NO:105 is the amino acid sequence of the mature heavy chain variable region of humanized antibody 2107 version 4A (VH4A).

SEQ ID NO:106 is the amino acid sequence of the mature heavy chain variable region of humanized antibody 2107 version 5A (VH5A).

SEQ ID NO:107 is the amino acid sequence of the mature heavy chain variable region of humanized antibody 2107 version 6 (VH6).

SEQ ID NO:108 is the amino acid sequence of the heavy chain variable framework donor AF062133_VH.

SEQ ID NO:109 is the amino acid sequence of the mature light chain variable region of antibody 2107.4.10.18.

SEQ ID NO:110 is the amino acid sequence of the mature light chain variable region of humanized antibody 2107 version 1 (VL1).

SEQ ID NO:111 is the amino acid sequence of the mature light chain variable region of humanized antibody 2107 version 2 (VL2).

SEQ ID NO:112 is the amino acid sequence of the mature light chain variable region of humanized antibody 2107 version 3 (VL3).

SEQ ID NO:113 is the amino acid sequence of the light chain variable framework donor U86803.

SEQ ID NO:114 is the amino acid sequence of the mature heavy chain variable region of antibody 2120.4.19.6.

SEQ ID NO:115 is the amino acid sequence of the mature heavy chain variable region of humanized antibody 2120 version 1 (VH1).

SEQ ID NO:116 is the amino acid sequence of the mature heavy chain variable region of humanized antibody 2120 version 2 (VH2).

SEQ ID NO:117 is the amino acid sequence of the mature heavy chain variable region of humanized antibody 2120 version 3 (VH3).

SEQ ID NO:118 is the amino acid sequence of the mature heavy chain variable region of humanized antibody 2120 version 4 (VH4).

SEQ ID NO:119 is the amino acid sequence of the mature heavy chain variable region of humanized antibody 2120 version 5 (VH5).

SEQ ID NO:120 is the amino acid sequence of the mature light chain variable region of antibody 2120.4.19.6.

SEQ ID NO:121 is the amino acid sequence of the mature light chain variable region of humanized antibody 2120 version 1 (VL1).

SEQ ID NO:122 is the amino acid sequence of the mature light chain variable region of humanized antibody 2120 version 2 (VL2).

SEQ ID NO:123 is the amino acid sequence of the mature light chain variable region of humanized antibody 2120 version 3 (VL3).

SEQ ID NO:124 is the amino acid sequence of the light chain variable framework donor X84343_VL.

SEQ ID NO:125 is the amino acid sequence of a humanized heavy chain framework region.

SEQ ID NO:126 is the amino acid sequence of a humanized heavy chain framework region.

SEQ ID NO:127 is the amino acid sequence of a humanized heavy chain framework region.

SEQ ID NO:128 is the amino acid sequence of a humanized heavy chain/light chain framework region.

SEQ ID NO:129 is the amino acid sequence of a humanized light chain framework region.

SEQ ID NO:130 is the amino acid sequence of a humanized light chain framework region.

SEQ ID NO:131 is the amino acid sequence of a humanized light chain framework region.

SEQ ID NO:132 is the amino acid sequence of a humanized light chain framework region.

SEQ ID NO:133 is the amino acid sequence of a humanized heavy chain framework region.

SEQ ID NO:134 is the amino acid sequence of a humanized heavy chain framework region.

SEQ ID NO:135 is the amino acid sequence of a humanized heavy chain framework region.

SEQ ID NO:136 is the amino acid sequence of a humanized heavy chain framework region.

SEQ ID NO:137 is the amino acid sequence of a humanized heavy chain framework region.

SEQ ID NO:138 is the amino acid sequence of a humanized heavy chain framework region.

SEQ ID NO:139 is the amino acid sequence of CDRH1 of humanized antibody 2120 version 3 (VH3).

SEQ ID NO:140 is the amino acid sequence of CDRH1 of humanized antibody 2120 version 4 (VH4).

SEQ ID NO:141 is the amino acid sequence of CDRH1 of humanized antibody 2120 version 5 (VH5).

SEQ ID NO:142 is the amino acid sequence of a humanized light chain framework region.

SEQ ID NO:143 is the amino acid sequence of a humanized light chain framework region.

SEQ ID NO:144 is the amino acid sequence of a humanized light chain framework region.

SEQ ID NO:145 is the amino acid sequence of a humanized light chain framework region.

SEQ ID NO:146 is the amino acid sequence of a humanized light chain framework region.

SEQ ID NO:147 is the amino acid sequence of a humanized light chain framework region.

SEQ ID NO:148 is the amino acid sequence of a humanized light chain framework region.

SEQ ID NO:149 is the amino acid sequence of a humanized light chain framework region.

SEQ ID NO:150 is the amino acid sequence of a humanized light chain framework region.

SEQ ID NO:151 is the amino acid sequence of CDRH1 of humanized antibody 2107 version 1 (VH1).

SEQ ID NO:152 is the amino acid sequence of CDRH1 of humanized antibody 2107 version 4 (VH4).

SEQ ID NO:153 is the amino acid sequence of CDRH3 of humanized antibody 2120 version 1-5 (VH1-VH5).

SEQ ID NO:154 is the amino acid sequence of a humanized light chain framework region.

SEQ ID NO:155 is the amino acid sequence of a humanized heavy chain framework region.

SEQ ID NO:156 is the amino acid sequence of the mature heavy chain variable region of humanized antibody 1749 version 3 (VH3).

SEQ ID NO:157 is the amino acid sequence of the mouse heavy chain variable region structure template PBD#1HILVH.

SEQ ID NO:158 is the amino acid sequence of the heavy chain variable acceptor framework ACC#AAX82494.1.

SEQ ID NO:159 is the amino acid sequence of the heavy chain variable acceptor framework ACC#ADX65676.1.

SEQ ID NO:160 is the amino acid sequence of the mature light chain variable region of humanized antibody 1749 version 3 (VL3).

SEQ ID NO:161 is the amino acid sequence of the mouse light chain variable region structure template PDB#2LTQVL.

SEQ ID NO:162 is the amino acid sequence of the light chain variable acceptor framework ACC#ABA71407.1.

SEQ ID NO:163 is the amino acid sequence of the light chain variable acceptor framework CAI99800.1.

SEQ ID NO:164 is the nucleic acid sequence encoding an exemplary signal peptide that can be fused to a mature heavy chain or mature light chain variable region.

SEQ ID NO:165 is the amino acid sequence of the exemplary signal peptide encoded by the nucleic acid sequence of SEQ ID NO:164.

SEQ ID NO:166 is the nucleic acid sequence encoding an exemplary signal peptide that can be fused to a mature heavy chain or mature light chain variable region.

SEQ ID NO:167 is the amino acid sequence of the exemplary signal peptide encoded by the nucleic acid sequence of SEQ ID NO:166.

SEQ ID NO:168 is the nucleic acid sequence encoding an exemplary signal peptide that can be fused to a mature heavy chain or mature light chain variable region.

SEQ ID NO:169 is the amino acid sequence of the exemplary signal peptide encoded by the nucleic acid sequence of SEQ ID NO:168.

SEQ ID NO:170 is the amino acid sequence of a humanized 1749 light chain constant region, with Arginine at the N-terminus.

SEQ ID NO:171 is the amino acid sequence of a humanized 1749 light chain constant region, without Arginine at the N-terminus.

SEQ ID NO:172 is the amino acid sequence of a humanized 1749 heavy chain constant region.

SEQ ID NO:173 is the amino acid sequence of a BIP version heavy chain G1m3 allotype constant region.

SEQ ID NO:174 is the amino acid sequence of a BIP version heavy chain G1m3 allotype constant region.

SEQ ID NO:175 is the amino acid sequence of a mature light chain region of humanized antibody 1749 version 3 (VL3+light chain constant region).

SEQ ID NO:176 is the amino acid sequence of a mature heavy chain region of humanized antibody 1749 version 3 (VH3+BIP version heavy chain G1m3 allotype constant region).

SEQ ID NO:177 is the amino acid sequence of a mature heavy chain region of humanized antibody 1749 version 3 (VH3+BIP version heavy chain G1m3 allotype constant region).

SEQ ID NO:178 is the amino acid sequence of the mature heavy chain variable region of humanized antibody 2107 version 4B (VH4B).

SEQ ID NO:179 is the amino acid sequence of the mature heavy chain variable region of humanized antibody 2107 version 5B (VH5B).

DEFINITIONS

Monoclonal antibodies are typically provided in isolated form. This means that an antibody is typically at least 50% w/w pure of proteins and other macromolecules arising from its production or purification but does not exclude the possibility that the monoclonal antibody is combined with an excess of pharmaceutical acceptable carrier(s) or other vehicle intended to facilitate its use. Sometimes monoclonal antibodies are at least 60%, 70%, 80%, 90%, 95 or 99% w/w pure of proteins and other macromolecules from production or purification.

Specific binding of a monoclonal antibody to its target antigen means an affinity of at least $10^6$, $10^7$, $10^8$, $10^9$, or $10^{10}$ M$^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that a monoclonal antibody binds one and only one target.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region means a light chain variable region without the light chain signal peptide. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. (See generally, Fundamental Immunology (Paul, W., ed., 2nd ed. Raven Press, N.Y., 1989, Ch. 7, incorporated by reference in its entirety for all purposes).

The mature variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md., 1987 and 1991), or Chothia & Lesk, J. Mol. Biol. 196:901-917 (1987); Chothia et al., Nature 342:878-883 (1989). Kabat also provides a widely used numbering convention (Kabat numbering) in which corresponding residues between different heavy chains or between different light chains are assigned the same number (e.g., H83 means position 83 by Kabat numbering in the mature heavy chain variable region; likewise position L36 means position 36 by Kabat numbering in the mature light chain variable region). Kabat numbering is used throughout in referring to positions in the variable region of an antibody unless explicitly stated otherwise.

The term "antibody" includes intact antibodies and antigen binding fragments thereof. Typically, fragments compete with the intact antibody from which they were derived for specific binding to the target including separate heavy chains, light chains Fab, Fab', F(ab')$_2$, F(ab)c, diabodies, Dabs, nanobodies, and Fv. Fragments can be produced by recombinant DNA techniques, or by enzymatic or chemical separation of intact immunoglobulins.

The term "antibody" also includes a bispecific antibody, and/or a chimeric antibody, and/or a humanized antibody. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol. 148:1547-53 (1992)). In some bispecific antibodies, the two different heavy/light chain pairs may include a humanized heavy chain/light chain pair and a heavy chain/light chain pair specific for a different epitope.

In some bispecific antibodies, one heavy chain light chain pair is a humanized antibody as further disclosed below and the heavy light chain pair is from an antibody that binds to a receptor expressed on the blood brain barrier, such as an insulin receptor, an insulin-like growth factor (IGF) receptor, a leptin receptor, or a lipoprotein receptor, or a transferrin receptor (Friden et al., PNAS 88:4771-4775, 1991; Friden et al., Science 259:373-377, 1993). Such a bispecific antibody can be transferred cross the blood brain barrier by receptor-mediated transcytosis. Brain uptake of the bispecific antibody can be further enhanced by engineering the bi-specific antibody to reduce its affinity to the blood brain barrier receptor. Reduced affinity for the receptor resulted in a broader distribution in the brain (see, e.g., Atwal. et al. Sci. Trans. Med. 3, 84ra43, 2011; Yu et al. Sci. Trans. Med. 3, 84ra44, 2011).

Exemplary bispecific antibodies can also be (1) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (2) a Tandab, which is a fusion of two single chain diabodies resulting in a tetravalent bispecific antibody that has two binding sites for each of the target antigens; (3) a flexibody, which is a combination of scFvs with a diabody resulting in a multivalent molecule; (4) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (5) a so-called Scorpion molecule, comprising, e.g., two scFvs fused to both termini of a human Fc-region. Examples of platforms useful for preparing bispecific antibodies include but are not limited to BiTE (Micromet), DART (MacroGenics), Fcab and Mab2 (F-star), Fc-engineered IgG1 (Xencor) or DuoBody (based on Fab arm exchange, Genmab).

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

An "antagonist" antibody or other binding agent is one which inhibits a biological activity of the antigen it binds. Such antibodies may substantially or completely inhibit the biological activity of the antigen.

The terms "biological activity" and "biologically active" with regard to MCAM refer to its ability to specifically bind its ligand (a laminin α4 chain, e.g., the α4 chain of laminin 411) and/or to facilitate the infiltration of MCAM-expressing cells, e.g., TH17 cells, into the CNS.

"Inhibit" means an agent decreases the biological activity of at least one target, for example MCAM. Such an inhibitor inhibits the activity of at least one target by at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 95% or at least about 100%.

A "subject" includes a human or other mammalian subject that receives either prophylactic or therapeutic treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" one or more recited elements may include other elements not specifically recited. For example, a composition that comprises an antibody may contain the antibody alone or in combination with other ingredients.

Designation of a range of values includes all integers within or defining the range, and all subranges defined by integers within the range.

Unless otherwise apparent from the context, the term "about" encompasses values within a standard margin of error of measurement (SEM) of a stated value.

Statistical significance means p≤0.05.

DETAILED DESCRIPTION

I. General

Antibodies with the useful property of inhibiting MCAM binding to the laminin α4 chain of laminin 411 are disclosed in WO/2012/170071 and PCT/US2013/058773. The present application among other things (a) provides new humanized forms of the 1749.1.3 antibody, (b) maps the epitopes to which the 1749.1.3 antibody binds, and (c) provides antibodies binding to the same epitope.

The terms "1749.1.3", "m1749", or "mouse 1749" antibody refer to a mouse derived monoclonal antibody clone having a mature variable heavy chain corresponding to SEQ ID NO:93 and a mature variable light chain corresponding to SEQ ID NO:97. "Humanized 1749" or "hu1749" refers humanized variants of the 1749.1.3 clone. The humanized variant of 1749 having a mature heavy chain variable region corresponding to SEQ ID NO:156 and a mature light chain variable region corresponding to SEQ ID NO:160 is referred to herein as "hu1749VH3VL3".

II. Target Molecules

Natural human wildtype MCAM (melanoma cell adhesion molecule, also known as CD146 and MUC18) is a peptide of 646 amino acids having the following amino acid sequence:

```
                                              (SEQ ID NO: 11)
MGLPRLVCAFLLAACCCCPRVAGVPGEAEQPAPELVEVEVGSTALLKC

GLSQSQGNLSHVDWFSVHKEKRTLIFTVRQGQGQSEPGEYEQRLSLQD

RGATLALTQVTPQDERIFLCQGKRPRSQEYRIQLRVYKAPEEPNIQVN

PLGIPVNSKEPEEVATCVGRNGYPIPQVIWYKNGRPLKEEKNRVHIQS
```

-continued
```
SQTVESSGLYTLQSILKAQLVKEDKDAQFYCELNYRLPSGNHMKESRE

VTVPVFYPTEKVWLEVEPVGMLKEGDRVEIRCLADGNPPHFSISKQNP

STREAEEETTNDNGVLVLEPARKEHSGRYECQAWNLDTMISLLSEPQE

LLVNYVSDVRVSPAAPERQEGSSLTLTCEAESSQDLEFQWLREETDQV

LERGPVLQLHDLKREAGGGYRCVASVPSIPGLNRTQLVKLAIFGPPWM

AFKERKVWVKENMVLNLSCEASGHPRPTISWNVNGTASEQDQDPQRVL

STLNVLVTPELLETGVECTASNDLGKNTSILFLELVNLTTLTPDSNTT

TGLSTSTASPHTRANSTSTERKLPEPESRGVVIVAVIVCILVLAVLGA

VLYFLYKKGKLPCRRSGKQEITLPPSRKTELVVEVKSDKLPEEMGLLQ

GSSGDKRAPGDQGEKYIDLRH.
```

(GenBank database under Accession Number AAA20922.1 (CAA48332). MCAM is a cell surface glycoprotein belonging to the immunoglobulin superfamily involved in cell adhesion, and in cohesion of the endothelial monolayer at intercellular junctions in vascular tissue. It also promotes tumor progression of many cancers, such as solid tumors, including melanoma and prostate cancer. It is known to interact in a homotypic/homophilic manner and may also bind to other ligands. The human MCAM includes five immunoglobulin domains (1: amino acid residues 19-129; 2: amino acid residues 139-242; 3: amino acid residues 244-321; 4: amino acid residues 335-424; and 5: amino acid residues 430-510), shown as SEQ ID NOs:22-26.

Unless otherwise apparent from the context, reference to MCAM or its fragments includes the natural human wild-type amino acid sequences indicated above, and human allelic variants thereof.

Laminin α4 refers to one of the polypeptide chains found in laminin molecules, which are expressed in the basal lamina (of the basement membrane), a protein network foundation for most cells and organs. Laminins are known to bind to cell membranes through plasma membrane molecules and contribute to cell attachment. The laminin α4 chain typically forms a complex with a laminin β-chain, and a laminin γ-chain. The laminin α4 chain is found in numerous laminin molecules including laminin 411 (laminin 8 or α4β1γ1); laminin 421 (laminin 9 or α4β2γ1), and laminin 423 (laminin 14 or α4β2γ3). There are two main isoforms of the human laminin α4-chain: GenBank Accession Nos. NP001098676 and CAA48332 (SEQ ID NOs:27 and 28). "Laminin 411" refers to a trimeric polypeptide complex made up of three polypeptide subunits or chains: α4-chain, a β1-chain, and a γ1-chain.

Antagonist against MCAM include antibodies, fusion proteins of receptors or ligands to an IgG constant region other biologic binding molecules, and small molecules. Antibodies can be monoclonal or polyclonal. Antibodies can be nonhuman, such as mouse or rat, nonhuman primate or can be human Antibodies can be chimeric, veneered, humanized, primatized and the like.

An MCAM antagonist refers to an antagonist that fully or partially inhibits the ability of MCAM (i) to specifically bind its ligand: a laminin α4 chain, e.g., the α4 chain of laminin 411; and/or (ii) to facilitate an MCAM-expressing cell, e.g., a TH17 cell, to infiltrate into or migrate to a subject's tissue. MCAM antagonists include antibodies or other antagonists binding to MCAM or to its ligand laminin alpha 4.

III. Antibodies

A. Humanized Forms of Anti-MCAM Antibody 1749

A humanized antibody is a genetically engineered antibody in which the CDRs from a non-human "donor" antibody are grafted into human "acceptor" antibody sequences (see, e.g., Queen et al., U.S. Pat. Nos. 5,530,101 and 5,585,089; Winter et al., U.S. Pat. No. 5,225,539; Carter, U.S. Pat. No. 6,407,213; Adair, U.S. Pat. Nos. 5,859,205 and 6,881,557; and Foote, U.S. Pat. No. 6,881,557). The acceptor antibody sequences can be, for example, a mature human antibody variable region sequence, a composite of such sequences, a consensus sequence of human antibody variable region sequences (e.g., light and heavy chain variable region consensus sequences of Kabat, 1991, supra), or a germline variable region sequence.

Examples of an acceptor sequence for the heavy chain are the human mature heavy chain variable regions with NCBI accession codes AAX82494.1 (GI:62421461) and/or ADX65676.1 (GI:323432073). Preferably a composite of these acceptors is used, as is the case in the present examples. These acceptor sequences include two CDRs having the same canonical form and the same length CDR-H3 with a kinked base as m1749 heavy chain and AAX82494.1 has a 91% sequence identity and ADX65676.1 has an 83% sequence identity in the heavy chain variable region framework. For the light chain, examples of an acceptor sequence are the light chain mature variable regions with NCBI accession codes ABA71407.1 (GI:77379502) and/or CAI99800.1 (GI:98956324). Preferably a composite of these sequences is used, as is the case in the present examples. These acceptor sequences include three CDRs having the same canonical form as a m1749 light chain and ABA71407.1 has an 85% sequence identity and CAI99800.1 has an 83% sequence identity in the light chain variable region framework.

The invention provides humanized antibodies having three light chain and three heavy chain CDRs as defined by Kabat entirely or substantially from the donor m1749 antibody and mature variable region framework sequences and constant regions, if present, entirely or substantially from human antibody sequences. Likewise a humanized heavy chain is a heavy chain having three heavy chain CDRs as defined by Kabat entirely or substantially from the heavy chain of the m1749 antibody, and a mature heavy chain variable sequence and heavy chain constant region sequence, if present, entirely or substantially from human antibody heavy chain sequence. Likewise a humanized light chain is a light chain having three light chain CDRs as defined by Kabat entirely or substantially from the light chain of the m1749 antibody, and a mature light chain variable sequence and light chain constant region sequence, if present, entirely or substantially from human antibody light chain sequence. Some antibodies comprise a humanized heavy chain comprising Kabat CDR1 of SEQ ID NO:66; SYIMS; Kabat CDR2 of SEQ ID NO:67: TISSGGSSTYYPDSVKG; Kabat CDR3 of SEQ ID NO:68: DDDYDVKVFAY. Some antibodies comprise a humanized light chain comprising Kabat CDR1 of SEQ ID NO:61: KSSRSLLNSRIRKNYLA; Kabat CDR2 of SEQ ID NO:62: WASTRES; Kabat CDR3 of SEQ ID NO:63: KQSYNLLT. Some antibodies comprise a humanized heavy chain comprising the three Kabat CDRs of SEQ ID NOs:66, 67, and 68, and a humanized light chain comprising the three Kabat CDRs of SEQ ID NOs:61, 62, and 63. A CDR is substantially from m1749 if at least 85%, 90%, 95%, 96%, 97%, 98%, 99% or 100% of residues are identical to the corresponding residues in the corresponding CDR of m1749 except for CHRH2 Kabat positions 60-65 can be substituted. The mature variable region framework sequences of an antibody chain or the constant region sequence of an antibody chain are substantially from a human mature variable region framework sequence or human constant region sequence respectively when at least 85%, 90%, 95%, 96%, 97%, 98%, 99% or 100% of corresponding residues defined by Kabat are identical.

Certain amino acids from the human mature variable region framework residues can be selected for substitution based on their possible influence on CDR conformation and/or binding to antigen, mediating interaction between heavy and light chains, interaction with the constant region, being a site for desired or undesired post-translational modification, being an unusual residue for its position in a human variable region sequence and therefore potentially immunogenic, among other reasons. The following six variable region framework positions were considered as candidates for substitutions for one or more of these reasons as further specified in the Examples (D9S, A19V, P43S, Q3K, G42E, A93T).

Here as elsewhere, the first-mentioned residue is the residue of a humanized antibody formed by grafting Kabat CDRs into a human acceptor framework, and the second-mentioned residue is a residue being considered for replacing such residue. Thus within variable region frameworks, the first mentioned residue is human and within CDRs the first mentioned residue is mouse (e.g., C97S).

Amino acid substitutions can be made in the CDRs. One possible variation is to substitute certain residues in the CDRs of the m1749 antibody with corresponding residues from human CDRs sequences, typically from the CDRs of the human acceptor sequences used in designing the exemplified humanized antibodies. In some antibodies only part of the CDRs, namely the subset of CDR residues required for binding, termed the SDRs, are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (Chothia, J. Mol. Biol. 196:901, 1987), by molecular modeling and/or empirically, or as described in Gonzales et al., Mol. Immunol. 41:863, 2004. In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

One reason for performing a substitution within a CDR is that a mouse residue is a site of posttranslational modification that may interfere with expression or assembly of an antibody.

The invention provides variants of the humanized 1749 antibody in which the humanized heavy chain mature variable region shows at least 90%, 95%, 96%, 97%, 98% or 99% identity to SEQ ID NO:156 and the humanized light chain mature variable region shows at least 90%, 95%, 96%, 97%, 98% or 99% sequence identity to SEQ ID NO:160. Some such humanized antibodies include three heavy and three light chain CDRs entirely or substantially identical to the CDR regions of hu1749, which are the same as those of the mouse donor antibody. The CDR regions can be defined by any conventional definition (e.g., Chothia) but are preferably as defined by Kabat.

The humanized 1749 antibody in which the humanized heavy chain mature variable region is SEQ ID NO:156 and the humanized light chain mature variable region is SEQ ID NO:160 is referred to as 1749VH3VL3. Some variants of the humanized 1749VH3VL3 antibody retain some or all of the backmutations in hu1749VH3VL3. In other words, at least 1, 2, 3, 4, 5, or preferably all 6 of the following are present: H3 is occupied by K, H42 is occupied by E, H93 is occupied by T, L9 is occupied by S, L19 is occupied by V, and L43 is occupied by S.

In addition to retaining at least 1, 2, 3, 4, 5, or preferably all 6 of the backmutations of hu1749VH3VL3, humanized 1749 antibodies may also contain additional backmutations in the variable region frameworks. Examples of such backmutations include H1 occupied by D, H10 occupied by D, H13 occupied by K, H19 occupied by K, H113 occupied by A, L5 occupied by S, L15 occupied by A, L18 occupied by K, L21 occupied by M, L63 occupied by T, L78 occupied by V, L83 occupied by L, L100 occupied by A, L104 occupied by L, and/or L106 occupied by L. For selection of backmutations for a therapeutic or diagnostic product, one should take into account the degree to which they in general do not improve affinity and the degree to which introducing more mouse residues may give increased risk of immunogenicity.

In any of the above antibodies, other amino acid substitutions can be made in the mature variable region framework, for example, in residues not in contact with the CDRs. Often the replacements made in the variant humanized sequences are conservative with respect to the replaced amino acids.

B. Selection of Constant Region

The heavy and light chain variable regions of chimeric, veneered or humanized antibodies can be linked to at least a portion of a human constant region. The choice of constant region depends, in part, whether antibody-dependent cell-mediated cytotoxicity, antibody dependent cellular phagocytosis and/or complement dependent cytotoxicity are desired. For example, human isotopes IgG1 and IgG3 have complement-dependent cytotoxicity and human isotypes IgG2 and IgG4 do not. Human IgG1 and IgG3 also induce stronger cell mediated effector functions than human IgG2 and IgG4. Light chain constant regions can be lambda or kappa.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). Exemplary substitutions include a Gln at position 250 and/or a Leu at position 428 (EU numbering is used in this paragraph for the constant region) for increasing the half-life of an antibody. Substitution at any or all of positions 234, 235, 236 and/or 237 reduces affinity for Fcγ receptors, particularly FcγRI receptor (see, e.g., U.S. Pat. No. 6,624,821). An alanine substitution at positions 234, 235, and 237 of human IgG1 can be used for reducing effector functions. Some antibodies have alanine substitution at positions 234, 235 and 237 of human IgG1 for reducing effector functions. Optionally, positions 234, 236 and/or 237 in human IgG2 are substituted with alanine and position 235 with glutamine (see, e.g., U.S. Pat. No. 5,624,821). In some antibodies, a mutation at one or more of positions 241, 264, 265, 270, 296, 297, 322, 329, and 331 by EU numbering of human IgG1 is used. In some antibodies, a mutation at one or more of positions 318, 320, and 322 by EU numbering of human IgG1 is used. In some antibodies, positions 234 and/or 235 are substituted with alanine and/or position 329 is substituted with glycine. In some antibodies, positions 234 and 235 are substituted with alanine, such as in SEQ ID NO:174. In some antibodies, the isotype is human IgG2 or IgG4. An exemplary human light chain kappa constant region has the amino acid sequence of SEQ ID NO:170. The N-terminal arginine of SEQ ID NO:170 can be omitted, in which case light chain kappa constant region has the amino acid sequence of SEQ ID NO:171. An exemplary human IgG1 heavy chain constant region has the amino acid sequence of SEQ ID NO:172 (with or without the C-terminal lysine). Antibodies can be expressed as tetramers containing two light and two heavy chains, as separate heavy chains, light chains, as Fab, Fab', F(ab')2, and Fv, or as single chain antibodies in which heavy and light chain mature variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype bind to a non-polymorphic region of a one or more other isotypes. Thus, for example, another heavy chain constant region is of IgG1 G1m3 allotype and has the amino acid sequence of SEQ ID NO:173. Another heavy chain constant region has the amino acid sequence of SEQ ID NO:173 except that it lacks the C-terminal lysine. Another heavy chain constant region has the amino acid sequence of SEQ ID NO:174. Yet another heavy chain constant region has the amino acid sequence of SEQ ID NO:174 except that it lacks the C-terminal lysine.

The invention further provides nucleic acids encoding any of the above constant regions. Optionally, such nucleic acids further encode a signal peptide and can be expressed with the signal peptide linked to the constant region.

C. Expression of Recombinant Antibodies

Antibodies can be produced by recombinant expression. Nucleic acids encoding the antibodies can be codon-optimized for expression in the desired cell-type (e.g., CHO or Sp2/0). Recombinant nucleic acid constructs typically include an expression control sequence operably linked to the coding sequences of antibody chains, including naturally-associated or heterologous promoter regions. The expression control sequences can be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies. The vector or vectors encoding the antibody chains can also contain a selectable gene, such as dihydrofolate reductase, to allow amplification of copy number of the nucleic acids encoding the antibody chains.

*E. coli* is a prokaryotic host particularly useful for expressing antibodies, particularly antibody fragments. Microbes, such as yeast are also useful for expression.

*Saccharomyces* is an example of a yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilizations.

Mammalian cells can be used for expressing nucleotide segments encoding immunoglobulins or fragments thereof. See Winnacker, From Genes to Clones, (VCH Publishers, NY, 1987). A number of suitable host cell lines capable of secreting intact heterologous proteins have been developed in the art, and include CHO cell lines, various COS cell lines, HeLa cells, HEK293 cells, L cells, and non-antibody-producing myelomas including Sp2/0 and NS0. It can be advantageous to use nonhuman cells. Expression vectors for these cells can include expression control sequences, such as an origin of replication, a promoter, an enhancer (Queen et al., Immunol. Rev. 89:49 (1986)), and necessary processing information sites, such as ribosome binding sites, RNA splice sites, polyadenylation sites, and transcriptional terminator sequences. Suitable expression control sequences are promoters derived from endogenous genes, cytomegalovirus, SV40, adenovirus, bovine papillomavirus, and the like. See Co et al., J. Immunol. 148:1149 (1992).

Having introduced vector(s) encoding antibody heavy and light chains into cell culture, cell pools can be screened for growth productivity and product quality in serum-free media. Top-producing cell pools can then be subjected to FACS-based single-cell cloning to generate monoclonal lines. Specific productivities above 50 pg or 100 pg per cell per day, which correspond to product titers of greater than 7.5 g/L culture, can be advantageous. Antibodies produced by single cell clones can also be tested for turbidity, filtration properties, PAGE, IEF, UV scan, HP-SEC, carbohydrate-oligosaccharide mapping, mass spectrometry, and binding assay, such as ELISA or Biacore. A selected clone can then be banked in multiple vials and stored frozen for subsequent use.

Once expressed, antibodies can be purified according to standard procedures of the art, including protein A capture, column chromatography (e.g., hydrophobic interaction or ion exchange), low-pH for viral inactivation and the like (see generally, Scopes, Protein Purification (Springer-Verlag, NY, 1982)).

Methodology for commercial production of antibodies including codon optimization, selection of promoters, transcription elements, and terminators, serum-free single cell cloning, cell banking, use of selection markers for amplification of copy number, CHO terminator, serum free single cell cloning, improvement of protein titers (see, e.g., U.S. Pat. Nos. 5,786,464, 5,888,809, 6,063,598, 6,114,148, 7,569,339, WO2004/050884, WO2005/019442, WO2008/012142, WO2008/012142, WO2008/107388, and WO2009/027471).

D. Nucleic Acids

The invention further provides nucleic acids encoding any of the heavy and light chains described above. Typically, the nucleic acids also encode a signal peptide fused to the mature heavy and light chains (e.g., signal peptides having amino acid sequences of SEQ ID NOs:165, 167, and 169 that can be encoded by SEQ ID NOs:164, 166, and 168). Coding sequences on nucleic acids can be in operable linkage with regulatory sequences to ensure expression of the coding sequences, such as a promoter, enhancer, ribosome binding site, transcription termination signal and the like. The nucleic acids encoding heavy and light chains can occur in isolated form or can be cloned into one or more vectors. The nucleic acids can be synthesized by for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

E. Characterization of MCAM Epitopes for Antibody Binding and Production of Antibodies That Bind the Same 1. MCAM Epitopes for Antibody Binding The invention provides monoclonal antibodies that bind to specific epitopes within the human MCAM protein. Some antibodies of the invention bind to the same or overlapping epitope as antibody designated 1749.1.3 (m1749).

The invention provides antibodies that bind to the same or overlapping epitope as antibody designated m1749. Mutations at residues 272, 318, 320, 340, and 377 of MCAM disrupts specific binding of m1749 (e.g., <30% binding to mutant MCAM compared to a positive control wild type MCAM as described as the examples). Because relatively few residues affect binding and the residues are spaced more broadly than a typical linear epitope (e.g., 3-20 contiguous amino acids), these results provide an indication that m1749 binds to a conformational epitope. Alternatively, one or more of the residues affecting binding may do so allosterically without direct contact with the antibody.

Antibodies binding to an epitope including one or more of residues 272, 318, 320, 324, 326, 340, and 377 of MCAM, and particularly to an epitope including one or more of residues 318, 324, and 326, are likely to share useful inhibitory properties with m1749. Thus, antibodies whose specific binding is inhibited by mutagenesis of one or more or residues 318, 324, and 326 and particularly residue 318 of MCAM are likely to share similar properties to m1749. Some such antibodies bind to an epitope that includes or consists of residue 318, 324, and/or 326 of MCAM. The epitope can be linear, such as an epitope (e.g., 2-5, 3-5, 3-10, 3-15, 3-20, 5-10, 5-15, 5-20, 5-30, 5-40, 5-50, 5-60, or 5-70 contiguous amino acids) including 1, 2, or 3 of the specified amino acids (318, 324, and 326) or be conformational including or consisting of 1, 2, or 3 of the specified amino acids.

2. The Generation of Antibodies that Bind Specific MCAM Epitopes

Some antibodies of the invention bind to the same or overlapping epitope as the m1749 antibody. The production of other non-human monoclonal antibodies, e.g., murine, guinea pig, primate, rabbit or rat, against human MCAM can be accomplished by, for example, immunizing the animal with human MCAM or a peptide fragment thereof including the desired epitope (the "immunogen"), and screening resulting antibodies for binding to MCAM, optionally in competition with m1749 (See Harlow & Lane, *Antibodies, A Laboratory Manual* (CSHP NY, 1988) incorporated by reference for all purposes). Optionally, the immunogen is conjugated to carrier molecule. Optionally, the immunogen is administered with an adjuvant. Several types of adjuvant can be used as described below. Complete Freund's adjuvant followed by incomplete adjuvant is preferred for immunization of laboratory animals. Rabbits or guinea pigs are typically used for making polyclonal antibodies. Mice are typically used for making monoclonal antibodies. Antibodies are screened for specific binding to a desired epitope within MCAM.

The invention provides peptide fragments of MCAM that are used to create antibodies directed to the above described epitopes. Examples of such peptides include a peptide that is between 2-5, 3-5, 3-10, 3-15, 3-20, 5-10, 5-15, 5-20, 5-30, 5-40, 5-50, 5-60, or 5-70 contiguous amino acids in length and includes at least one of amino acids residues 318, 324, and 326 of MCAM. In some of these peptides, the peptide includes all three of amino acid residue 318, 324, and 326.

Immunogens may be conjugated to carrier molecules, typically a carrier polypeptide, and thus help elicit an immune response against the fragment conjugated to the carrier. A single agent can be linked to a single carrier, multiple copies of an agent can be linked to multiple copies of a carrier, which are in turn linked to each other, multiple copies of an agent can be linked to a single copy of a carrier, or a single copy of an agent can be linked to multiple copies of a carrier, or different carriers. Suitable carriers include serum albumins, keyhole limpet hemocyanin, immunoglobulin molecules, thyroglobulin, ovalbumin, tetanus toxoid, or a toxoid from other pathogenic bacteria, such as diphtheria (e.g., $CRM_{197}$), E. coli, cholera, or H. pylori, or an attenuated toxin derivative.

Immunogens are often administered with pharmaceutically acceptable adjuvants. The adjuvant increases the titer of induced antibodies and/or the binding affinity of induced antibodies relative to the situation if the peptide were used alone. A variety of adjuvants can be used in combination with an immunogenic fragment of MCAM, to elicit an immune response. Preferred adjuvants augment the intrinsic response to an immunogen without causing conformational changes in the immunogen that affect the qualitative form of the response. Preferred adjuvants include aluminum hydroxide and aluminum phosphate, 3 De-O-acylated monophosphoryl lipid A (MPL™) (see GB 2220211 (RIBI Immuno-Chem Research Inc., Hamilton, Mont., now part of Corixa). Stimulon™ QS-21 is a triterpene glycoside or saponin isolated from the bark of the Quillaja Saponaria Molina tree found in South America (see Kensil et al., in *Vaccine Design: The Subunit and Adjuvant Approach* (eds. Powell & Newman, Plenum Press, NY, 1995); U.S. Pat. No. 5,057,540), (Aquila BioPharmaceuticals, Framingham, Mass.; now Antigenics, Inc., New York, N.Y.). Other adjuvants are oil in water emulsions (such as squalene or peanut oil), optionally in combination with immune stimulants, such as monophosphoryl lipid A (see Stoute et al., *N. Engl. J. Med.* 336, 86-91 (1997)), pluronic polymers, and killed mycobacteria. Another adjuvant is CpG (WO 98/40100). Adjuvants can be administered as a component of a therapeutic composition with an active agent or can be administered separately, before, concurrently with, or after administration of the therapeutic agent.

3. Types of Antibodies

Antibodies can be monoclonal or polyclonal. Antibodies can be nonhuman, such as mouse or rat, nonhuman primate or can be human. Antibodies can be chimeric, veneered, humanized, primatized and the like.

Monoclonal antibodies are humanized using the methods described above and the methods described in Queen, U.S. Pat. Nos. 5,530,101 and 5,585,089; Winter, U.S. Pat. No. 5,225,539, Carter, U.S. Pat. No. 6,407,213, Adair, U.S. Pat. Nos. 5,859,205 6,881,557, Foote, U.S. Pat. No. 6,881,557.

The invention further provides chimeric and veneered forms of non-human antibodies that bind specifically to the MCAM epitopes described above.

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues with residues from the corresponding positions of a human antibody sequence (Padlan, Mol. Immunol. 28:489, 1991). The result is an antibody in which the CDRs are entirely or substantially from a non-human antibody and the variable region frameworks of the non-human antibody are made more human-like by the substitutions.

Human antibodies against MCAM are provided by a variety of techniques described below. Some human antibodies are selected by competitive binding experiments, by the phage display method of Winter, above, or otherwise, to have the same epitope specificity as a particular mouse antibody, such as one of the mouse monoclonals described in the examples. Human antibodies can also be screened for a particular epitope specificity by using only a fragment of MCAM as the target antigen, and/or by screening antibodies against a collection of deletion mutants of MCAM.

Methods for producing human antibodies include the trioma method of Oestberg et al., *Hybridoma* 2:361-367 (1983); Oestberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. Nos. 5,877,397, 5,874,299, 5,814,318, 5,789,650, 5,770,429, 5,661,016, 5,633,425, 5,625,126, 5,569,825, 5,545,806, *Nature* 148, 1547-1553 (1994), *Nature Biotechnology* 14, 826 (1996), Kucherlapati, WO 91/10741 (1991) and phage display methods (see, e.g., Dower et al., WO 91/17271 and McCafferty et al., WO 92/01047, U.S. Pat. Nos. 5,877,218, 5,871,907, 5,858,657, 5,837,242, 5,733,743 and 5,565,332.

Chimeric, humanized (including veneered) and human antibodies are typically produced by recombinant expression as described above.

The invention further provides non-antibody binding molecules. Non-antibody binding molecules include, for example, anticalins, which are based upon the lipocalin scaffold, a protein structure characterized by a rigid beta-barrel that supports four hypervariable loops which form the ligand binding site. Novel binding specificities are engineered by targeted random mutagenesis in the loop regions, in combination with functional display and guided selection (Skerra (2008) FEBS J. 275: 2677-2683). Other suitable scaffolds may include, for example, adnectins, or monobodies, based on the tenth extracellular domain of human fibronectin III (Koide and Koide (2007) Methods Mol. Biol. 352: 95-109); affibodies, based on the Z domain of staphylococcal protein A (Nygren et al. (2008) FEBS J. 275: 2668-2676)); DARPins, based on ankyrin repeat proteins (Stumpp et al. (2008) Drug. Discov. Today 13: 695-701); fynomers, based on the SH3 domain of the human Fyn protein kinase (Grabulovski et al. (2007) J. Biol. Chem. 282: 3196-3204); affitins, based on Sac7d from *Sulfolobus acidolarius* (Krehenbrink et al. (2008) J. Mol. Biol. 383: 1058-1068); affilins, based on human y-B-crystallin (Ebersbach et al. (2007) J. Mol. Biol. 372: 172-185); avimers, based on the A domains of membrane receptor proteins (Silverman et al. (2005) Biotechnol. 23: 1556-1561); cysteine-rich knottin peptides (Kolmar (2008) FEBS J. 275: 2684-2690); and engineered Kunitz-type inhibitors (Nixon and Wood (2006) Curr. Opin. Drug. Discov. Dev. 9: 261-268). For review, see Gebauer and Skerra (2009) Curr. Opin. Chem. Biol. 13: 245-255.

In some of these antibodies, the antibody is not any one of the antibodies or antibodies including CDRs (as defined by Kabat, Chothia, or a composite thereof) entirely or substantially from the antibodies described in WO/2012/170071 and PCT/US2013/058773, particularly the antibodies designated clone 15 (defined by SEQ ID NOs:12-21) and clone 17 (defined by SEQ ID NOs:1-10) in WO/2012/170071 and the mouse anti-human MCAM monoclonal clones designated 1174.1.3, 1414.1.2, 1415.1.1, and 1749.1.3, and the rat anti-human MCAM monoclonal antibody clones designated 2120.4.19 and 2107.4.10 described in PCT/US2013/058773.

4. Methods of Screening Antibodies for Activity

The inhibitory activity of the MCAM antibodies described herein can be assayed by any method known in the art, including competitive binding assays with antibodies that bind the same or a substantially similar epitope (e.g., m1749) and blocking of MCAM binding with its ligand, the laminin α4 chain of laminin 411.

For example, the activity of MCAM antibodies to block the interaction between MCAM and the laminin α4 chain of laminin 411 can be screened as follows. MCAM-expressing cells are (a) incubating with a recombinant polypeptide comprising a laminin α4 chain, e.g., an α4 chain of laminin 411, in the presence or absence of a candidate antibody; (b) monitoring the level of binding of the laminin α4 to the cells, e.g. by fluorescence microscopy or flow cytometry; and (c) identifying said candidate antibody as an inhibitor the MCAM/laminin α4 interaction if the level of laminin α4 binding is lower in the presence than in the absence of the candidate antibody. An alternate screening protocol involves the use of a population of cells expressing a laminin α4 chain, which can be incubated with MCAM, in the presence and absence of a candidate antibody, and binding of MCAM to the cell population monitored. If the binding of MCAM to the cell population in the presence of the candidate antibody is lower than in its absence, the candidate antibody is an MCAM antagonist.

Other methods of monitoring include fluorescence-activated cell sorting (FACS) and enzyme-linked immunosorbent assay (ELISA).

The MCAM antagonists identified based on their ability to inhibit the binding of MCAM to its ligand, e.g., a laminin α4 chain, are candidates for the treatment of inflammatory conditions characterized by infiltration of MCAM-expressing cells.

The inhibitory activity of an MCAM antibody can also be assessed in vivo. An example of a methodology for assessing the inhibitory activity of an MCAM antibody is with an experimental autoimmune encephalomyelitis (EAE) model. EAE is a disease that is generated in laboratory animals to produce symptoms similar to those of multiple sclerosis (MS) in humans See, e.g., Bauer et al., *Proc. Nat'l Acad. Sci. USA* 106: 1920-1925 (2009). EAE is generally produced by injecting animals with different proteins from the central nervous system of other animals, for example, extracts of myelin basic protein and whole spinal cord or brain tissue, or with T cells that specifically react to myelin. EAE is commonly used to follow the course of relapsing or progressive forms of MS. EAE has been served as a suitable animal model to both develop therapeutic agents for MS and study the specific disease processes of MS. See, e.g., Gold et al., *Brain* 129: 1953-1971 (2006); see also Steinman et al., *Ann. Neurol.* 60: 12-21 (2006).

The effects of MCAM blockade on disease progression can be examined in a therapeutic model of EAE in which TH17 polarization occurs in vivo. Mice are immunized with PLP 139-151 peptide to induce EAE. After disease onset, mice are treated intraperitoneally with either a candidate anti-MCAM antibody or isotype control, and every day thereafter. Mice are monitored daily and scored for in a blinded manner, and body weights were obtained every 2-3 days. A delay in relapse and significant reduction in symptom severity in mice treated with a candidate MCAM antibody is indicative of a successful candidate antibody.

F. Conjugated Antibodies

Conjugated antibodies that specifically bind to MCAM can be useful in targeting cancer or tumor cells for destruction or in targeting cells involved in autoimmune diseases or neuroinflammatory diseases. Such antibodies can also be useful in targeting any disease mediated at least in part by expression of MCAM. For example, such antibodies can be conjugated with other therapeutic agents, other proteins, other antibodies, and/or detectable labels. See WO 03/057838; U.S. Pat. No. 8,455,622. Such therapeutic agents can be any agent that can be used to treat, combat, ameliorate, prevent, or improve an unwanted condition or disease in a patient, such as an autoimmune disease, a neuroinflammatory disease, or a cancer. Therapeutic agents can include cytotoxic agents, cytostatic agents, radiotherapeutic agents, immunomodulators, or any biologically active agents that facilitate or enhance the activity of the antibody. A cytotoxic agent can be any agent that is toxic to a cell. A cytostatic agent can be any agent that inhibits cell proliferation. An immunomodulator can be any agent that stimulates or inhibits the development or maintenance of an immunologic response. A radiotherapeutic agent can be any molecule or compound that emits radiation. If such therapeutic agents are coupled to an MCAM-specific antibody, such as the antibodies described herein, the coupled therapeutic agents will have a specific affinity for MCAM-expressing cells (e.g., immune cells, such as TH17-expressing cells, or cancer cells, such as malignant melanocytes) over other cells. Consequently, administration of the conjugated antibodies directly targets MCAM-expressing cells with minimal effects on other surrounding cells and tissue. This can be particularly useful for therapeutic agents that are too toxic to be administered on their own. In addition, smaller quantities of the therapeutic agents can be used.

Antibodies can be modified to act as immunotoxins. See, e.g., U.S. Pat. No. 5,194,594. For example, ricin, a cellular toxin derived from plants, can be coupled to antibodies by using the bifunctional reagents S-acetylmercaptosuccinic anhydride for the antibody and succinimidyl 3-(2-pyridyldithio)propionate for ricin. See Pietersz et al., *Cancer Res.* 48(16):4469-4476 (1998). The coupling results in loss of B-chain binding activity of ricin, while impairing neither the toxic potential of the A-chain of ricin nor the activity of the antibody. Similarly, saporin, an inhibitor of ribosomal assembly, can be coupled to antibodies via a disulfide bond between chemically inserted sulfhydryl groups. See Polito et al., *Leukemia* 18:1215-1222 (2004).

Radioisotopes can also be linked to antibodies. Preferred radioisotopes include yttrium$^{90}$ (90Y), indium$^{111}$ (111In), $^{131}$I, $^{99}$mTc, radiosilver-111, radiosilver-199, and Bismuth$^{213}$. Linkage of radioisotopes to antibodies may be performed with conventional bifunction chelates. For radiosilver-11 and radiosilver-199 linkage, sulfur-based linkers may be used. See Hazra et al., *Cell Biophys.* 24-25:1-7 (1994). Linkage of silver radioisotopes may involve reducing the immunoglobulin with ascorbic acid. For radioisotopes such as 111In and 90Y, ibritumomab tiuxetan can be used and will react with such isotopes to form 111In-ibritumomab tiuxetan and 90Y-ibritumomab tiuxetan, respectively. See Witzig, *Cancer Chemother. Pharmacol.*, 48 Suppl 1:S91-S95 (2001).

Other therapeutic agents may also be linked to antibodies. Therapeutic agents are usually cytotoxic or cytostatic. For example, antibodies can be conjugated with toxic chemotherapeutic drugs such as maytansine, geldanamycin, tubulin inhibitors, such as auristatins, or minor groove binding agents, such as calicheamicin. Other representative therapeutic agents include agents known to be useful for treatment, management, or amelioration of an autoimmune disease, a neuroinflammatory disease, or a cancer, or symptoms of an autoimmune disease, a neuroinflammatory disease, or a cancer. Examples of such therapeutic agents are disclosed elsewhere herein.

Antibodies can also be coupled with other proteins. For example, antibodies can be coupled with Fynomers. Fynomers are small binding proteins (e.g., 7 kDa) derived from the human Fyn SH3 domain. They can be stable and soluble, and they can lack cysteine residues and disulfide bonds. Fynomers can be engineered to bind to target molecules with the same affinity and specificity as antibodies. They are suitable for creating multi-specific fusion proteins based on antibodies. For example, Fynomers can be fused to N-terminal and/or C-terminal ends of antibodies to create bi- and tri-specific FynomAbs with different architectures. Fynomers can be selected using Fynomer libraries through screening technologies using FACS, Biacore, and cell-based assays that allow efficient selection of Fynomers with optimal properties. Examples of Fynomers are disclosed in Grabulovski et al., *J. Biol. Chem.* 282:3196-3204 (2007); Bertschinger et al., *Protein Eng. Des. Sel.* 20:57-68 (2007); Schlatter et al., *MAbs.* 4:497-508 (2011); Banner et al., *Acta. Crystallogr. D. Biol. Crystallogr.* 69(Pt6):1124-1137 (2013); and Brack et al., *Mol. Cancer Ther.* 13:2030-2039 (2014).

The antibodies disclosed herein can also be coupled or conjugated to one or more other antibodies (e.g., to form antibody heteroconjugates). Such other antibodies can bind to different epitopes within MCAM or can bind to a different target antigen.

Antibodies can also be coupled with a detectable label. Such antibodies can be used, for example, for diagnosing of an autoimmune disease, a neuroinflammatory disease, or a cancer, for monitoring progression of an autoimmune disease, a neuroinflammatory disease, or a cancer, and/or for assessing efficacy of treatment. Such antibodies can be useful for performing such determinations in subjects having or being susceptible to an autoimmune disease, a neuroinflammatory disease, or a cancer, or in appropriate biological samples obtained from such subjects. Representative detectable labels that may be coupled or linked to an antibody include various enzymes, such as horseradish peroxidase, alkaline phosphatase, beta-galactosidase, or acetylcholinesterase; prosthetic groups, such streptavidin/biotin and avidin/biotin; fluorescent materials, such as umbelliferone, fluorescein, fluorescein isothiocyanate, rhodamine, dichlorotriazinylamine fluorescein, dansyl chloride or phycoerythrin; luminescent materials, such as luminol; bioluminescent materials, such as luciferase, luciferin, and aequorin; radioactive materials, such as radiosilver-111, radiosilver-199, Bismuth$^{213}$, iodine ($^{131}$I, $^{125}$I, $^{123}$I, $^{121}$I,), carbon ($^{14}$C), sulfur ($^{5}$S), tritium ($^{3}$H), indium ($^{115}$In, $^{113}$In, $^{112}$In, $^{111}$In,), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies; nonradioactive paramagnetic metal ions; and molecules that are radiolabelled or conjugated to specific radioisotopes.

Therapeutic agents, other proteins, other antibodies, and/or detectable labels may be coupled or conjugated, directly or indirectly through an intermediate (e.g., a linker), to a murine, chimeric, veneered, or humanized antibody using techniques known in the art. See e.g., Arnon et al., "Monoclonal Antibodies For Immunotargeting Of Drugs In Cancer Therapy," in Monoclonal Antibodies And Cancer Therapy, Reisfeld et al. (eds.), pp. 243-56 (Alan R. Liss, Inc. 1985); Hellstrom et al., "Antibodies For Drug Delivery," in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review," in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy," in Monoclonal Antibodies For Cancer Detection And Therapy, Baldwin et al. (eds.), pp. 303-16 (Academic Press 1985); and Thorpe et al., *Immunol. Rev.*, 62:119-58 (1982). Suitable linkers include, for example, cleavable and non-cleavable linkers. Different linkers that release the drugs under acidic or reducing conditions or on exposure to specific proteases can be employed. Likewise, different linkers that release the coupled therapeutic agents, proteins, antibodies, and/or detectable labels under acidic or reducing conditions, on exposure to specific proteases, or under other defined conditions can be employed.

IV. Methods of Treatment and Pharmaceutical Compositions

The antibodies or other antagonists of the invention can be used for treating or effecting prophylaxis of subjects having (e.g., meeting art-recognized criteria, such as those of the DSM-IV-TR or DSM-V) or at elevated risk relative to the general population of an autoimmune disease, neuroinflammatory disease and cancer among others. Elevated risk can be assessed from presence of one or more genetic or biochemical markers associated with the disease, or one or more symptoms consistent with the disease but insufficient to allow a definite diagnosis. The above mentioned categories or disease are not necessarily mutually exclusive of one another; for example, multiple sclerosis can be classified as neuroinflammatory or autoimmune. Some specific exemplary diseases treatable by the present methods include multiple sclerosis, Parkinson's disease, allergic contact dermatitis, psoriasis, psoriatic arthritis, rheumatoid arthritis, sarcoidosis, inflammatory bowel disease, Crohn's disease, and cancer, particularly, solid tumors, such as melanoma. Although practice of the methods is not dependent on understanding of mechanism, it is believed that in some methods antibodies or other antagonists function at least in part by inhibiting the interaction of MCAM expressed on T cells (e.g., TH17 cells) and laminin α4 chain, e.g., an α4 chain of laminin 411 expressed on the surface of an endothelial cell. Antibody-drug conjugates can have additional mechanisms of action including the cytotoxic or cytostatic effect of the linked agent, typically after uptake within the targeted cell. Antibody-drug conjugates may also induce tumor-associated macrophage toxicity.

Neuroinflammatory conditions are characterized by CNS inflammation and/or cell/tissue damage. The indicia can include increased glial activation, increased pro-inflammatory cytokine/chemokine levels (e.g., TNFα, INFγ, IL-1β), increased blood-brain-barrier permeability, and/or increased immune cell (e.g., leukocyte) recruitment/invasion to the CNS. The neuroinflammation is often chronic associated with chronic activation of cells of the immune system (i.e., autoimmune-associated neuroinflammation) but can alternatively or additional have acute episodes.

Multiple sclerosis is a preferred disease for treatment in any of its at least four subtypes. Relapsing-remitting MS (RR-MS) is the most common form of MS and is characterized by clearly defined exacerbations/relapses (acute attacks) followed by partial or complete recovery. There is no disease progression between the relapse periods. Initially (at the time of diagnosis) RR-MS represents about 85% of all newly diagnosed subjects. The definition of relapse requires the new symptom or sign to be present for at least 24 hours, to not be associated with a fever or intercurrent illness (such as the "flu" or a urinary tract infection), because an elevated body temperature can unmask silent or old lesions.

Primary progressive (PP-MS) is continuous from the beginning without clear relapses. There can be plateaus (periods of stabilization). 10-15% of all MS subjects are in this group and it tends to occur in older aged individuals. The female to male ratio is equal in this group, unlike other forms where females predominant by about 2:1. Also PP-MS tends to present with fewer cerebral MRI changes and more myelopathy/spinal cord related changes.

A secondary progressive form (SP-MS) starts as a RR-MS and later steady progression occurs with or without relapses. Approximately 50% of relapsing-remitting subjects progress to the secondary progressive form.

A progressive relapsing form (PR-MS), occurring in about 5% of individuals, is progressive from the onset with superimposed relapses (with or without recovery).

Diagnosis of MS is usually based on a medical history, a neurologic exam and various tests, including magnetic resonance imaging (MRI), evoked potentials (EP) and spinal fluid analysis. A definitive diagnosis of MS requires evidence of damage in at least two separate areas of the central nervous system (CNS), which includes the brain, spinal cord and optic nerves and evidence that the damage occurred at least one month apart and exclusion of all other possible diagnoses. As well as therapeutically treating subjects having a diagnosis of MS by art-recognized criteria, the present methods can also be used prophylactically to treat individually having at least one sign or symptom of MS placing them at increased risk of progression to MS compared with the general population of healthy individuals. For example, the methods can be used to treat individuals who have had one attack (also called a relapse or an exacerbation) of MS-like symptoms—referred to as a clinically-isolated syndrome (CIS), who may or may not go on to develop MS. Individuals at risk of developing MS can also be identified by presence of an antibody to the protein KIR4.1 in their serum, among other methods.

Neuroinflammatory disease also includes Parkinson's disease. Symptoms of Parkinson's disease include tremor (e.g., trembling in hands, arms, legs, jaw, and face); rigidity or stiffness of the limbs and trunk; bradykinesia or slowness of movement; postural instability or impaired balance and coordination; depression and other emotional changes; difficulty in swallowing, chewing, and speaking; urinary problems or constipation; skin problems; sleep disruptions. Parkinson's disease can be diagnosed from such symptoms, and/or brain scans and/or other tests to rule out other diseases.

The present methods can be used to inhibit growth or metastasis of cancer. Cancers can be hematopoietic malignancies or solid tumors, i.e., masses of cells that result from excessive cell growth or proliferation, either benign or malignant, including pre-cancerous legions. Cancers can be benign, malignant, or metastatic. Metastatic cancer refers to a cancer that has spread from the place where it first started to another place in the body. Tumors formed by metastatic cancer cells are called a metastatic tumor or a metastasis, which is a term also used to refer to the process by which cancer cells spread to other parts of the body. In general, metastatic cancer has the same name and same type of cancer cells as the original, or primary, cancer. Examples of cancer include solid tumors, such as melanoma, carcinoma, blastoma, and sarcoma. Cancers also include hematologic malignancies, such as leukemia or lymphoid malignancies, such as lymphoma. More particular examples of such cancers include squamous cell cancer, lung cancer, cancer of the peritoneum, hepatocellular cancer, gastric or stomach cancer including gastrointestinal cancer, pancreatic cancer, glioma, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Autoimmune diseases include systemic autoimmune diseases, organ- or tissue-specific autoimmune diseases, and diseases that exhibit autoimmune-type expressions. In these diseases, the body develops a cellular and/or humoral immune response against one of its own antigens, leading to destruction of that antigen and potentially crippling and/or fatal consequences. The cellular response if present can be B-cell or T-cell or both. TH17 cells, a lineage T helper cells characterized by production of interleukin (IL)-17 and IL-22, have been reported to enter tissues to facilitate pathogenic autoimmune responses, including multiple sclerosis in humans and experimental autoimmune encephalomyelitis (EAE) in mice. See, e.g., Cua et al., Nature 421: 744-748 (2003); Ivonov et al., Cell 126: 1121-1133 (2006). TH17 cells may initiate or propagate an inflammatory response by their specific recruitment to and infiltration of tissue.

Examples of autoimmune diseases include Graves' disease, Hashimoto's thyroiditis, autoimmune polyglandular syndrome, insulin-dependent diabetes mellitus (type 1 diabetes), insulin-resistant diabetes mellitus (type 2 diabetes), immune-mediated infertility, autoimmune Addison's disease, pemphigus vulgaris, pemphigus foliaceus, dermatitis herpetiformis, autoimmune alopecia, vitiligo, autoimmune hemolytic anemia, idiopathic thrombocytopenic purpura, autoimmune thrombocytopenic purpura, pernicious anemia, myasthenia gravis, Guillain-Barre syndrome, stiff man syndrome, acute rheumatic fever, sympathetic ophthalmia, Goodpasture's syndrome, autoimmune uveitis, temporal arteritis, Bechet's disease, inflammatory bowel diseases, Crohn's disease, ulcerative colitis, primary biliary cirrhosis, autoimmune hepatitis, autoimmune oophoritis, fibromyalgia, polymyositis, dermatomyositis, ankylosing spondylitis, Takayashu arteritis, panniculitis, pemphigoid, vasculitis of unknown origin, anca negative vasculitis, anca positive vasculitis, systemic lupus erythematosus, psoriatic arthritis, rheumatoid arthritis, scleroderma, systemic necrotizing vasculitis, Wegener's granulomatosis, CREST syndrome, antiphospholipid syndrome, Sjogren's syndrome, eosinophilic gastroenteritis, atypical topical dermatitis, cardiomyopathy, post-infectious syndromes, postinfectious endomyocarditis, celiac disease, multiple sclerosis, sarcoidosis, and psoriasis.

Antibodies or other antagonists are administered in an effective regime meaning a dosage, route of administration and frequency of administration that delays the onset, reduces the severity, inhibits further deterioration, and/or ameliorates at least one sign or symptom of a disease being treated (e.g., cancer). If a patient is already suffering from a disorder, the regime can be referred to as a therapeutically effective regime. If the patient is at elevated risk of the disorder relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

Exemplary dosages for an antibody are 0.1-20, or 0.5-5 mg/kg body weight (e.g., 0.5, 1, 2, 3, 4 or 5 mg/kg) or 10-1500 mg as a fixed dosage. The dosage depends on the condition of the patient and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, topical, intranasal or intramuscular. Administration into the systemic circulation by intravenous or subcutaneous administration is preferred. Intravenous administration can be, for example, by infusion over a period such as 30-90 min.

The frequency of administration depends on the half-life of the antibody in the circulation, the condition of the patient and the route of administration among other factors. The frequency can be daily, weekly, monthly, quarterly, or at irregular intervals in response to changes in the patient's condition or progression of the disorder being treated. An exemplary frequency for intravenous administration is between weekly and quarterly over a continuous cause of treatment, although more or less frequent dosing is also possible. For subcutaneous administration, an exemplary dosing frequency is daily to monthly, although more or less frequent dosing is also possible.

The number of dosages administered depends on whether the disorder is acute or chronic and the response of the disorder to the treatment. For acute disorders or acute exacerbations of a chronic disorder, between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use.

Treatment with antibodies of the invention can be combined with other treatments effective against the disorder being treated. Combination treatments can be formulated for administered separately. Additional therapeutic agents for treatment of multiple sclerosis include one or more of the following: teriflunomide, interferon beta-1a, interferon beta-1b, glatiramer acetate, fingolimod, and mitoxantrone, or a corticosteroid, such as prednisone, methylprednisolone, or dexamethasone.

Additional therapeutic agents for cancer include alkylating agents such as carmustine, chlorambucil, cisplatin, carboplatin, oxaliplatin, procarbazine, and cyclophosphamide; antimetabolites such as fluorouracil, floxuridine, fludarabine, gemcitabine, methotrexate and hydroxyurea; natural products including plant alkaloids and antibiotics such as bleomycin, doxorubicin, daunorubicin, idarubicin, etoposide, mitomycin, mitoxantrone, vinblastine, vincristine, and Taxol (paclitaxel) or related compounds such as Taxotere®; the topoisomerase 1 inhibitor irinotecan; temozolomide and Gliadel®, carmustine; and inhibitors of tyrosine kinases such as Gleevec®, Sutent® (sunitinib malate), Nexavar® (sorafenib) and Tarceva® (erlotinib) or Iressa® (gefitinib); inhibitors of angiogenesis; and monoclonal antibodies, including Herceptin™ against the HER2 antigen; Avastin® against VEGF; or antibodies to the Epidermal Growth Factor (EGF) receptor such as Erbitux® (cetuximab) and Vectibix® (panitumumab).

Additional agents for treating Parkinson's disease include including levodopa, benzaseride, carbidopa, dopamine agonists, non-ergot dopamine agonists, catechol-O-methyl ("COMT") inhibitors such as, for example, entacopone or tolcopone, monoamine oxidase ("MAO") inhibitors, such as, for example, rasagaline, amantadine, or anticholinergic agents V. Kits The invention further provides kits (e.g., containers) comprising the MCAM antibodies or other antagonists of the invention and related materials, such as instructions for use (e.g., package insert). The instructions for use may contain, for example, instructions for administration of the MCAM antagonists and optionally one or more additional agents. The containers of MCAM antagonist(s) may be unit doses, bulk packages (e.g., multi-dose packages), or sub-unit doses.

Package insert refers to instructions customarily included in commercial packages of therapeutic products that contain information about the indications, usage, dosage, administration, contraindications and/or warnings concerning the use of such therapeutic products Kits can also include a second container comprising a pharmaceutically-acceptable buffer, such as bacteriostatic water for injection (BWFI), phosphate-buffered saline, Ringer's solution and dextrose solution. It can also include other materials desirable from a commercial and user standpoint, including other buffers, diluents, filters, needles, and syringes.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Materials and Methods
Antibody Generation/Characterization

For the generation of antibodies capable of binding to murine MCAM, MCAM-Fc was generated by fusing the extracellular domain of murine MCAM to human IgG and produced in CHO cells using standard techniques. Lou/M rats were immunized with 100 µg of MCAM-Fc protein in CFA (1:1 volume). Rats were boosted two times at two week intervals with MCAM-Fc protein in incomplete Freund's adjuvant (IFA) (1:1 volume). Hybridomas were generated from immunized rats using standard protocols and clones were selected by Clonepix. CHO cells were transfected with the full length murine MCAM gene and selected for stable expression using neomycin and standard techniques. Parental CHO cells (MCAM negative) were fluorescently labeled with carboxyfluorescein succinimidyl ester (CFSE) using standard techniques and mixed at a 1:1 ratio with unlabeled MCAM transfected CHO cells. Hybridoma supernatants were incubated with this mixture of cells for 30 minutes and binding of potential MCAM specific antibodies was detected with a fluorescently labeled anti-rat secondary antibody (Jackson Immuno) by flow cytometry.

Supernatants from hybridomas that screened positive for MCAM specific antibodies were pre-incubated with fluorescently labeled mouse MCAM-Fc protein (5 µg/mL) for 30 minutes before addition to the laminin α4 expressing cell line WM2664 and neutralization of binding of the MCAM-Fc protein to the cell line was determined by flow cytometry.

For the generation of rat antibodies capable of binding to human MCAM, hMCAM-Fc was generated by fusing the extracellular domain of human MCAM to human IgG and produced in CHO cells using standard techniques. Lou/M rats were immunized with 250 µg of hMCAM-Fc protein in CFA (1:1 volume). Rats were boosted two times at two week intervals with hMCAM-Fc protein in incomplete Freund's adjuvant (IFA) (1:1 volume). Hybridomas were generated from immunized rats using standard protocols and clones were selected by Clonepix. CHO cells were transfected with the full length human MCAM gene and selected for stable expression using neomycin and standard techniques. Parental CHO cells (MCAM negative) were fluorescently labeled with carboxyfluorescein succinimidyl ester (CFSE) using standard techniques and mixed at a 1:1 ratio with unlabeled human MCAM transfected CHO cells. Hybridoma supernatants were incubated with this mixture of cells for 30 minutes and binding of potential human MCAM specific antibodies was detected with a fluorescently labeled anti-rat secondary antibody (Jackson Immuno) by flow cytometry.

For the generation of mouse antibodies capable of binding to human MCAM, hMCAM-Fc was generated by fusing the extracellular domain of human MCAM to human IgG and produced in CHO cells using standard techniques. Balb/c mice were immunized with 50 µg of hMCAM-Fc protein in CFA (1:1 volume). Mice were boosted two times at two week intervals with hMCAM-Fc protein in incomplete Freund's adjuvant (IFA) (1:1 volume). Hybridomas were generated from immunized mice using standard protocols and clones were selected by Clonepix. CHO cells were transfected with the full length human MCAM gene and selected for stable expression using neomycin and standard techniques. Parental CHO cells (MCAM negative) were fluorescently labeled with carboxyfluorescein succinimidyl ester (CFSE) using standard techniques and mixed at a 1:1 ratio with unlabeled human MCAM transfected CHO cells. Hybridoma supernatants were incubated with this mixture of cells for 30 minutes and binding of potential human MCAM specific antibodies was detected with a fluorescently labeled anti-mouse secondary antibody (Jackson Immuno) by flow cytometry.

Supernatants from hybridomas that screened positive for human MCAM specific antibodies were pre-incubated with fluorescently labeled hMCAM-Fc protein (5 µg/mL) for 30 minutes before addition to the laminin α4 expressing cell line WM2664 and neutralization of binding of the hMCAM-Fc protein to the cell line was determined by flow cytometry.

Nucleic Acid and Protein Manipulation

For determination of CDRs, total RNA was isolated from hybridoma cells using RNAquous-4PCR kit (Ambion), and was used for cDNA synthesis. First and second strand cDNA was synthesized using methods modified from Marathon cDNA amplification (Clontech) with the cDNA adaptor ligated to the 5'-end of the obtained dscDNA. The reverse specific primer was designed based on the specific antibody isotype constant region sequence for both heavy and light chains, and was used along with the adaptor primer in the PCR amplification of both VL and VH fragments using Pfu Ultra DNA polymerase (Stratagene). The amplified PCR product was cloned into pCR-Blunt-TOPO (Invitrogen), and the nucleotide sequence was determined. The sequences of the identified clones were compared for percent identity within the VL and VH sequences.

For determination of IL-17 concentrations in the supernatant, ELISA was performed using a commercial kit (R&D Systems).

Example 1

Generation of Anti-MCAM Monoclonal Antibodies

Mouse and rat monoclonal antibodies directed against human MCAM protein were generated as described in Materials and Methods above. The specific binding between the monoclonal antibody and human MCAM was confirmed by assessing the monoclonal antibody's ability to bind to cells transfected with human MCAM. For this, untransfected cells were labeled with carboxyfluorescein succinimidyl ester (CFSE) and mixed with unlabeled human MCAM transfected cells. Untransfected cells could, therefore, be differentiated.

Using these techniques, 823 independent mouse fusions clones were isolated and shown to express an antibody capable of binding to human MCAM. Additionally, 152 independent rat fusions clones were isolated and shown to express an antibody capable of binding to human MCAM.

Next, the anti-human MCAM monoclonal antibodies were used to test their ability to block the binding of human MCAM to its ligand. Human MCAM-Fc protein (5 µg/mL) was pre-incubated with isotype control antibody, or 10 µg/mL of the test monoclonal antibody for 30 minutes in PBS. The mixture was added to healthy spinal cord tissue sections and subsequently characterized by fluorescence microscopy as described in Materials and Methods above. Furthermore, parental CHO cells (CHOK1) or CHO cells transfected with a human MCAM gene were preincubated with CHO culture media (DMEM), recombinant laminin 411 (10 µg/ml), or recombinant laminin 511 (i.e., laminin 10 (α5β1γ1)) (10 µg/ml) at 37° C. for 45 minutes. Cells were washed, and specific binding of laminin 411, but not laminin 511, to MCAM was detected with a pan-laminin antibody by flow cytometry. Pre-incubation of human MCAM transfected CHO cells with the anti-MCAM antibody (at 20 µg/ml), prior to laminin incubation, abolished the binding of human MCAM to laminin 411.

Using this technique, it was shown that 87 of the 823 independent mouse fusion clones and 26 of the 152 independent rat fusion clones described above expressed an antibody that was capable of blocking the interaction between human MCAM protein and its ligand, α-4 chain of laminin.

Example 2

Further Characterization of Anti-MCAM Monoclonal Antibodies

The 87 independent mouse fusion clones and 26 independent rat fusion clones described in Example 1 above as being capable of (i) binding to human MCAM, and (ii) blocking the interaction between human MCAM and the α-4 chain of laminin were further characterized as follows. First, IC50 quantitation for the ability of the monoclonal antibody to block the binding of human MCAM to the α-4 chain of laminin was determined as follows. CHO cells expressing human MCAM were incubated with an anti-human MCAM antibody (at various concentrations) for 30 minutes at 4 degrees Celsius. Unbound antibody was then washed away, and the cells were incubated with recombinant human laminin 411 at 20 ug/ml for 45 minutes at 37 degrees Celsius. Unbound laminin was then washed away, and the laminin bound to the surface of the cells was detected with fluorescently labeled anti-laminin antibodies. After washing, the amount of laminin bound to the surface was detected by flow cytometry, and IC50s were calculated based on the mean fluorescent intensity.

Using the above described assay, six independent anti-human MCAM monoclonal antibody clones were identified as binding to human MCAM and having the greatest ability to block the interaction between human MCAM expressed on the surface of cells and its binding ligand, human laminin 411. These six anti-MCAM monoclonal antibody clones are herein referred to as (i) the mouse anti-human MCAM monoclonal clones 1174.1.3, 1414.1.2, 1415.1.1, and 1749.1.3, and (ii) the rat anti-human MCAM monoclonal antibody clones 2120.4.19 and 2107.4.10. Amino acid and nucleic acid sequences of the heavy and light chains of these antibodies, and their hypervariable regions, are provided in SEQ ID NOs:29-92. More specifically, in the above assay, IC50s for the monoclonal antibody clones 1174.1.3, 1414.1.2, 1415.1.1, 1749.1.3, 2120.4.19, and 2107.4.10 were determined to be 0.469 ug/ml, 0.431 ug/ml, 0.307 ug/ml, 0.545 ug/ml, 0.888 ug/ml, and 0.290 ug/ml, respectively. Moreover, experiments performed to determine the specific binding affinity of each monoclonal antibody demonstrated that each was capable of binding to human MCAM protein with high affinity (data not shown). As such, each of these specific monoclonal antibodies was very capable of binding to human MCAM and inhibiting the interaction of cell-expressed human MCAM with its α-4 laminin binding ligand. In contrast, two control antibodies, a non-specific human IgG1 antibody and a previously described, fully human anti-MCAM antibody referred to as ABX-MA1 (e.g., see Mills et al., Cancer Res. 62:5106 (2002), and U.S. Pat. Nos. 6,924,360, 7,067,131, and 7,090,844) were both incapable of blocking the binding interaction between human MCAM and its laminin 411 counterpart. As such, the six specific monoclonal antibodies identified above possess the novel ability to both (i) bind with high affinity to human MCAM on the surface of living cells, and (ii) block the interaction of cell expressed human MCAM with a laminin protein comprising an α-4 laminin polypeptide chain.

Example 3

Domain Binding Analysis for Anti-MCAM Monoclonal Antibodies

ForteBio analysis was employed to determine the location of the antigen epitope on the human MCAM protein that is recognized and bound by monoclonal antibody clones 1174.1.3, 1414.1.2, 1415.1.1, 1749.1.3, 2120.4.19, and 2107.4.10. The following protocol was used: ForteBio anti-human IgG Fc biosensors were used to immobilize various MCAMhFc domains including full length MCAMhFc protein on to biosensor surface. These sensors were dipped into the MCAM specific 1174.1.3, 1414.1.2, 1415.1.1, 1749.1.3, 2120.4.19, or 2107.4.10 antibody for detection of binding to these domains or full length protein. After loading these samples into a black 96 well plate, the Octet Red was programmed as follows: 60 seconds for baseline #1; 180 seconds for loading various domains; 60 seconds for baseline #2; 180 seconds for association of antibody to domain; and 240 seconds for dissociation of antibody from domain.

Reagents and Supplies Used:
1. MCAMhFc final concentration @ 5 ug/ml
2. antibody clones 1174.1.3, 1414.1.2, 1415.1.1, 1749.1.3, 2120.4.19, and 2107.4.10 clones @ 5 ug/ml
3. ForteBio anti-human IgG Fc Capture (AHC) biosensors for kinetics experiments, cat#18-5060
4. Block 96 well plate from Greiner Bio-one, cat#655209
5. ForteBio Octet Red machine
6. Fresh tissue culture medium, DMEM with 20% FCS, was used as buffer for dilution The results from these analyses are as follows.

Monoclonal antibody clones 1174.1.3, 1414.1.2, 1415.1.1, and 1749.1.3 were all shown to bind to an antigenic epitope found on domain 3 of the human MCAM protein, defined specifically by amino acids 244-321 (SEQ ID NO:24) of the human MCAM protein. These monoclonal antibodies were not capable of binding to human MCAM domain 1 (namely amino acids 19-129, SEQ ID NO:22), domain 2 (namely amino acids 139-242, SEQ ID NO:23), or the combination of domains 1 and 2 (namely, amino acids 19-242). Hence, monoclonal antibody clones 1174.1.3, 1414.1.2, 1415.1.1, and 1749.1.3 define a novel antigenic epitope located within domain 3 of the human MCAM protein.

Monoclonal antibody clones 2120.4.19, and 2107.4.10 were each shown to bind to an antigenic epitope defined by the combination of human MCAM domains 1 (namely amino acids 19-129, SEQ ID NO:22), and domain 2 (namely amino acids 139-242, SEQ ID NO:23). Neither of these two monoclonal antibodies bound to human MCAM domain 1 by itself. Hence, monoclonal antibody clones 2120.4.19 and 2107.4.10 define a novel antigenic epitope determined by the presence of both human MCAM protein domains 1 and 2.

In contrast to the above, the previously described fully human anti-MCAM antibody ABX-MA1 binds to a different antigenic epitope than those described above, namely an antigenic epitope that is fully defined and encompassed within human MCAM domain 1 only.

Given these results, since each of monoclonal antibody clones 1174.1.3, 1414.1.2, 1415.1.1, 1749.1.3, 2120.4.19, and 2107.4.10 are capable of both (i) binding to human MCAM, and (ii) blocking the interaction between human MCAM and an α-4 laminin containing protein, whereas the ABX-MA1 antibody is capable of only binding to human MCAM, but not blocking the interaction between human MCAM and an α-4 laminin containing protein, these results demonstrate that human MCAM domain 2, human MCAM domain 3, and the combination thereof play a role in the binding interaction with α-4 laminin chain. Given this, it is clear that antibodies which bind to human MCAM domain 2, human MCAM domain 3, and/or the combination thereof would find use as agents capable of blocking the interaction between human MCAM and α-4 laminin and, thereby, find use for inhibiting the various consequences described herein resulting from that interaction. In contrast, antibodies that bind to an antigenic epitope defined solely by human MCAM domain 1 (such as the ABX-MA1 antibody described herein) are not useful for blocking the MCAM/α-4 laminin interaction and its various downstream biological consequences.

Example 4

Shotgun Mutagenesis Epitope Mapping

Various amino acid residue of interest for anti-MCAM antibody binding were identified using shotgun mutagenesis and high-throughput cellular expression technology that enables the expression and analysis of large libraries of mutated target proteins within eukaryotic cells. Every residue in the human MCAM protein was individually mutated to an alanine, or other specified residue, to assay changes in function. Proteins were expressed within standard mammalian cell lines.

Table 1 shows a summary of the reagents and methods used to generate the shotgun mutagenesis library.

TABLE 1

| | |
|---|---|
| Parental plasmid | hsMCAM-V5/HIS6 (Accession # NP 006491) |
| Final library size | 528 mutant clones plus 17 additional site-directed mutants |
| Mutation Strategy | Alanine Scanning Mutagenesis |
| Cell type | BHK-S |
| Epitope Tag | C-terminal V5/HIS6 |

Full-length human MCAM was successfully codon-optimized, synthesized, and subcloned into a mammalian high-expression vector. This parental construct was then sequence-verified and validated for mammalian cell expression by immunodetection methods.

Detection of 1749.1.3 antibody and mouse sera binding to MCAM by immunofluorescence was successfully optimized for the high-throughput shotgun mutagenesis format. Serial dilutions of each primary antibody were tested with a single dilution of secondary antibody in a 384-well format. Antibodies were tested for detection of 293T and BHK cells expressing human MCAM. Optimal assay conditions were selected for screening the complete mutation library.

The MCAM mutation library was created and sequence verified, consisting of 545 clones (528/536 alanine mutants and 17/17 site-directed mutants), each bearing either a single residue substitution to alanine (alanine residues are substituted to serine) or a specified residue. Residues 35, 66, 161, 261, 342, 380, 414, and 435 are not represented in the library. The mutation library was screened in triplicate by immunodetection for binding to mouse sera. This validates cell surface expression for each mutant clone.

Multiple rounds of optimization were performed to determine conditions that are suitable for mapping. The following variables were evaluated: multiple laminin concentrations and anti-laminin secondary antibody concentrations, various blocking buffers to reduce nonspecific binding, multiple cell types, and multiple washing steps.

The mutation library was screened in triplicate by immunodetection for binding to the 1749.1.3 antibody. Reactivity was quantified for each mutant to identify point mutants that exhibit loss of binding.

Monoclonal antibody and sera reactivity were quantified for each mutant clone to identify point mutants that exhibit loss of binding without impacting surface expression. The critical residues for each antibody were identified by comparison of the monoclonal antibody binding profile to the sera binding profile of each mutant clone.

BHK cells were transfected with either wild-type (WT) MCAM or vector alone in a 384-well format, followed by immunodetection. Serial dilutions of each antibody (beginning with 4 µg/ml) were tested for immunoreactivity against WT or vector alone (Table 2). Each point represents the average of four replicates.

TABLE 2

| Primary Ab conc | MAb 1749.1.3 | | Ms Sera | | Ms Sera Conc |
|---|---|---|---|---|---|
| (ug/mL) | S/B | Z' | S/B | Z' | (ug/mL) |
| 4.00 | 13.11 | 0.69 | 6.49 | 0.19 | 1:100 |
| 2.00 | 27.98 | 0.58 | 7.69 | 0.53 | 1:200 |
| 1.00 | 27.92 | 0.76 | 8.32 | 0.74 | 1:400 |
| 0.50 | 40.47 | 0.68 | 7.91 | 0.55 | 1:800 |
| 0.25 | 33.53 | 0.72 | 11.65 | 0.50 | 1:1600 |
| 0.13 | 29.95 | 0.79 | 16.29 | 0.50 | 1:3200 |
| 0.06 | 18.22 | 0.34 | 10.87 | 0.54 | 1:6400 |
| 0.03 | 10.41 | 0.62 | 10.22 | 0.39 | 1:12800 |
| 0.02 | 4.91 | 0.79 | 7.29 | −0.19 | 1:25600 |
| 0.00 | 0.31 | −4.83 | 1.77 | −5.95 | 0.00 |

Optimal screening conditions for the immunodetection and epitope mapping of 1749.1.3 and Ms Sera were determined Using these conditions, each antibody demonstrated a robust signal, high signal-to-background values, and low variability between replicates. These data indicate that these conditions are suitable for successful high-throughput epitope mapping. Final screening concentrations of 0.5 µg/mL for 1749.1.3 and a 1:800 dilution of the Ms Sera were used. Secondary antibodies from Jackson ImmunoResearch were used at 1:400 for MAb and sera detection. Table 3 shows the experimental parameters optimized for high-throughput immunodetection.

TABLE 3

| Experimental Parameter | MAb 1749.1.3 | Ms Sera |
|---|---|---|
| Cells Fixative | BHK-S 4% PFA | BHK-S 4% PFA |
| Blocking Buffer | 10% Goat Serum | 10% Goat Serum |
| Primary Ab | 1749 | Sera |
| Ab name Target | MCAM | MCAM |
| Optimal Conc. | 0.5 ug/ml | 1:800 dilution |
| Incubation (RT) | 60 min | 60 min |
| Secondary Ab Target | Mouse IgG | Mouse IgG |
| Optimal Conc. | 1:400 (3.75 ug/ml) | 1:400 (3.75 ug/ml) |
| Incubation | 30 min | 30 min |
| Manufacturer Cat # Antibody ID | Jackson/ ImmunoResearch 115-545-003 Alexa Fluor® 488-AffiniPure Goat Anti-Mouse IgG (H + L) | Jackson/ ImmunoResearch 115-545-003 Alexa Fluor® 488-AffiniPure Goat Anti-Mouse IgG (H + L) |
| Washes | PBS ($CA^{2+}$, $Mg^{2+}$ free) | PBS ($CA^{2+}$, $Mg^{2+}$ free) |
| Signal:Background | 40:1 | 8:1 |

The mutation library was assayed for surface expression (mouse sera binding) and monoclonal antibody binding, in triplicate. Each raw data point was background-subtracted and normalized to the wild type MCAM reactivity values. The results are shown in FIG. 1. The mean monoclonal antibody binding value for each clone is plotted as a function of its mean surface expression value (FIG. 1, gray diamonds). Thresholds of <30% monoclonal antibody reactivity and >50% mouse sera binding were applied to identify clones (FIG. 1, black diamonds) that were negative for monoclonal antibody binding but positive for surface expression.

Critical residues for 1749.1.3 were identified by evaluating the mean monoclonal antibody reactivity of each clone compared to its overall surface expression (average serum reactivity). Residues involved in antibody binding were identified as those that were negative for monoclonal antibody binding (<30% WT) but positive for surface expression (>50% WT) (Table 4). The mean reactivity (and standard deviation) were determined for each critical residue.

TABLE 4

| Residue ID | Mutations | MAb 1749.1.3 | Ms Sera |
|---|---|---|---|
| 272 | C272A | 7.6 (4.7) | 54.5 (55.8) |
| 318 | Y318A | 7.1 (2.4) | 111.7 (9.2) |
| 320 | C320A | 9.3 (11.2) | 50 (54.6) |
| 340 | V340A | 8.7 (8.3) | 103.8 (71.3) |
| 377 | W377A | 13.7 (10.3) | 63.4 (18.9) |

The critical amino acids identified by shotgun mutagenesis mapping suggest binding sites for the 1749.1.3 antibody. The data indicate that 1749.1.3 binds a conformationally complex epitope at the third Ig domain of MCAM.

Critical residues appear largely dependent upon structural stabilization contributed by disulfide bonds of the second and/or third Ig domains. Mutation to either cysteine 272 or 320 abolishes antibody binding, suggesting the shared disulfide bond of the third Ig domain plays a significant role in stabilizing the epitope.

Example 5

Confirmatory MCAM Epitope Mapping for Antibody and Laminin Binding

Figure 2:
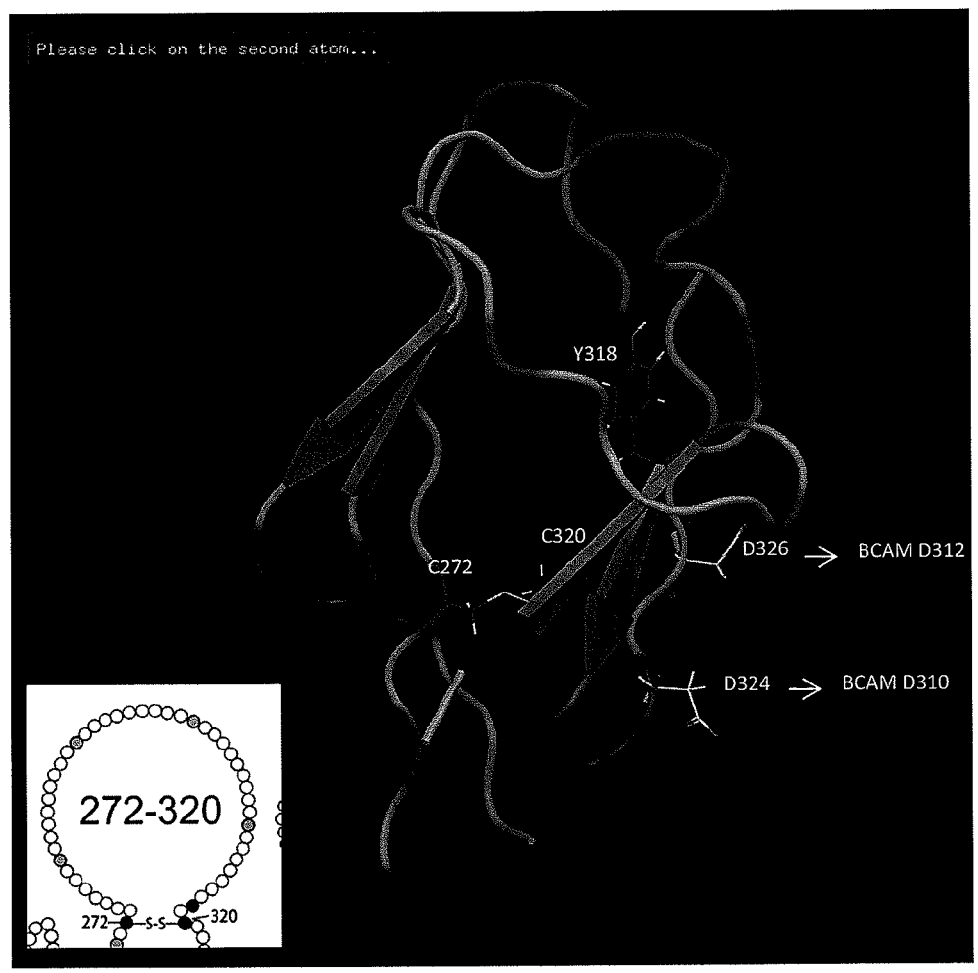
FIG. 2 depicts a homology model of human MCAM, indicating the location of five residues identified as potentially critical binding sites for 1749.1.3, including C272, Y318, C320, V340, and W377.

In order to identify 1749.1.3 binding sites on human MCAM, a homology model of human MCAM Ig3 was built up on pdb 3KVQ_A, 3V2A_R, 2IEP_A and 2YD1_A by using Schrodinger Maestro (FIG. 2). Twenty point mutants based on the structure information and shotgun mutagenesis information were designed and generated. These mutants were displayed on mammalian cells and FACS was used to test the binding of 1749.1.3 and laminin α-4 to the MCAM mutants. Three MCAM single mutants, I141A, D216A and Y318A, demonstrated a complete loss of laminin α-4 binding. The Y318A mutant demonstrated a complete loss of 1749.1.3 binding.

To further confirm the data, stable cell lines expressing I141A, P145V, D216A and Y318A respectively were generated. Fortebio assays were performed with the purified proteins as described above. The control ABX-MA1 antibody bound to wild type MCAM and the MCAM mutants. The 1749.1.3 antibody did not show significant binding to the MCAM Y318A mutant.

Example 6

Humanization of 1749.1.3 Antibodies

The starting point or donor antibody for humanization is the mouse antibody 1749 produced by a hybridoma described in WO201403997. The mature heavy chain variable amino acid and nucleic acid sequence of mature m1749 are provided as SEQ ID NOS:93 and 64, respectively. The mature light chain variable amino acid and nucleic acid sequences of mature m1749 are provided as SEQ ID NOS: 97 and 59, respectively. The heavy chain CDR1, CDR2, and CDR3 amino acid sequences are provided as SEQ ID NOs:66, 67, and 68, respectively. The light chain CDR1, CDR2, and CDR3 amino acid sequences are provided as SEQ ID NOs:61, 62, and 63, respectively. Kabat numbering is used throughout in this Example.

The variable kappa (Vk) of m1749 belongs to mouse Kabat subgroup 1 which corresponds to human Kabat subgroup 4. The variable heavy (Vh) of m1749 belongs to mouse Kabat subgroup 3d which corresponds to human Kabat subgroup 3 (Kabat et al. Sequences of Proteins of Immunological Interest, Fifth Edition. NIH Publication No. 91-3242, 1991). The 17 residue CDR-L1 belongs to canonical class 3, the 7 residue CDR-L2 belongs to canonical class 1, the 8 residue CDR-L3 belongs to canonical class 3 in Vk (Martin & Thornton, J Mol Biol. 263:800-15, 1996). The 5 residue CDR-H1 belongs to canonical class 1, the 17 residue CDR-H2 belongs to canonical class 1 or 3 (Martin & Thornton, J Mol Biol. 263:800-15, 1996). The CDR-H3 has no canonical classes, but the 11 residue loop probably has a kinked base according to the rules of Shirai et al., FEBS Lett. 455:188-97 (1999).

The residues at the interface between the Vk and Vh domains are the ones commonly found. A search was made over the protein sequences in the PDB database (Deshpande et al., Nucleic Acids Res. 33: D233-7, 2005) to find structures which would provide a rough structural model of 1749. The antibody against integral membrane protein DsbB in *E. coli* because has good overall sequence similarity to m1749 Vk, retaining the same canonical structures for the loops. The X-ray crystal structure of the anti-DsbB antibody (pdb code 2LTQ; Tang et al., J. Mol. Biol. 425:1670-82, 2013; SEQ ID NO:161) was used for the Vk structure in the modeling. The antibody directed against a peptide immunogen from influenza virus hemagglutinin has good overall sequence similarity to 1749 Vh structure. It also has a CDR-H3 of a similar length with a kinked base. The structure of the antibody directed against a peptide immunogen from influenza virus hemagglutinin (1HIL; Rini et al., Science 255: 959-65, 1992; SEQ ID NO:157) has reasonable resolution (2.0A), and was used for the Vh structure in the modeling. In addition, CDRs-H1 and H2 of 1H1L have the same canonical structures for CDR-H1 and CDR-H2 as that of 1749 Vh. BioLuminate® was used to model a rough structure of 1749Fv.

A search of the non-redundant protein sequence database from NCBI allowed selection of suitable human frameworks into which to graft the murine CDRs. For Vk, two human kappa light chains were chosen, the first with NCBI accession code ABA71407.1 (GI:77379502; SEQ ID NO:162) (Manske et al., Clin. Immunol. 120:106-20, 2006) and the second with NCBI accession code CAI99800.1 (GI: 98956324; SEQ ID NO:163) (Su et al., J. Immunol. 181: 1264-71, 2008). This has the same canonical classes for CDR-L1, L2, and L3. ABA71407.1 has a sequence identity of 85% in the light chain variable region framework to murine 1749 light chain. CAI99800.1 has a sequence identity of 83% in the light chain variable region framework to murine 1749 light chain.

For Vh, two human Ig heavy chains were chosen, the first with NCBI accession code AAX82494.1 (GI:62421461; SEQ ID NO:158) (Lundquist, Infect. Immun. 74:3222-31, 2006) and the second with NCBI accession code ADX65676.1 (GI:323432073; SEQ ID NO:159) (unpublished). It shares the canonical form of 1749 CDR-H1 and H2, and H3 is 11 residues long with a predicted kinked base. AAX82494.1 has a sequence identity of 91% in the variable region framework to murine 1749 heavy chain. ADX65676.1 has a sequence identity of 83% in the variable region framework to murine 1749 heavy chain.

A humanized light chain variable region variant and a humanized heavy chain variable region variant were constructed containing the above substitutions (Hu1749VHv3; SEQ ID NO:156, and Hu1749VLv3; SEQ ID NO:160) (FIGS. 3A & B). The amino acids at H3, H42, H93, L9, L19, L43 in Hu1749VHv3 and Hu1749VLv3 are listed in Table 5.

The rationales for selection of the above positions as candidates for substitution are as follows.

Q3K (here as elsewhere for framework backmutations, the first mentioned residue is the human residue and the second the mouse residue): K contacts Y102 in CDRH3. Therefore, it should be maintained in the framework.

G42E: E has similar side chain as D in human acceptor AAX82494.1. E is more frequent than D in humans. This backmutation contributes to protein stability.

A93T: This position is a Vk/Vh interface residue.

D9S: This residue does not contact or affect CDRs and/or interface. The frequency of S is greater than D in human framework regions.

A19V: The frequency of V and A are similar in human framework regions.

P43S: S contacts two interface residues in VH: Y91 and W103. Therefore, it is critical and should to be maintained in the framework.

>Hu1749VHv3
EVKLVESGGGLVQPGGSLRLSCAASGFTFSSYIMSWVRQTPEKRLEWV

ATISSGGSSTYYPDSVKGRFTISRDNAKNTLYLQMSSLKSEDTAMYYC

TRDDDYDVKVFAYWGQGTLVTVSS

>Hu1749VLv3
DIVMTQSPSSLAVSLGERVTINCKSSRSLLNSRIRKNYLAWYQQKPGQ

SPKLLIYWASTRESGVPDRFSGSGSGTDFTLTISSLQAEDVAVYYCKQ

SYNLLTFGQGTKVEIKR

Example 7

Characterization of Variant the Humanized 1749H3L3 Antibody

Binding kinetics of the humanized 1749 antibody comprising the heavy chain Hu1749VHv3 and the light chain Hu1749VLv3 have been characterized.

Binding kinetic of humanized 1749 antibodies were measured by bio-layer interferometry (BLI) using a ForteBio Octet QK instrument (ForteBio, Menlo Park, Calif.). Detailed binding kinetic parameters (association rate, apparent ka, dissociation rate, apparent kd, and affinity constant, apparent KD) were determined for chimeric 1749 and humanized 1749 antibodies (Table 6). Apparent ka, apparent kd and apparent $K_D$ are binding kinetic parameters obtained using ForteBio assay formats.

The hu1749H3L3 variant was found to give the lowest dissociation constant (highest association constant), the same as 1749.1.3 within the SEM.

TABLE 5

Kabat Numbering of Some Framework Residues for Backmutation in Humanized 1749 Antibodies

| Kabat Residue # | Linear Residue # | ABA71407.1 light chain | CAI99800.1 light chain | AAX82494.1 heavy chain | ADX65676.1 heavy chain | Mouse 1749 | Hu1749VLv3 | Hu1749VHv3 |
|---|---|---|---|---|---|---|---|---|
| H3 | 3 | — | — | Q | Q | K | — | K |
| H42 | 42 | — | — | D | G | E | — | E |
| H93 | 97 | — | — | A | A | T | — | T |
| L9 | 9 | D | D | — | — | S | S | — |
| L19 | 19 | A | A | — | — | V | V | — |
| L43 | 49 | P | P | — | — | S | S | — |

TABLE 6

Binding Kinetic Parameters of Murine 1749, Chimeric 1749, and Humanized 1749 Antibodies

| Antibody | Apparent $K_D$ M | Apparent $K_a$ (M$^{-1}$s$^{-1}$) | Apparent $K_d$ (s$^{-1}$) |
|---|---|---|---|
| Mouse 1749 | 2.86E−10 | 1.41E+6 | 4.02E−04 |
| Chimeric 1749 | 2.26E−10 | 1.94E+6 | 4.39E−04 |
| Human 1749VH3VL3 (Hu1749VHv3 and Hu1749VLv3) | 2.21E−10 | 1.99E+6 | 4.40E−04 |

In addition, Analysis with Dynamic Light Scattering (DLS) shows a level of polydiversity (% PD) of the h1749H3L3 antibody similar to that of the parental m1749 antibody (Table 7). Dynamic Light Scattering measurements were taken in a Wyatt DynaPro Nanostar Dynamic Light Scattering instrument, in 10 microliter size volumes within a quartz cuvette. All measurements were obtained at 37° C. with each measurement having 10 acquisitions with an acquisition time of 5 seconds. Regularization was done by the Wyatt Technology Dynamics 7.0 software using a Rayleigh Spheres model.

TABLE 7

DLS Analysis of 1749 Variants

| mAb | % Pd |
|---|---|
| h1749 WT | 68.8 |
| h1749 P43S | 64.6 |
| m1749 | 10.2 |
| ch1749 | 19.6 |
| h1749H3L3 | 22.0 |

What is claimed is:

1. A humanized antibody specifically binding to human MCAM comprising:
   (a) a mature heavy chain variable region comprising the three Kabat CDRs of SEQ ID NO:156, and being at least 97% identical to SEQ ID NO:156; and
   (b) a mature light chain variable region that has the amino acid sequence of SEQ ID NO:160.

2. The humanized antibody of claim 1, wherein the mature heavy chain variable region is at least 98% identical to SEQ ID NO:156.

3. The humanized antibody of claim 1, wherein the mature heavy chain variable region is at least 99% identical to SEQ ID NO:156.

4. A humanized antibody specifically binding to human MCAM comprising a mature heavy chain variable region that has the amino acid sequence of SEQ ID NO:156 and a mature light chain variable region comprising the three Kabat CDRs of SEQ ID NO:160, and being at least 97% identical to SEQ ID NO:160.

5. The humanized antibody of claim 4, wherein the mature light chain variable region is at least 98% identical to SEQ ID NO:160.

6. The humanized antibody of claim 4, wherein the mature light chain variable region is at least 99% identical to SEQ ID NO:160.

7. The humanized antibody of claim 1, wherein the mature heavy chain variable region has the amino acid sequence of SEQ ID NO:156 and the mature light chain variable region has the amino acid sequence of SEQ ID NO:160.

8. The humanized antibody of claim 1, further provided that position 3 (Kabat numbering) of the mature heavy chain variable region is occupied by K.

9. The humanized antibody of claim 1 or 8, further provided that position 93 (Kabat numbering) of the mature heavy chain variable region is occupied by T.

10. The humanized antibody of claim 1 or 8, further provided that position 42 (Kabat numbering) of the mature heavy chain variable region is occupied by E.

11. The humanized antibody of claim 4, further provided that position 43 (Kabat numbering) of the mature light chain variable region is occupied by S.

12. The humanized antibody of claim 4 or 11, further provided that position 9 (Kabat numbering) of the mature light heavy chain variable region is occupied by S.

13. The humanized antibody of claim 4 or 11, further provided that position 19 (Kabat numbering) of the mature light heavy chain variable region is occupied by V.

14. The humanized antibody of any one of claim 1, 4 or 7, which is an antigen-binding fragment.

15. A pharmaceutical composition comprising the humanized antibody of claim 1 or 4.

16. The humanized antibody of claim 1, wherein the mature heavy chain variable region has the amino acid sequence of SEQ ID NO:156 and the mature light chain variable region has the amino acid sequence of SEQ ID NO:160, and wherein the humanized antibody comprises a heavy chain constant region having the amino acid sequence of SEQ ID NO:173 provided the C-terminal lysine may be absent, and a light chain constant region having the amino acid sequence of SEQ ID NO:170.

17. The humanized antibody of claim 1, wherein the mature heavy chain variable region has the amino acid sequence of SEQ ID NO:156 and the mature light chain variable region has the amino acid sequence of SEQ ID NO:160, and wherein the humanized antibody comprises a heavy chain constant region having the amino acid sequence of SEQ ID NO:173 provided the C-terminal lysine may be absent, and a light chain constant region having the amino acid sequence of SEQ ID NO:171.

18. The humanized antibody of claim 1, wherein the mature heavy chain variable region has the amino acid sequence of SEQ ID NO:156 and the mature light chain variable region has the amino acid sequence of SEQ ID NO:160, and wherein the humanized antibody comprises a heavy chain constant region having the amino acid sequence of SEQ ID NO:174, provided the C-terminal lysine may be absent, and a light chain constant region having the amino acid sequence of SEQ ID NO:171.

19. The humanized antibody of claim 1, further provided that positions 42 and 93 (Kabat numbering) of the mature heavy chain variable region are occupied by E and T, respectively.

20. The humanized antibody of claim 4, further provided that positions 9 and 19 (Kabat numbering) of the mature light heavy chain variable region are occupied by S and V, respectively.

* * * * *

SEQUENCE LISTING

<160> NUMBER OF SEQ ID NOS: 179

<210> SEQ ID NO 1
<211> LENGTH: 428
<212> TYPE: DNA
<213> ORGANISM: Artificial Sequence
<220> FEATURE:
<223> OTHER INFORMATION: Synthetic

<400> SEQUENCE: 1

```
atgagggtcc agattcagtt tctggggctc cttctgctct ggacatcagt tgtccagtgt    60
gatgtccaga tgacccagtc tccatcttat cttgctacgt ctcctggaga gagtgtttcc   120
atcagttgca aggcaagtaa aaacattgac acatacttag cctggtatca ggagaaacct   180
gggaaaacga ataagcttct tatctactct gggtcaactt tgcaatctgg aactccatcg   240
agattcagtg gcagtggatc tggtacagat ttcacgctca ccatcagaaa cctggagtct   300
gaagattttg cagtctacta ctgtcaacag cataatgaat acccgctcac gttcggttct   360
gggaccaagc tggagatcaa acgggctgat gctgcaccaa ctgtatccat cttcccacca   420
tcctcgga                                                            428
```

<210> SEQ ID NO 2
<211> LENGTH: 142
<212> TYPE: PRT
<213> ORGANISM: Artificial Sequence
<220> FEATURE:
<223> OTHER INFORMATION: Synthetic

<400> SEQUENCE: 2

```
Met Arg Val Gln Ile Gln Phe Leu Gly Leu Leu Leu Leu Trp Thr Ser
1               5                   10                  15
Val Val Gln Cys Asp Val Gln Met Thr Gln Ser Pro Ser Tyr Leu Ala
            20                  25                  30
Thr Ser Pro Gly Glu Ser Val Ser Ile Ser Cys Lys Ala Ser Lys Asn
        35                  40                  45
Ile Asp Thr Tyr Leu Ala Trp Tyr Gln Glu Lys Pro Gly Lys Thr Asn
    50                  55                  60
Lys Leu Leu Ile Tyr Ser Gly Ser Thr Leu Gln Ser Gly Thr Pro Ser
65                  70                  75                  80
Arg Phe Ser Gly Ser Gly Ser Gly Thr Asp Phe Thr Leu Thr Ile Arg
                85                  90                  95
Asn Leu Glu Ser Glu Asp Phe Ala Val Tyr Tyr Cys Gln Gln His Asn
            100                 105                 110
Glu Tyr Pro Leu Thr Phe Gly Ser Gly Thr Lys Leu Glu Ile Lys Arg
        115                 120                 125
Ala Asp Ala Ala Pro Thr Val Ser Ile Phe Pro Pro Ser Ser
    130                 135                 140
```

<210> SEQ ID NO 3
<211> LENGTH: 11
<212> TYPE: PRT
<213> ORGANISM: Artificial Sequence
<220> FEATURE:
<223> OTHER INFORMATION: Synthetic

<400> SEQUENCE: 3

Lys Ala Ser Lys Asn Ile Asp Thr Tyr Leu Ala
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Synthetic

<400> SEQUENCE: 4

Ser Gly Ser Thr Leu
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Gln Gln His Asn Glu Tyr Pro Leu Thr
1               5

<210> SEQ ID NO 6
<211> LENGTH: 480
<212> TYPE: DNA
<213> ORGANISM: Artificial Sequence
<220> FEATURE:
<223> OTHER INFORMATION: Synthetic

<400> SEQUENCE: 6
atggacacca ggctctgctt ggttttcctt gtccttttca taaaaggtgt ccagtgtgag      60
gtgcagctgg tggagtctgg tggaggctta gtgcagcctg aaggtccct gaaactctcc     120 tgtgcagcct caggattcac tttcagtaac tattacatgg cctgggtccg ccaggctcca    180
acgaagggtc tggagtgggt cgcatccatt agttttgagg gtaatagaaa tcactatgga    240
gactccgtga agggccgaat cactatctcc agagataatg caaaaagcac cctatacctg    300
caaatgacca gtctgaggcc tgaggacacg gcctattatt gtgcaagaca tcggggggtat    360 agtacgaatt tttatcacga cgttttggat gcctggggtc aaggagcttt agtcactgtc    420
tcctcagctg aaacaacagc cccatctgtc tatccactgg ctcctggaac tgctctcaaa    480

<210> SEQ ID NO 7
<211> LENGTH: 161
<212> TYPE: PRT
<213> ORGANISM: Artificial Sequence
<220> FEATURE:
<223> OTHER INFORMATION: Synthesized

<400> SEQUENCE: 7

Met Asp Thr Arg Leu Cys Leu Val Phe Leu Val Leu Phe Ile Lys Gly
1               5                   10                  15

```
Val Gln Cys Glu Val Gln Leu Val Glu Ser Gly Gly Gly Leu Val Gln
             20                  25                  30

Pro Gly Arg Ser Leu Lys Leu Ser Cys Ala Ala Ser Gly Phe Thr Phe
         35                  40                  45

Ser Asn Tyr Tyr Met Ala Trp Val Arg Gln Ala Pro Thr Lys Gly Leu
     50                  55                  60

Glu Trp Val Ala Ser Ile Ser Phe Glu Gly Asn Arg Asn His Tyr Gly
 65                  70                  75                  80

Asp Ser Val Lys Gly Arg Ile Thr Ile Ser Arg Asp Asn Ala Lys Ser
                 85                  90                  95

Thr Leu Tyr Leu Gln Met Thr Ser Leu Arg Pro Glu Asp Thr Ala Thr
            100                 105                 110

Tyr Tyr Cys Ala Arg His Arg Gly Tyr Ser Thr Asn Phe Tyr His Asp
        115                 120                 125

Val Leu Asp Ala Trp Gly Gln Gly Ala Leu Val Thr Val Ser Ser Ala
    130                 135                 140

Glu Thr Thr Ala Pro Ser Val Tyr Pro Leu Ala Pro Gly Thr Ala Leu
145                 150                 155                 160

Lys

<210> SEQ ID NO 8
<211> LENGTH: 10
<212> TYPE: PRT
<213> ORGANISM: Artificial Sequence
<220> FEATURE:
<223> OTHER INFORMATION: Synthetic

<400> SEQUENCE: 8

Gly Phe Thr Phe Ser Asn Tyr Tyr Met Ala
1               5                   10

<210> SEQ ID NO 9
<211> LENGTH: 16
<212> TYPE: PRT
<213> ORGANISM: Artificial Sequence
<220> FEATURE:
<223> OTHER INFORMATION: Synthetic

<400> SEQUENCE: 9

Ser Ile Ser Phe Glu Gly Asn Arg Asn His Tyr Gly Asp Ser Val Lys
1               5                   10                  15

<210> SEQ ID NO 10
<211> LENGTH: 19
<212> TYPE: PRT
<213> ORGANISM: Artificial Sequence
<220> FEATURE:
<223> OTHER INFORMATION: Synthetic

<400> SEQUENCE: 10

His Arg Gly Tyr Ser Thr Asn Phe Tyr His Asp Val Leu Asp Ala Trp
1               5                   10                  15

Gly Gln Gly

<210> SEQ ID NO 11
<211> LENGTH: 646
<212> TYPE: PRT
<213> ORGANISM: Homo sapiens

<400> SEQUENCE: 11

Met Gly Leu Pro Arg Leu Val Cys Ala Phe Leu Leu Ala Ala Cys Cys
```

-continued

```
1               5                    10                   15
Cys Cys Pro Arg Val Ala Gly Val Pro Gly Glu Ala Glu Gln Pro Ala
                20                   25                  30
Pro Glu Leu Val Glu Val Glu Val Gly Ser Thr Ala Leu Leu Lys Cys
                35                   40                  45
Gly Leu Ser Gln Ser Gln Gly Asn Leu Ser His Val Asp Trp Phe Ser
                50                   55                  60
Val His Lys Glu Lys Arg Thr Leu Ile Phe Arg Val Arg Gln Gly Gln
65                   70                   75                  80
Gly Gln Ser Glu Pro Gly Glu Tyr Glu Gln Arg Leu Ser Leu Gln Asp
                85                   90                  95
Arg Gly Ala Thr Leu Ala Leu Thr Gln Val Thr Pro Gln Asp Glu Arg
                100                  105                 110
Ile Phe Leu Cys Gln Gly Lys Arg Pro Arg Ser Gln Glu Tyr Arg Ile
                115                  120                 125
Gln Leu Arg Val Tyr Lys Ala Pro Glu Glu Pro Asn Ile Gln Val Asn
                130                  135                 140
Pro Leu Gly Ile Pro Val Asn Ser Lys Glu Pro Glu Glu Val Ala Thr
145                  150                  155                 160
Cys Val Gly Arg Asn Gly Tyr Pro Ile Pro Gln Val Ile Trp Tyr Lys
                165                  170                 175
Asn Gly Arg Pro Leu Lys Glu Glu Lys Asn Arg Val His Ile Gln Ser
                180                  185                 190
Ser Gln Thr Val Glu Ser Ser Gly Leu Tyr Thr Leu Gln Ser Ile Leu
                195                  200                 205
Lys Ala Gln Leu Val Lys Glu Asp Lys Asp Ala Gln Phe Tyr Cys Glu
                210                  215                 220
Leu Asn Tyr Arg Leu Pro Ser Gly Asn His Met Lys Glu Ser Arg Glu
225                  230                  235                 240
Val Thr Val Pro Val Phe Tyr Pro Thr Glu Lys Val Trp Leu Glu Val
                245                  250                 255
Glu Pro Val Gly Met Leu Lys Glu Gly Asp Arg Val Glu Ile Arg Cys
                260                  265                 270
Leu Ala Asp Gly Asn Pro Pro His Phe Ser Ile Ser Lys Gln Asn
                275                  280                 285
Pro Ser Thr Arg Glu Ala Glu Glu Glu Thr Thr Asn Asp Asn Gly Val
                290                  295                 300
Leu Val Leu Glu Pro Ala Arg Lys Glu His Ser Gly Arg Tyr Glu Cys
305                  310                  315                 320
Gln Ala Trp Asn Leu Asp Thr Met Ile Ser Leu Leu Ser Glu Pro Gln
                325                  330                 335
Glu Leu Leu Val Asn Tyr Val Ser Asp Val Arg Val Ser Pro Ala Ala
                340                  345                 350
Pro Glu Arg Gln Glu Gly Ser Ser Leu Thr Leu Thr Cys Glu Ala Glu
                355                  360                 365
Ser Ser Gln Asp Leu Glu Phe Gln Trp Leu Arg Glu Glu Thr Asp Gln
                370                  375                 380
Val Leu Glu Arg Gly Pro Val Leu Gln Leu His Asp Leu Lys Arg Glu
385                  390                  395                 400
Ala Gly Gly Gly Tyr Arg Cys Val Ala Ser Val Pro Ser Ile Pro Gly
                405                  410                 415
Leu Asn Arg Thr Gln Leu Val Lys Leu Ala Ile Phe Gly Pro Pro Trp
                420                  425                 430
```

```
            Met Ala Phe Lys Glu Arg Lys Val Trp Val Lys Glu Asn Met Val Leu
                    435                 440                 445

Asn Leu Ser Cys Glu Ala Ser Gly His Pro Arg Pro Thr Ile Ser Trp
                450                 455                 460

Asn Val Asn Gly Thr Ala Ser Glu Gln Asp Gln Asp Pro Gln Arg Val
            465                 470                 475                 480

Leu Ser Thr Leu Asn Val Leu Val Thr Pro Glu Leu Leu Glu Thr Gly
                            485                 490                 495

Val Glu Cys Thr Ala Ser Asn Asp Leu Gly Lys Asn Thr Ser Ile Leu
                        500                 505                 510

Phe Leu Glu Leu Val Asn Leu Thr Thr Leu Thr Pro Asp Ser Asn Thr
                    515                 520                 525

Thr Thr Gly Leu Ser Thr Ser Thr Ala Ser Pro His Thr Arg Ala Asn
                530                 535                 540

Ser Thr Ser Thr Glu Arg Lys Leu Pro Glu Pro Glu Ser Arg Gly Val
            545                 550                 555                 560

Val Ile Val Ala Val Ile Val Cys Ile Leu Val Leu Ala Val Leu Gly
                            565                 570                 575

Ala Val Leu Tyr Phe Leu Tyr Lys Lys Gly Lys Leu Pro Cys Arg Arg
                        580                 585                 590

Ser Gly Lys Gln Glu Ile Thr Leu Pro Pro Ser Arg Lys Thr Glu Leu
                    595                 600                 605

Val Val Glu Val Lys Ser Asp Lys Leu Pro Glu Glu Met Gly Leu Leu
                610                 615                 620

Gln Gly Ser Ser Gly Asp Lys Arg Ala Pro Gly Asp Gln Gly Glu Lys
            625                 630                 635                 640

Tyr Ile Asp Leu Arg His
                            645

<210> SEQ ID NO 12
<211> LENGTH: 474
<212> TYPE: DNA
<213> ORGANISM: Artificial Sequence
<220> FEATURE:
<223> OTHER INFORMATION: Synthetic

<400> SEQUENCE: 12
atggaatcac agacccaggt cctcatgtcc ctgctgctct ggatttctgg tacctgtggg      60
gacattgtga tgacccagtc tccatcctct ctggctgtgt cagctgggga gacggtctct     120
atacactgca gtccagtca gagtcttta tacagtggaa cccaaaagaa ctacttggcc      180
tggttccagc agaaaccagg acagtctcct aaactgctga tcttctgggc atctactagg    240
cagtctggtg tccctgatcg cttcataggc cgtggatctg gacagactt cactctgacc     300 atcagcggtg tgcaggcaga gatctggca atttattact gtcaacaata ttatgatact     360
ctcacggaca cgtttggagc ggggaccaag ctggaactga acgggctga tgctgcacca     420 actgtatcta tcttcccacc atccacggaa cagttagcaa ctggaggtgc ctca         474

<210> SEQ ID NO 13
<211> LENGTH: 158
<212> TYPE: PRT
<213> ORGANISM: Artificial Sequence
<220> FEATURE:
<223> OTHER INFORMATION: Synthesized

<400> SEQUENCE: 13
```

```
Met Glu Ser Gln Thr Gln Val Leu Met Ser Leu Leu Leu Trp Ile Ser
1               5                   10                  15

Gly Thr Cys Gly Asp Ile Val Met Thr Gln Ser Pro Ser Ser Leu Ala
            20                  25                  30

Val Ser Ala Gly Glu Thr Val Ser Ile His Cys Lys Ser Ser Gln Ser
        35                  40                  45

Leu Leu Tyr Ser Gly Thr Gln Lys Asn Tyr Leu Ala Trp Phe Gln Gln
    50                  55                  60

Lys Pro Gly Gln Ser Pro Lys Leu Leu Ile Phe Trp Ala Ser Thr Arg
65                  70                  75                  80

Gln Ser Gly Val Pro Asp Arg Phe Ile Gly Arg Gly Ser Gly Thr Asp
                85                  90                  95

Phe Thr Leu Thr Ile Ser Gly Val Gln Ala Glu Asp Leu Ala Ile Tyr
            100                 105                 110

Tyr Cys Gln Gln Tyr Tyr Asp Thr Leu Thr Asp Thr Phe Gly Ala Gly
        115                 120                 125

Thr Lys Leu Glu Leu Lys Arg Ala Asp Ala Ala Pro Thr Val Ser Ile
    130                 135                 140

Phe Pro Pro Ser Thr Glu Gln Leu Ala Thr Gly Gly Ala Ser
145                 150                 155
```

<210> SEQ ID NO 14
<211> LENGTH: 17
<212> TYPE: PRT
<213> ORGANISM: Artificial Sequence
<220> FEATURE:
<223> OTHER INFORMATION: Synthetic

<400> SEQUENCE: 14

```
Lys Ser Ser Gln Ser Leu Leu Tyr Ser Gly Thr Gln Lys Asn Tyr Leu
1               5                   10                  15

Ala
```

<210> SEQ ID NO 15
<211> LENGTH: 7
<212> TYPE: PRT
<213> ORGANISM: Artificial Sequence
<220> FEATURE:
<223> OTHER INFORMATION: Synthetic

<400> SEQUENCE: 15

```
Trp Ala Ser Thr Arg Gln Ser
1               5
```

<210> SEQ ID NO 16
<211> LENGTH: 10
<212> TYPE: PRT
<213> ORGANISM: Artificial Sequence
<220> FEATURE:
<223> OTHER INFORMATION: Synthetic

<400> SEQUENCE: 16

```
Gln Gln Tyr Tyr Asp Thr Leu Thr Asp Thr
1               5                   10
```

<210> SEQ ID NO 17
<211> LENGTH: 469
<212> TYPE: DNA
<213> ORGANISM: Artificial Sequence
<220> FEATURE:
<223> OTHER INFORMATION: Synthetic

<400> SEQUENCE: 17

```
atggacatca ggctcagctt ggctttcctg gtccttttca taaaaggtgt ccagtgtgag      60
gtgcggctgg tggagtctgg gggaggctta gtgcagcctg gaaagtccat gaaactctcc     120
tgtgtagcct cgggattcaa attcagtaac tattacatgt cctgggtccg ccaggctcca     180
gcgaagggtc tggagtgggt cgcatccatt agtgatggtg gtggtgacac tttctgtcga     240
gacttggtga agggccgatt cactatctcc agagataatg caaaaagtac cctttacctg     300
caaatggaca gtctgaggcc tgaggacacg gccacttatt actgtgcaag acggggagca     360
gctatggggg gtgttatgga tgcctggggt caaggaactt cagtcactgt ctcctcagct     420
gaaacaacag ccccatctgt ctatccactg gctcctggaa ctgctctca               469
```

<210> SEQ ID NO 18
<211> LENGTH: 156
<212> TYPE: PRT
<213> ORGANISM: Artificial Sequence
<220> FEATURE:
<223> OTHER INFORMATION: Synthesized

<400> SEQUENCE: 18

```
Met Asp Ile Arg Leu Ser Leu Ala Phe Leu Val Leu Phe Ile Lys Gly
1               5                   10                  15
Val Gln Cys Glu Val Arg Leu Val Glu Ser Gly Gly Gly Leu Val Gln
            20                  25                  30
Pro Gly Lys Ser Met Lys Leu Ser Cys Val Ala Ser Gly Phe Lys Phe
        35                  40                  45
Ser Asn Tyr Tyr Met Ser Trp Val Arg Gln Ala Pro Ala Lys Gly Leu
    50                  55                  60
Glu Trp Val Ala Ser Ile Ser Asp Gly Gly Gly Asp Thr Phe Cys Arg
65                  70                  75                  80
Asp Leu Val Lys Gly Arg Phe Thr Ile Ser Arg Asp Asn Ala Lys Ser
                85                  90                  95
Thr Leu Tyr Leu Gln Met Asp Ser Leu Arg Pro Glu Asp Thr Ala Thr
            100                 105                 110
Tyr Tyr Cys Ala Arg Arg Gly Ala Ala Met Gly Gly Val Met Asp Ala
        115                 120                 125
Trp Gly Gln Gly Thr Ser Val Thr Val Ser Ser Ala Glu Thr Thr Ala
    130                 135                 140
Pro Ser Val Tyr Pro Leu Ala Pro Gly Thr Ala Leu
145                 150                 155
```

<210> SEQ ID NO 19
<211> LENGTH: 10
<212> TYPE: PRT
<213> ORGANISM: Artificial Sequence
<220> FEATURE:
<223> OTHER INFORMATION: Synthetic

<400> SEQUENCE: 19

```
Gly Phe Lys Phe Ser Asn Tyr Tyr Met Ser
1               5                   10
```

<210> SEQ ID NO 20
<211> LENGTH: 17
<212> TYPE: PRT
<213> ORGANISM: Artificial Sequence
<220> FEATURE:
<223> OTHER INFORMATION: Synthetic

```
<400> SEQUENCE: 20

Ser Ile Ser Asp Gly Gly Gly Asp Thr Phe Cys Arg Asp Leu Val Lys
1               5                   10                  15

Gly

<210> SEQ ID NO 21
<211> LENGTH: 15
<212> TYPE: PRT
<213> ORGANISM: Artificial Sequence
<220> FEATURE:
<223> OTHER INFORMATION: Synthetic

<400> SEQUENCE: 21

Arg Gly Ala Ala Met Gly Gly Val Met Asp Ala Trp Gly Gln Gly
1               5                   10                  15

<210> SEQ ID NO 22
<211> LENGTH: 111
<212> TYPE: PRT
<213> ORGANISM: Homo sapiens

<400> SEQUENCE: 22

Pro Arg Val Ala Gly Val Pro Gly Glu Ala Glu Gln Pro Ala Pro Glu
1               5                   10                  15

Leu Val Glu Val Glu Val Gly Ser Thr Ala Leu Leu Lys Cys Gly Leu
            20                  25                  30

Ser Gln Ser Gln Gly Asn Leu Ser His Val Asp Trp Phe Ser Val His
        35                  40                  45

Lys Glu Lys Arg Thr Leu Ile Phe Arg Val Arg Gln Gly Gln Gly Gln
    50                  55                  60

Ser Glu Pro Gly Glu Tyr Glu Gln Arg Leu Ser Leu Gln Asp Arg Gly
65                  70                  75                  80

Ala Thr Leu Ala Leu Thr Gln Val Thr Pro Gln Asp Glu Arg Ile Phe
                85                  90                  95

Leu Cys Gln Gly Lys Arg Pro Arg Ser Gln Glu Tyr Arg Ile Gln
            100                 105                 110

<210> SEQ ID NO 23
<211> LENGTH: 104
<212> TYPE: PRT
<213> ORGANISM: Homo sapiens

<400> SEQUENCE: 23

Pro Asn Ile Gln Val Asn Pro Leu Gly Ile Pro Val Asn Ser Lys Glu
1               5                   10                  15

Pro Glu Glu Val Ala Thr Cys Val Gly Arg Asn Gly Tyr Pro Ile Pro
            20                  25                  30

Gln Val Ile Trp Tyr Lys Asn Gly Arg Pro Leu Lys Glu Glu Lys Asn
        35                  40                  45

Arg Val His Ile Gln Ser Ser Gln Thr Val Glu Ser Ser Gly Leu Tyr
    50                  55                  60

Thr Leu Gln Ser Ile Leu Lys Ala Gln Leu Val Lys Glu Asp Lys Asp
65                  70                  75                  80

Ala Gln Phe Tyr Cys Glu Leu Asn Tyr Arg Leu Pro Ser Gly Asn His
                85                  90                  95

Met Lys Glu Ser Arg Glu Val Thr
            100
```

<210> SEQ ID NO 24
<211> LENGTH: 78
<212> TYPE: PRT
<213> ORGANISM: Homo sapiens

<400> SEQUENCE: 24

Pro Val Phe Tyr Pro Thr Glu Lys Val Trp Leu Glu Val Glu Pro Val
1               5                   10                  15

Gly Met Leu Lys Glu Gly Asp Arg Val Glu Ile Arg Cys Leu Ala Asp
            20                  25                  30

Gly Asn Pro Pro Pro His Phe Ser Ile Ser Lys Gln Asn Pro Ser Thr
        35                  40                  45

Arg Glu Ala Glu Glu Thr Thr Asn Asp Asn Gly Val Leu Val Leu
50                  55                  60

Glu Pro Ala Arg Lys Glu His Ser Gly Arg Tyr Glu Cys Gln
65                  70                  75

<210> SEQ ID NO 25
<211> LENGTH: 90
<212> TYPE: PRT
<213> ORGANISM: Homo sapiens

<400> SEQUENCE: 25

Pro Gln Glu Leu Leu Val Asn Tyr Val Ser Asp Val Arg Val Ser Pro
1               5                   10                  15

Ala Ala Pro Glu Arg Gln Glu Gly Ser Ser Leu Thr Leu Thr Cys Glu
            20                  25                  30

Ala Glu Ser Ser Gln Asp Leu Glu Phe Gln Trp Leu Arg Glu Glu Thr
        35                  40                  45

Asp Gln Val Leu Glu Arg Gly Pro Val Leu Gln Leu His Asp Leu Lys
50                  55                  60

Arg Glu Ala Gly Gly Gly Tyr Arg Cys Val Ala Ser Val Pro Ser Ile
65                  70                  75                  80

Pro Gly Leu Asn Arg Thr Gln Leu Val Lys
                85                  90

<210> SEQ ID NO 26
<211> LENGTH: 81
<212> TYPE: PRT
<213> ORGANISM: Homo sapiens

<400> SEQUENCE: 26

Pro Pro Trp Met Ala Phe Lys Glu Arg Lys Val Trp Val Lys Glu Asn
1               5                   10                  15

Met Val Leu Asn Leu Ser Cys Glu Ala Ser Gly His Pro Arg Pro Thr
            20                  25                  30

Ile Ser Trp Asn Val Asn Gly Thr Ala Ser Glu Gln Asp Gln Asp Pro
        35                  40                  45

Gln Arg Val Leu Ser Thr Leu Asn Val Leu Val Thr Pro Glu Leu Leu
50                  55                  60

Glu Thr Gly Val Glu Cys Thr Ala Ser Asn Asp Leu Gly Lys Asn Thr
65                  70                  75                  80

Ser

<210> SEQ ID NO 27
<211> LENGTH: 1823
<212> TYPE: PRT
<213> ORGANISM: Homo sapiens

<400> SEQUENCE: 27

```
Met Ala Leu Ser Ser Ala Trp Arg Ser Val Leu Pro Leu Trp Leu Leu
  1               5                  10                  15

Trp Ser Ala Ala Cys Ser Arg Ala Ala Ser Gly Asp Asp Asn Ala Phe
             20                  25                  30

Pro Phe Asp Ile Glu Gly Ser Ser Ala Val Gly Arg Gln Asp Pro Pro
         35                  40                  45

Glu Thr Ser Glu Pro Arg Val Ala Leu Gly Arg Leu Pro Pro Ala Ala
     50                  55                  60

Glu Lys Cys Asn Ala Gly Phe Phe His Thr Leu Ser Gly Glu Cys Val
 65                  70                  75                  80

Pro Cys Asp Cys Asn Gly Asn Ser Asn Glu Cys Leu Asp Gly Ser Gly
                 85                  90                  95

Tyr Cys Val His Cys Gln Arg Asn Thr Thr Gly Glu His Cys Glu Lys
            100                 105                 110

Cys Leu Asp Gly Tyr Ile Gly Asp Ser Ile Arg Gly Ala Pro Gln Phe
        115                 120                 125

Cys Gln Pro Cys Pro Cys Pro Leu Pro His Leu Ala Asn Phe Ala Glu
    130                 135                 140

Ser Cys Tyr Arg Lys Asn Gly Ala Val Arg Cys Ile Cys Asn Glu Asn
145                 150                 155                 160

Tyr Ala Gly Pro Asn Cys Glu Arg Cys Ala Pro Gly Tyr Tyr Gly Asn
                165                 170                 175

Pro Leu Leu Ile Gly Ser Thr Cys Lys Lys Cys Asp Cys Ser Gly Asn
            180                 185                 190

Ser Asp Pro Asn Leu Ile Phe Glu Asp Cys Asp Glu Val Thr Gly Gln
        195                 200                 205

Cys Arg Asn Cys Leu Arg Asn Thr Thr Gly Phe Lys Cys Glu Arg Cys
    210                 215                 220

Ala Pro Gly Tyr Tyr Gly Asp Ala Arg Ile Ala Lys Asn Cys Ala Val
225                 230                 235                 240

Cys Asn Cys Gly Gly Gly Pro Cys Asp Ser Val Thr Gly Glu Cys Leu
                245                 250                 255

Glu Glu Gly Phe Glu Pro Pro Thr Gly Met Asp Cys Pro Thr Ile Ser
            260                 265                 270

Cys Asp Lys Cys Val Trp Asp Leu Thr Asp Asp Leu Arg Leu Ala Ala
        275                 280                 285

Leu Ser Ile Glu Glu Gly Lys Ser Gly Val Leu Ser Val Ser Ser Gly
    290                 295                 300

Ala Ala Ala His Arg His Val Asn Glu Ile Asn Ala Thr Ile Tyr Leu
305                 310                 315                 320

Leu Lys Thr Lys Leu Ser Glu Arg Glu Asn Gln Tyr Ala Leu Arg Lys
                325                 330                 335

Ile Gln Ile Asn Asn Ala Glu Asn Thr Met Lys Ser Leu Leu Ser Asp
            340                 345                 350

Val Glu Glu Leu Val Glu Lys Glu Asn Gln Ala Ser Arg Lys Gly Gln
        355                 360                 365

Leu Val Gln Lys Glu Ser Met Asp Thr Ile Asn His Ala Ser Gln Leu
    370                 375                 380

Val Glu Gln Ala His Asp Met Arg Asp Lys Ile Gln Glu Ile Asn Asn
385                 390                 395                 400

Lys Met Leu Tyr Tyr Gly Glu Glu His Glu Leu Ser Pro Lys Glu Ile
                405                 410                 415
```

-continued

```
Ser Glu Lys Leu Val Leu Ala Gln Lys Met Leu Glu Ile Arg Ser
            420                 425                 430

Arg Gln Pro Phe Phe Thr Gln Arg Glu Leu Val Asp Glu Ala Asp
            435                 440                 445

Glu Ala Tyr Glu Leu Leu Ser Gln Ala Glu Ser Trp Gln Arg Leu His
            450                 455                 460

Asn Glu Thr Arg Thr Leu Phe Pro Val Val Leu Glu Gln Leu Asp Asp
465                 470                 475                 480

Tyr Asn Ala Lys Leu Ser Asp Leu Gln Glu Ala Leu Asp Gln Ala Leu
                    485                 490                 495

Asn Tyr Val Arg Asp Ala Glu Asp Met Asn Arg Ala Thr Ala Ala Arg
                    500                 505                 510

Gln Arg Asp His Glu Lys Gln Gln Glu Arg Val Arg Glu Gln Met Glu
            515                 520                 525

Val Val Asn Met Ser Leu Ser Thr Ser Ala Asp Ser Leu Thr Thr Pro
530                 535                 540

Arg Leu Thr Leu Ser Glu Leu Asp Asp Ile Ile Lys Asn Ala Ser Gly
545                 550                 555                 560

Ile Tyr Ala Glu Ile Asp Gly Ala Lys Ser Glu Leu Gln Val Lys Leu
                565                 570                 575

Ser Asn Leu Ser Asn Leu Ser His Asp Leu Val Gln Glu Ala Ile Asp
                580                 585                 590

His Ala Gln Asp Leu Gln Gln Glu Ala Asn Glu Leu Ser Arg Lys Leu
            595                 600                 605

His Ser Ser Asp Met Asn Gly Leu Val Gln Lys Ala Leu Asp Ala Ser
            610                 615                 620

Asn Val Tyr Glu Asn Ile Val Asn Tyr Val Ser Glu Ala Asn Glu Thr
625                 630                 635                 640

Ala Glu Phe Ala Leu Asn Thr Thr Asp Arg Ile Tyr Asp Ala Val Ser
                    645                 650                 655

Gly Ile Asp Thr Gln Ile Ile Tyr His Lys Asp Glu Ser Glu Asn Leu
                660                 665                 670

Leu Asn Gln Ala Arg Glu Leu Gln Ala Lys Ala Glu Ser Ser Ser Asp
            675                 680                 685

Glu Ala Val Ala Asp Thr Ser Arg Arg Val Gly Gly Ala Leu Ala Arg
            690                 695                 700

Lys Ser Ala Leu Lys Thr Arg Leu Ser Asp Ala Val Lys Gln Leu Gln
705                 710                 715                 720

Ala Ala Glu Arg Gly Asp Ala Gln Gln Arg Leu Gly Gln Ser Arg Leu
                    725                 730                 735

Ile Thr Glu Glu Ala Asn Arg Thr Thr Met Glu Val Gln Gln Ala Thr
                740                 745                 750

Ala Pro Met Ala Asn Asn Leu Thr Asn Trp Ser Gln Asn Leu Gln His
            755                 760                 765

Phe Asp Ser Ser Ala Tyr Asn Thr Ala Val Asn Ser Ala Arg Asp Ala
770                 775                 780

Val Arg Asn Leu Thr Glu Val Val Pro Gln Leu Leu Asp Gln Leu Arg
785                 790                 795                 800

Thr Val Glu Gln Lys Arg Pro Ala Ser Asn Val Ser Ala Ser Ile Gln
                    805                 810                 815

Arg Ile Arg Glu Leu Ile Ala Gln Thr Arg Ser Val Ala Ser Lys Ile
                820                 825                 830
```

-continued

```
Gln Val Ser Met Met Phe Asp Gly Gln Ser Ala Val Glu Val His Ser
            835                 840                 845

Arg Thr Ser Met Asp Asp Leu Lys Ala Phe Thr Ser Leu Ser Leu Tyr
850                 855                 860

Met Lys Pro Pro Val Lys Arg Pro Glu Leu Thr Glu Thr Ala Asp Gln
865                 870                 875                 880

Phe Ile Leu Tyr Leu Gly Ser Lys Asn Ala Lys Lys Glu Tyr Met Gly
                885                 890                 895

Leu Ala Ile Lys Asn Asp Asn Leu Val Tyr Val Tyr Asn Leu Gly Thr
                900                 905                 910

Lys Asp Val Glu Ile Pro Leu Asp Ser Lys Pro Val Ser Ser Trp Pro
                915                 920                 925

Ala Tyr Phe Ser Ile Val Lys Ile Glu Arg Val Gly Lys His Gly Lys
                930                 935                 940

Val Phe Leu Thr Val Pro Ser Leu Ser Ser Thr Ala Glu Glu Lys Phe
945                 950                 955                 960

Ile Lys Lys Gly Glu Phe Ser Gly Asp Asp Ser Leu Leu Asp Leu Asp
                965                 970                 975

Pro Glu Asp Thr Val Phe Tyr Val Gly Gly Val Pro Ser Asn Phe Lys
                980                 985                 990

Leu Pro Thr Ser Leu Asn Leu Pro Gly Phe Val Gly Cys Leu Glu Leu
                995                 1000                1005

Ala Thr Leu Asn Asn Asp Val Ile Ser Leu Tyr Asn Phe Lys His Ile
                1010                1015                1020

Tyr Asn Met Asp Pro Ser Thr Ser Val Pro Cys Ala Arg Asp Lys Leu
1025                1030                1035                1040

Ala Phe Thr Gln Ser Arg Ala Ala Ser Tyr Phe Phe Asp Gly Ser Gly
                1045                1050                1055

Tyr Ala Val Val Arg Asp Ile Thr Arg Arg Gly Lys Phe Gly Gln Val
                1060                1065                1070

Thr Arg Phe Asp Ile Glu Val Arg Thr Pro Ala Asp Asn Gly Leu Ile
                1075                1080                1085

Leu Leu Met Val Asn Gly Ser Met Phe Phe Arg Leu Glu Met Arg Asn
                1090                1095                1100

Gly Tyr Leu His Val Phe Tyr Asp Phe Gly Phe Ser Gly Gly Pro Val
1105                1110                1115                1120

His Leu Glu Asp Thr Leu Lys Lys Ala Gln Ile Asn Asp Ala Lys Tyr
                1125                1130                1135

His Glu Ile Ser Ile Ile Tyr His Asn Asp Lys Lys Met Ile Leu Val
                1140                1145                1150

Val Asp Arg Arg His Val Lys Ser Met Asp Asn Glu Lys Met Lys Ile
                1155                1160                1165

Pro Phe Thr Asp Ile Tyr Ile Gly Gly Ala Pro Pro Glu Ile Leu Gln
                1170                1175                1180

Ser Arg Ala Leu Arg Ala His Leu Pro Leu Asp Ile Asn Phe Arg Gly
1185                1190                1195                1200

Cys Met Lys Gly Phe Gln Phe Gln Lys Lys Asp Phe Asn Leu Leu Glu
                1205                1210                1215

Gln Thr Glu Thr Leu Gly Val Gly Tyr Gly Cys Pro Glu Asp Ser Leu
                1220                1225                1230

Ile Ser Arg Arg Ala Tyr Phe Asn Gly Gln Ser Phe Ile Ala Ser Ile
                1235                1240                1245

Gln Lys Ile Ser Phe Phe Asp Gly Phe Glu Gly Gly Phe Asn Phe Arg
```

```
                1250                1255                1260
Thr Leu Gln Pro Asn Gly Leu Leu Phe Tyr Tyr Ala Ser Gly Ser Asp
1265                1270                1275                1280

Val Phe Ser Ile Ser Leu Asp Asn Gly Thr Val Ile Met Asp Val Lys
            1285                1290                1295

Gly Ile Lys Val Gln Ser Val Asp Lys Gln Tyr Asn Asp Gly Leu Ser
        1300                1305                1310

His Phe Val Ile Ser Ser Val Ser Pro Thr Arg Tyr Glu Leu Ile Val
    1315                1320                1325

Asp Lys Ser Arg Val Gly Ser Lys Asn Pro Thr Lys Gly Lys Ile Glu
1330                1335                1340

Gln Thr Gln Ala Ser Glu Lys Lys Phe Tyr Phe Gly Gly Ser Pro Ile
1345                1350                1355                1360

Ser Ala Gln Tyr Ala Asn Phe Thr Gly Cys Ile Ser Asn Ala Tyr Phe
            1365                1370                1375

Thr Arg Val Asp Arg Asp Val Glu Val Glu Asp Phe Gln Arg Tyr Thr
        1380                1385                1390

Glu Lys Val His Thr Ser Leu Tyr Glu Cys Pro Ile Glu Ser Ser Pro
    1395                1400                1405

Leu Phe Leu Leu His Lys Lys Gly Lys Asn Leu Ser Lys Pro Lys Ala
    1410                1415                1420

Ser Gln Asn Lys Lys Gly Gly Lys Ser Lys Asp Ala Pro Ser Trp Asp
1425                1430                1435                1440

Pro Val Ala Leu Lys Leu Pro Glu Arg Asn Thr Pro Arg Asn Ser His
            1445                1450                1455

Cys His Leu Ser Asn Ser Pro Arg Ala Ile Glu His Ala Tyr Gln Tyr
        1460                1465                1470

Gly Gly Thr Ala Asn Ser Arg Gln Glu Phe Glu His Leu Lys Gly Asp
    1475                1480                1485

Phe Gly Ala Lys Ser Gln Phe Ser Ile Arg Leu Arg Thr Arg Ser Ser
    1490                1495                1500

His Gly Met Ile Phe Tyr Val Ser Asp Gln Glu Glu Asn Asp Phe Met
1505                1510                1515                1520

Thr Leu Phe Leu Ala His Gly Arg Leu Val Tyr Met Phe Asn Val Gly
            1525                1530                1535

His Lys Lys Leu Lys Ile Arg Ser Gln Glu Lys Tyr Asn Asp Gly Leu
        1540                1545                1550

Trp His Asp Val Ile Phe Ile Arg Glu Arg Ser Ser Gly Arg Leu Val
    1555                1560                1565

Ile Asp Gly Leu Arg Val Leu Glu Glu Ser Leu Pro Pro Thr Glu Ala
    1570                1575                1580

Thr Trp Lys Ile Lys Gly Pro Ile Tyr Leu Gly Gly Val Ala Pro Gly
1585                1590                1595                1600

Lys Ala Val Lys Asn Val Gln Ile Asn Ser Ile Tyr Ser Phe Ser Gly
            1605                1610                1615

Cys Leu Ser Asn Leu Gln Leu Asn Gly Ala Ser Ile Thr Ser Ala Ser
        1620                1625                1630

Gln Thr Phe Ser Val Thr Pro Cys Phe Glu Gly Pro Met Glu Thr Gly
    1635                1640                1645

Thr Tyr Phe Ser Thr Glu Gly Gly Tyr Val Val Leu Asp Glu Ser Phe
    1650                1655                1660

Asn Ile Gly Leu Lys Phe Glu Ile Ala Phe Glu Val Arg Pro Arg Ser
1665                1670                1675                1680
```

```
Ser Ser Gly Thr Leu Val His Gly His Ser Val Asn Gly Glu Tyr Leu
            1685                1690                1695

Asn Val His Met Lys Asn Gly Gln Val Ile Val Lys Val Asn Asn Gly
        1700                1705                1710

Ile Arg Asp Phe Ser Thr Ser Val Thr Pro Lys Gln Ser Leu Cys Asp
            1715                1720                1725

Gly Arg Trp His Arg Ile Thr Val Ile Arg Asp Ser Asn Val Val Gln
            1730                1735                1740

Leu Asp Val Asp Ser Glu Val Asn His Val Val Gly Pro Leu Asn Pro
1745                1750                1755                1760

Lys Pro Ile Asp His Arg Glu Pro Val Phe Val Gly Val Pro Glu
            1765                1770                1775

Ser Leu Leu Thr Pro Arg Leu Ala Pro Ser Lys Pro Phe Thr Gly Cys
            1780                1785                1790

Ile Arg His Phe Val Ile Asp Gly His Pro Val Ser Phe Ser Lys Ala
            1795                1800                1805

Ala Leu Val Ser Gly Ala Val Ser Ile Asn Ser Cys Pro Ala Ala
        1810                1815                1820
```

<210> SEQ ID NO 28
<211> LENGTH: 1816
<212> TYPE: PRT
<213> ORGANISM: Homo sapiens

<400> SEQUENCE: 28

```
Met Ala Leu Ser Ser Ala Trp Arg Ser Val Pro Leu Trp Leu Leu
1               5                   10                  15

Trp Ser Ala Ala Cys Ser Arg Ala Ala Ser Gly Asp Asp Asn Ala Phe
            20                  25                  30

Pro Phe Asp Ile Glu Gly Ser Ser Ala Val Gly Arg Gln Asp Pro Pro
        35                  40                  45

Glu Thr Ser Glu Pro Arg Val Ala Leu Gly Arg Leu Pro Pro Ala Ala
    50                  55                  60

Glu Lys Cys Asn Ala Gly Phe Phe His Thr Leu Ser Gly Glu Cys Val
65              70                  75                  80

Pro Cys Asp Cys Asn Gly Asn Ser Asn Glu Cys Leu Asp Gly Ser Gly
                85                  90                  95

Tyr Cys Val His Cys Gln Arg Asn Thr Thr Gly Glu His Cys Glu Lys
            100                 105                 110

Cys Leu Asp Gly Tyr Ile Gly Asp Ser Ile Arg Gly Ala Pro Gln Phe
        115                 120                 125

Cys Gln Pro Cys Pro Cys Pro Leu Pro His Leu Ala Asn Phe Ala Glu
    130                 135                 140

Ser Cys Tyr Arg Lys Asn Gly Ala Val Arg Cys Ile Cys Asn Glu Asn
145             150                 155                 160

Tyr Ala Gly Pro Asn Cys Glu Arg Cys Ala Pro Gly Tyr Tyr Gly Asn
                165                 170                 175

Pro Leu Leu Ile Gly Ser Thr Cys Lys Lys Cys Asp Cys Ser Gly Asn
            180                 185                 190

Ser Asp Pro Asn Leu Ile Phe Glu Asp Cys Asp Glu Val Thr Gly Gln
        195                 200                 205

Cys Arg Asn Cys Leu Arg Asn Thr Thr Gly Phe Lys Cys Glu Arg Cys
    210                 215                 220

Ala Pro Gly Tyr Tyr Gly Asp Ala Arg Ile Ala Lys Asn Cys Ala Val
```

-continued

```
                225                 230                 235                 240
        Cys Asn Cys Gly Gly Gly Pro Cys Asp Ser Val Thr Gly Glu Cys Leu
                        245                 250                 255
        Glu Glu Gly Phe Glu Pro Pro Thr Gly Cys Asp Lys Cys Val Trp Asp
                        260                 265                 270
        Leu Thr Asp Asp Leu Arg Leu Ala Ala Leu Ser Ile Glu Glu Gly Lys
                        275                 280                 285
        Ser Gly Val Leu Ser Val Ser Ser Gly Ala Ala His Arg His Val
            290                 295                 300
        Asn Glu Ile Asn Ala Thr Ile Tyr Leu Leu Lys Thr Lys Leu Ser Glu
        305                 310                 315                 320
        Arg Glu Asn Gln Tyr Ala Leu Arg Lys Ile Gln Ile Asn Asn Ala Glu
                        325                 330                 335
        Asn Thr Met Lys Ser Leu Leu Ser Asp Val Glu Glu Leu Val Glu Lys
                        340                 345                 350
        Glu Asn Gln Ala Ser Arg Lys Gly Gln Leu Val Gln Lys Glu Ser Met
                        355                 360                 365
        Asp Thr Ile Asn His Ala Ser Gln Leu Val Glu Gln Ala His Asp Met
            370                 375                 380
        Arg Asp Lys Ile Gln Glu Ile Asn Asn Lys Met Leu Tyr Tyr Gly Glu
        385                 390                 395                 400
        Glu His Glu Leu Ser Pro Lys Glu Ile Ser Lys Leu Val Leu Ala
                        405                 410                 415
        Gln Lys Met Leu Glu Glu Ile Arg Ser Arg Gln Pro Phe Phe Thr Gln
                        420                 425                 430
        Arg Glu Leu Val Asp Glu Glu Ala Asp Glu Ala Tyr Glu Leu Leu Ser
                        435                 440                 445
        Gln Ala Glu Ser Trp Gln Arg Leu His Asn Glu Thr Arg Thr Leu Phe
            450                 455                 460
        Pro Val Val Leu Glu Gln Leu Asp Asp Tyr Asn Ala Lys Leu Ser Asp
        465                 470                 475                 480
        Leu Gln Glu Ala Leu Asp Gln Ala Leu Asn Tyr Val Arg Asp Ala Glu
                        485                 490                 495
        Asp Met Asn Arg Ala Thr Ala Ala Arg Gln Arg Asp His Glu Lys Gln
                        500                 505                 510
        Gln Glu Arg Val Arg Glu Gln Met Glu Val Val Asn Met Ser Leu Ser
                        515                 520                 525
        Thr Ser Ala Asp Ser Leu Thr Thr Pro Arg Leu Thr Leu Ser Glu Leu
            530                 535                 540
        Asp Asp Ile Ile Lys Asn Ala Ser Gly Ile Tyr Ala Glu Ile Asp Gly
        545                 550                 555                 560
        Ala Lys Ser Glu Leu Gln Val Lys Leu Ser Asn Leu Ser Asn Leu Ser
                        565                 570                 575
        His Asp Leu Val Gln Glu Ala Ile Asp His Ala Gln Asp Leu Gln Gln
                        580                 585                 590
        Glu Ala Asn Glu Leu Ser Arg Lys Leu His Ser Ser Asp Met Asn Gly
                        595                 600                 605
        Leu Val Gln Lys Ala Leu Asp Ala Ser Asn Val Tyr Glu Asn Ile Val
                        610                 615                 620
        Asn Tyr Val Ser Glu Ala Asn Glu Thr Ala Glu Phe Ala Leu Asn Thr
        625                 630                 635                 640
        Thr Asp Arg Ile Tyr Asp Ala Val Ser Gly Ile Asp Thr Gln Ile Ile
                        645                 650                 655
```

-continued

Tyr His Lys Asp Glu Ser Glu Asn Leu Leu Asn Gln Ala Arg Glu Leu
            660                 665                 670

Gln Ala Lys Ala Glu Ser Ser Asp Glu Ala Val Ala Asp Thr Ser
        675                 680                 685

Arg Arg Val Gly Gly Ala Leu Ala Arg Lys Ser Ala Leu Lys Thr Arg
690                 695                 700

Leu Ser Asp Ala Val Lys Gln Leu Gln Ala Ala Glu Arg Gly Asp Ala
705                 710                 715                 720

Gln Gln Arg Leu Gly Gln Ser Arg Leu Ile Thr Glu Ala Asn Arg
            725                 730                 735

Thr Thr Met Glu Val Gln Gln Ala Thr Ala Pro Met Ala Asn Asn Leu
                740                 745                 750

Thr Asn Trp Ser Gln Asn Leu Gln His Phe Asp Ser Ser Ala Tyr Asn
            755                 760                 765

Thr Ala Val Asn Ser Ala Arg Asp Ala Val Arg Asn Leu Thr Glu Val
    770                 775                 780

Val Pro Gln Leu Leu Asp Gln Leu Arg Thr Val Glu Gln Lys Arg Pro
785                 790                 795                 800

Ala Ser Asn Val Ser Ala Ser Ile Gln Arg Ile Arg Glu Leu Ile Ala
                805                 810                 815

Gln Thr Arg Ser Val Ala Ser Lys Ile Gln Val Ser Met Met Phe Asp
            820                 825                 830

Gly Gln Ser Ala Val Glu Val His Ser Arg Thr Ser Met Asp Asp Leu
            835                 840                 845

Lys Ala Phe Thr Ser Leu Ser Leu Tyr Met Lys Pro Pro Val Lys Arg
    850                 855                 860

Pro Glu Leu Thr Glu Thr Ala Asp Gln Phe Ile Leu Tyr Leu Gly Ser
865                 870                 875                 880

Lys Asn Ala Lys Lys Glu Tyr Met Gly Leu Ala Ile Lys Asn Asp Asn
                885                 890                 895

Leu Val Tyr Val Tyr Asn Leu Gly Thr Lys Asp Val Glu Ile Pro Leu
            900                 905                 910

Asp Ser Lys Pro Val Ser Ser Trp Pro Ala Tyr Phe Ser Ile Val Lys
        915                 920                 925

Ile Glu Arg Val Gly Lys His Gly Lys Val Phe Leu Thr Val Pro Ser
930                 935                 940

Leu Ser Ser Thr Ala Glu Glu Lys Phe Ile Lys Lys Gly Glu Phe Ser
945                 950                 955                 960

Gly Asp Asp Ser Leu Leu Asp Leu Asp Pro Glu Asp Thr Val Phe Tyr
                965                 970                 975

Val Gly Gly Val Pro Ser Asn Phe Lys Leu Pro Thr Ser Leu Asn Leu
            980                 985                 990

Pro Gly Phe Val Gly Cys Leu Glu Leu Ala Thr Leu Asn Asn Asp Val
        995                 1000                1005

Ile Ser Leu Tyr Asn Phe Lys His Ile Tyr Asn Met Asp Pro Ser Thr
    1010                1015                1020

Ser Val Pro Cys Ala Arg Asp Lys Leu Ala Phe Thr Gln Ser Arg Ala
1025                1030                1035                1040

Ala Ser Tyr Phe Phe Asp Gly Ser Gly Tyr Ala Val Val Arg Asp Ile
            1045                1050                1055

Thr Arg Arg Gly Lys Phe Gly Gln Val Thr Arg Phe Asp Ile Glu Val
            1060                1065                1070

-continued

Arg Thr Pro Ala Asp Asn Gly Leu Ile Leu Met Val Asn Gly Ser
        1075                1080                1085

Met Phe Phe Arg Leu Glu Met Arg Asn Gly Tyr Leu His Val Phe Tyr
    1090                1095                    1100

Asp Phe Gly Phe Ser Gly Gly Pro Val His Leu Glu Asp Thr Leu Lys
1105            1110                1115                    1120

Lys Ala Gln Ile Asn Asp Ala Lys Tyr His Glu Ile Ser Ile Ile Tyr
            1125                1130                1135

His Asn Asp Lys Lys Met Ile Leu Val Val Asp Arg Arg His Val Lys
        1140                1145                1150

Ser Met Asp Asn Glu Lys Met Lys Ile Pro Phe Thr Asp Ile Tyr Ile
        1155                1160                1165

Gly Gly Ala Pro Pro Glu Ile Leu Gln Ser Arg Ala Leu Arg Ala His
    1170                1175                1180

Leu Pro Leu Asp Ile Asn Phe Arg Gly Cys Met Lys Gly Phe Gln Phe
1185            1190                1195                1200

Gln Lys Lys Asp Phe Asn Leu Leu Glu Gln Thr Glu Thr Leu Gly Val
            1205                1210                1215

Gly Tyr Gly Cys Pro Glu Asp Ser Leu Ile Ser Arg Arg Ala Tyr Phe
        1220                1225                1230

Asn Gly Gln Ser Phe Ile Ala Ser Ile Gln Lys Ile Ser Phe Phe Asp
        1235                1240                1245

Gly Phe Glu Gly Gly Phe Asn Phe Arg Thr Leu Gln Pro Asn Gly Leu
    1250                1255                1260

Leu Phe Tyr Tyr Ala Ser Gly Ser Asp Val Phe Ser Ile Ser Leu Asp
1265            1270                1275                1280

Asn Gly Thr Val Ile Met Asp Val Lys Gly Ile Lys Val Gln Ser Val
            1285                1290                1295

Asp Lys Gln Tyr Asn Asp Gly Leu Ser His Phe Val Ile Ser Ser Val
        1300                1305                1310

Ser Pro Thr Arg Tyr Glu Leu Ile Val Asp Lys Ser Arg Val Gly Ser
        1315                1320                1325

Lys Asn Pro Thr Lys Gly Lys Ile Glu Gln Thr Gln Ala Ser Glu Lys
        1330                1335                1340

Lys Phe Tyr Phe Gly Gly Ser Pro Ile Ser Ala Gln Tyr Ala Asn Phe
1345            1350                1355                1360

Thr Gly Cys Ile Ser Asn Ala Tyr Phe Thr Arg Val Asp Arg Asp Val
            1365                1370                1375

Glu Val Glu Asp Phe Gln Arg Tyr Thr Glu Lys Val His Thr Ser Leu
            1380                1385                1390

Tyr Glu Cys Pro Ile Glu Ser Ser Pro Leu Phe Leu Leu His Lys Lys
        1395                1400                1405

Gly Lys Asn Leu Ser Lys Pro Lys Ala Ser Gln Asn Lys Lys Gly Gly
        1410                1415                1420

Lys Ser Lys Asp Ala Pro Ser Trp Asp Pro Val Ala Leu Lys Leu Pro
1425            1430                1435                1440

Glu Arg Asn Thr Pro Arg Asn Ser His Cys His Leu Ser Asn Ser Pro
            1445                1450                1455

Arg Ala Ile Glu His Ala Tyr Gln Tyr Gly Gly Thr Ala Asn Ser Arg
            1460                1465                1470

Gln Glu Phe Glu His Leu Lys Gly Asp Phe Gly Ala Lys Ser Gln Phe
        1475                1480                1485

Ser Ile Arg Leu Arg Thr Arg Ser Ser His Gly Met Ile Phe Tyr Val

| | | | | | | | | | | | |
|---|---|---|---|---|---|---|---|---|---|---|---|
| | | 1490 | | | 1495 | | | 1500 | | | |
| Ser | Asp | Gln | Glu | Glu | Asn | Asp | Phe | Met | Thr | Leu | Phe | Leu | Ala | His | Gly |
| 1505 | | | | 1510 | | | | 1515 | | | | 1520 |

Ser Asp Gln Glu Glu Asn Asp Phe Met Thr Leu Phe Leu Ala His Gly
1505                1510                1515                1520

Arg Leu Val Tyr Met Phe Asn Val Gly His Lys Lys Leu Lys Ile Arg
           1525                1530                1535

Ser Gln Glu Lys Tyr Asn Asp Gly Leu Trp His Asp Val Ile Phe Ile
           1540                1545                1550

Arg Glu Arg Ser Ser Gly Arg Leu Val Ile Asp Gly Leu Arg Val Leu
           1555                1560                1565

Glu Glu Ser Leu Pro Pro Thr Glu Ala Thr Trp Lys Ile Lys Gly Pro
1570                1575                1580

Ile Tyr Leu Gly Gly Val Ala Pro Gly Lys Ala Val Lys Asn Val Gln
1585                1590                1595                1600

Ile Asn Ser Ile Tyr Ser Phe Ser Gly Cys Leu Ser Asn Leu Gln Leu
           1605                1610                1615

Asn Gly Ala Ser Ile Thr Ser Ala Ser Gln Thr Phe Ser Val Thr Pro
           1620                1625                1630

Cys Phe Glu Gly Pro Met Glu Thr Gly Thr Tyr Phe Ser Thr Glu Gly
           1635                1640                1645

Gly Tyr Val Val Leu Asp Glu Ser Phe Asn Ile Gly Leu Lys Phe Glu
           1650                1655                1660

Ile Ala Phe Glu Val Arg Pro Arg Ser Ser Gly Thr Leu Val His
1665                1670                1675                1680

Gly His Ser Val Asn Gly Glu Tyr Leu Asn Val His Met Lys Asn Gly
           1685                1690                1695

Gln Val Ile Val Lys Val Asn Asn Gly Ile Arg Asp Phe Ser Thr Ser
           1700                1705                1710

Val Thr Pro Lys Gln Ser Leu Cys Asp Gly Arg Trp His Arg Ile Thr
           1715                1720                1725

Val Ile Arg Asp Ser Asn Val Val Gln Leu Asp Val Asp Ser Glu Val
           1730                1735                1740

Asn His Val Val Gly Pro Leu Asn Pro Lys Pro Ile Asp His Arg Glu
1745                1750                1755                1760

Pro Val Phe Val Gly Gly Val Pro Glu Ser Leu Leu Thr Pro Arg Leu
           1765                1770                1775

Ala Pro Ser Lys Pro Phe Thr Gly Cys Ile Arg His Phe Val Ile Asp
           1780                1785                1790

Gly His Pro Val Ser Phe Ser Lys Ala Ala Leu Val Ser Gly Ala Val
           1795                1800                1805

Ser Ile Asn Ser Cys Pro Ala Ala
1810                1815

<210> SEQ ID NO 29
<211> LENGTH: 334
<212> TYPE: DNA
<213> ORGANISM: Artificial Sequence
<220> FEATURE:
<223> OTHER INFORMATION: Synthetic

<400> SEQUENCE: 29
gacattgtgc tgacacagtc tcctgcttcc ttagctgtat ctctggggca gagggccacc    60
atctcatgca gggccagcaa aagtgtcagt acatctggct atagttatat gtactggtac   120
caacagaaac caggacagcc acccaaactc ctcatctatc ttgcatccaa cctagaatct   180
ggggtccctg ccaggttcag tggcagtggg tctgggacag acttcaccct caacatccat   240

```
cctgtggagg aggaggatgc tgcaacctat tactgtcaac acagtaggga gcttccattc    300
acgttcggct cggggacaaa gttggaaata aaac                                334
```

<210> SEQ ID NO 30
<211> LENGTH: 111
<212> TYPE: PRT
<213> ORGANISM: Artificial Sequence
<220> FEATURE:
<223> OTHER INFORMATION: Synthesized

<400> SEQUENCE: 30

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met Tyr Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Ser Gly Thr Lys Leu Glu Ile Lys
            100                 105                 110
```

<210> SEQ ID NO 31
<211> LENGTH: 15
<212> TYPE: PRT
<213> ORGANISM: Artificial Sequence
<220> FEATURE:
<223> OTHER INFORMATION: Synthetic

<400> SEQUENCE: 31

```
Arg Ala Ser Lys Ser Val Ser Thr Ser Gly Tyr Ser Tyr Met Tyr
1               5                   10                  15
```

<210> SEQ ID NO 32
<211> LENGTH: 6
<212> TYPE: PRT
<213> ORGANISM: Artificial Sequence
<220> FEATURE:
<223> OTHER INFORMATION: Synthetic

<400> SEQUENCE: 32

```
Ala Ser Asn Leu Glu Ser
1               5
```

<210> SEQ ID NO 33
<211> LENGTH: 9
<212> TYPE: PRT
<213> ORGANISM: Artificial Sequence
<220> FEATURE:
<223> OTHER INFORMATION: Synthetic

<400> SEQUENCE: 33

```
Gln His Ser Arg Glu Leu Pro Phe Thr
1               5
```

<210> SEQ ID NO 34
<211> LENGTH: 363
<212> TYPE: DNA

<213> ORGANISM: Artificial Sequence
<220> FEATURE:
<223> OTHER INFORMATION: Synthetic

<400> SEQUENCE: 34

```
cagattcagt tggtgcagtc tggacctgag ctgaagaagc ctggagagac agtcaagatc    60
tcctgcaagg cttctgggta taccttcaca aactatggaa tgaactgggt gaagcaggct   120
ccaggaaagg gtttaaagtg gatgggctgg ataaacacct acactggaga gccaacatat   180
gctgatgact tcaagggacg gtttgccttg tctttggaaa cctctgccag cactgcctat   240
ttgcagatca acaacctcaa aaatgaggac atggctacat atttctgtgc aagatatagg   300
tataataaat acgagagggc tatggactac tggggtcaag aacctcagt caccgtctcc   360
tca                                                                363
```

<210> SEQ ID NO 35
<211> LENGTH: 121
<212> TYPE: PRT
<213> ORGANISM: Artificial Sequence
<220> FEATURE:
<223> OTHER INFORMATION: Synthesized

<400> SEQUENCE: 35

```
Gln Ile Gln Leu Val Gln Ser Gly Pro Glu Leu Lys Lys Pro Gly Glu
1               5                   10                  15
Thr Val Lys Ile Ser Cys Lys Ala Ser Gly Tyr Thr Phe Thr Asn Tyr
            20                  25                  30
Gly Met Asn Trp Val Lys Gln Ala Pro Gly Lys Gly Leu Lys Trp Met
        35                  40                  45
Gly Trp Ile Asn Thr Tyr Thr Gly Glu Pro Thr Tyr Ala Asp Asp Phe
    50                  55                  60
Lys Gly Arg Phe Ala Leu Ser Leu Glu Thr Ser Ala Ser Thr Ala Tyr
65                  70                  75                  80
Leu Gln Ile Asn Asn Leu Lys Asn Glu Asp Met Ala Thr Tyr Phe Cys
                85                  90                  95
Ala Arg Tyr Arg Tyr Asn Lys Tyr Glu Arg Ala Met Asp Tyr Trp Gly
            100                 105                 110
Gln Gly Thr Ser Val Thr Val Ser Ser
        115                 120
```

<210> SEQ ID NO 36
<211> LENGTH: 10
<212> TYPE: PRT
<213> ORGANISM: Artificial Sequence
<220> FEATURE:
<223> OTHER INFORMATION: Synthetic

<400> SEQUENCE: 36

```
Gly Tyr Thr Phe Thr Asn Tyr Gly Met Asn
1               5                   10
```

<210> SEQ ID NO 37
<211> LENGTH: 17
<212> TYPE: PRT
<213> ORGANISM: Artificial Sequence
<220> FEATURE:
<223> OTHER INFORMATION: Synthetic

<400> SEQUENCE: 37

```
Trp Ile Asn Thr Tyr Thr Gly Glu Pro Thr Tyr Ala Asp Asp Phe Lys
1               5                   10                  15
```

Gly

<210> SEQ ID NO 38
<211> LENGTH: 12
<212> TYPE: PRT
<213> ORGANISM: Artificial Sequence
<220> FEATURE:
<223> OTHER INFORMATION: Synthetic

<400> SEQUENCE: 38

Tyr Arg Tyr Asn Lys Tyr Glu Arg Ala Met Asp Tyr
1               5                   10

<210> SEQ ID NO 39
<211> LENGTH: 338
<212> TYPE: DNA
<213> ORGANISM: Artificial Sequence
<220> FEATURE:
<223> OTHER INFORMATION: Synthetic

<400> SEQUENCE: 39
gacattgtga tgtcacagtc tccatcctcc ctggctgtgt cagcaggaga gaaggtcact      60
atgagctgca atccagtca gagtctgctc aacagtagca cccgaaagaa cttcttggct     120
tggtaccagc agaaaccagg gcagtctcct aaactgctga tctactgggc atccactagg     180
gaatctgggg tccctgatcg cttcacaggc agtggatctg ggacagattt cactctcacc     240
atcagcagtg tgcaggctga agacctggca gtttattact gcaagcaatc ttataatcgg     300
tacacgttcg gaggggggac caagctggaa ataaaacg                             338

<210> SEQ ID NO 40
<211> LENGTH: 112
<212> TYPE: PRT
<213> ORGANISM: Artificial Sequence
<220> FEATURE:
<223> OTHER INFORMATION: Synthesized

<400> SEQUENCE: 40

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
                20                  25                  30

Ser Thr Arg Lys Asn Phe Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Arg Tyr Thr Phe Gly Gly Gly Thr Lys Leu Glu Ile Lys
            100                 105                 110

<210> SEQ ID NO 41
<211> LENGTH: 17
<212> TYPE: PRT
<213> ORGANISM: Artificial Sequence
<220> FEATURE:
<223> OTHER INFORMATION: Synthetic

<400> SEQUENCE: 41

```
Lys Ser Ser Gln Ser Leu Leu Asn Ser Ser Thr Arg Lys Asn Phe Leu
1               5                   10                  15

Ala
```

<210> SEQ ID NO 42
<211> LENGTH: 7
<212> TYPE: PRT
<213> ORGANISM: Artificial Sequence
<220> FEATURE:
<223> OTHER INFORMATION: Synthetic

<400> SEQUENCE: 42

```
Trp Ala Ser Thr Arg Glu Ser
1               5
```

<210> SEQ ID NO 43
<211> LENGTH: 8
<212> TYPE: PRT
<213> ORGANISM: Artificial Sequence
<220> FEATURE:
<223> OTHER INFORMATION: Synthetic

<400> SEQUENCE: 43

```
Lys Gln Ser Tyr Asn Arg Tyr Thr
1               5
```

<210> SEQ ID NO 44
<211> LENGTH: 351
<212> TYPE: DNA
<213> ORGANISM: Artificial Sequence
<220> FEATURE:
<223> OTHER INFORMATION: Synthetic

<400> SEQUENCE: 44

```
gagatccagc tgcagcagac tggacctgag ctggtgaagc ctggggcttc agtgaagata     60
tcctgcaagg cttctggtta ttcattcact gactacatca tgctctgggt gaagcagagc    120
catggaaaga gccttgagtg gattggaaat attaatcctt actctggtag tagtggctac    180
aatctgaagt tcaagggcaa ggccacattg actgtagaca atcttccag cacagcctac     240
atgcagctca cagtctgac atctgaggac tctgcagtct attactgtgc aagagggaag    300
gactttgcta tggactactg gggtcaagga acctcagtca ccgtctcctc a              351
```

<210> SEQ ID NO 45
<211> LENGTH: 117
<212> TYPE: PRT
<213> ORGANISM: Artificial Sequence
<220> FEATURE:
<223> OTHER INFORMATION: Synthesized

<400> SEQUENCE: 45

```
Glu Ile Gln Leu Gln Gln Thr Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Ile Met Leu Trp Val Lys Gln Ser His Gly Lys Ser Leu Glu Trp Ile
        35                  40                  45

Gly Asn Ile Asn Pro Tyr Ser Gly Ser Ser Gly Tyr Asn Leu Lys Phe
    50                  55                  60

Lys Gly Lys Ala Thr Leu Thr Val Asp Lys Ser Ser Thr Ala Tyr
65                  70                  75                  80

Met Gln Leu Asn Ser Leu Thr Ser Glu Asp Ser Ala Val Tyr Tyr Cys
```

```
                85                  90                  95
Ala Arg Gly Lys Asp Phe Ala Met Asp Tyr Trp Gly Gln Gly Thr Ser
            100                 105                 110

Val Thr Val Ser Ser
        115

<210> SEQ ID NO 46
<211> LENGTH: 10
<212> TYPE: PRT
<213> ORGANISM: Artificial Sequence
<220> FEATURE:
<223> OTHER INFORMATION: Synthetic

<400> SEQUENCE: 46

Gly Tyr Ser Phe Thr Asp Tyr Ile Met Leu
1               5                   10

<210> SEQ ID NO 47
<211> LENGTH: 17
<212> TYPE: PRT
<213> ORGANISM: Artificial Sequence
<220> FEATURE:
<223> OTHER INFORMATION: Synthetic

<400> SEQUENCE: 47

Asn Ile Asn Pro Tyr Ser Gly Ser Ser Gly Tyr Asn Leu Lys Phe Lys
1               5                   10                  15

Gly

<210> SEQ ID NO 48
<211> LENGTH: 7
<212> TYPE: PRT
<213> ORGANISM: Artificial Sequence
<220> FEATURE:
<223> OTHER INFORMATION: Synthetic

<400> SEQUENCE: 48

Gly Lys Asp Phe Ala Met Asp
1               5

<210> SEQ ID NO 49
<211> LENGTH: 322
<212> TYPE: DNA
<213> ORGANISM: Artificial Sequence
<220> FEATURE:
<223> OTHER INFORMATION: Synthetic

<400> SEQUENCE: 49
gacattgtga tgactcagtc tccagccacc ctgtctgtga ctccaggaga tagagtctct    60
ctttcatgca gggccagcca gagtattagc gactacttac actggtatca acaaaaatca   120
catgagtctc caaggcttct catcaaatat gcttcccaat ccatctctgg atcccctcc   180 aggttcagtg gcagtggatc agggtcagat ttcactctca gtatcaacag tgtggaacct   240
gaagatgttg gagtgtatta ctgtcaaaat ggtcacaact ttcctcggac gttcggtgga   300
ggcaccaagc tggaaatcaa ac                                           322

<210> SEQ ID NO 50
<211> LENGTH: 107
<212> TYPE: PRT
<213> ORGANISM: Artificial Sequence
<220> FEATURE:
<223> OTHER INFORMATION: Synthesized
```

<400> SEQUENCE: 50

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Asn Phe Pro Arg
                85                  90                  95

Thr Phe Gly Gly Gly Thr Lys Leu Glu Ile Lys
            100                 105

<210> SEQ ID NO 51
<211> LENGTH: 11
<212> TYPE: PRT
<213> ORGANISM: Artificial Sequence
<220> FEATURE:
<223> OTHER INFORMATION: Synthetic

<400> SEQUENCE: 51

Arg Ala Ser Gln Ser Ile Ser Asp Tyr Leu His
1               5                   10

<210> SEQ ID NO 52
<211> LENGTH: 7
<212> TYPE: PRT
<213> ORGANISM: Artificial Sequence
<220> FEATURE:
<223> OTHER INFORMATION: Synthetic

<400> SEQUENCE: 52

Tyr Ala Ser Gln Ser Ile Ser
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic

<400> SEQUENCE: 53

Gln Asn Gly His Asn Phe Pro Arg Thr
1               5

<210> SEQ ID NO 54
<211> LENGTH: 366
<212> TYPE: DNA
<213> ORGANISM: Artificial Sequence
<220> FEATURE:
<223> OTHER INFORMATION: Synthetic

<400> SEQUENCE: 54
caggtccaac tgcagcagcc tggggctgag cttgtgcagc ctggggctcc agtgaagctg      60
tcctgcaagg cttctggcta catttttcacc agctactgga tgaactgggt gaagcagagg    120
cctggacgag gcctcgagtg gattggaagg attgatcctt ccgatagtaa aattcactac    180
aatcaaaagt tcaaagacaa ggccacactg actgtagaca gatcctccag cacagcctac    240

```
atccaactcg gcagcctgac atctgaggac tctgcggtct attattgtgc aaaagagggg      300
ggtttacgac gggggactac tgctatggac tactggggtc aaggaacctc agtcaccgtc      360
tcctca                                                                  366
```

<210> SEQ ID NO 55
<211> LENGTH: 122
<212> TYPE: PRT
<213> ORGANISM: Artificial Sequence
<220> FEATURE:
<223> OTHER INFORMATION: Synthesized

<400> SEQUENCE: 55

```
Gln Val Gln Leu Gln Gln Pro Gly Ala Glu Leu Val Gln Pro Gly Ala
1               5                   10                  15

Pro Val Lys Leu Ser Cys Lys Ala Ser Gly Tyr Ile Phe Thr Ser Tyr
            20                  25                  30

Trp Met Asn Trp Val Lys Gln Arg Pro Gly Arg Gly Leu Glu Trp Ile
        35                  40                  45

Gly Arg Ile Asp Pro Ser Asp Ser Lys Ile His Tyr Asn Gln Lys Phe
    50                  55                  60

Lys Asp Lys Ala Thr Leu Thr Val Asp Arg Ser Ser Thr Ala Tyr
65                  70                  75                  80

Ile Gln Leu Gly Ser Leu Thr Ser Glu Asp Ser Ala Val Tyr Tyr Cys
                85                  90                  95

Ala Lys Glu Gly Gly Leu Arg Arg Gly Asp Tyr Ala Met Asp Tyr Trp
            100                 105                 110

Gly Gln Gly Thr Ser Val Thr Val Ser Ser
        115                 120
```

<210> SEQ ID NO 56
<211> LENGTH: 10
<212> TYPE: PRT
<213> ORGANISM: Artificial Sequence
<220> FEATURE:
<223> OTHER INFORMATION: Synthetic

<400> SEQUENCE: 56

```
Gly Tyr Ile Phe Thr Ser Tyr Trp Met Asn
1               5                   10
```

<210> SEQ ID NO 57
<211> LENGTH: 17
<212> TYPE: PRT
<213> ORGANISM: Artificial Sequence
<220> FEATURE:
<223> OTHER INFORMATION: Synthetic

<400> SEQUENCE: 57

```
Arg Ile Asp Pro Ser Asp Ser Lys Ile His Tyr Asn Gln Lys Phe Lys
1               5                   10                  15

Asp
```

<210> SEQ ID NO 58
<211> LENGTH: 13
<212> TYPE: PRT
<213> ORGANISM: Artificial Sequence
<220> FEATURE:
<223> OTHER INFORMATION: Synthetic

<400> SEQUENCE: 58

```
Glu Gly Gly Leu Arg Arg Gly Asp Tyr Ala Met Asp Tyr
1               5                   10
```

<210> SEQ ID NO 59
<211> LENGTH: 337
<212> TYPE: DNA
<213> ORGANISM: Artificial Sequence
<220> FEATURE:
<223> OTHER INFORMATION: Synthetic

<400> SEQUENCE: 59

```
gacattgtga tgtcacagtc tccatcctcc ctggctgtgt cagcaggaga gaaggtcact    60
atgaactgca atccagtcg gagtctgctc aacagtagaa tccgaaagaa ctacttggct   120
tggtaccagc agaaaccagg gcagtctcct aaactgctga tctactgggc atccactagg   180
gaatctgggg tccctgatcg cttcacaggc agtggatctg ggacagattt cactctcacc   240
atcagcagtg tgcaggctga agacctggca gtttattact gcaagcaatc ttataatctg   300
ctcacgttcg gtgctgggac caagctggag ctgaaac                            337
```

<210> SEQ ID NO 60
<211> LENGTH: 112
<212> TYPE: PRT
<213> ORGANISM: Artificial Sequence
<220> FEATURE:
<223> OTHER INFORMATION: Synthesized

<400> SEQUENCE: 60

```
Asp Ile Val Met Ser Gln Ser Pro Ser Ser Leu Ala Val Ser Ala Gly
1               5                   10                  15

Glu Lys Val Thr Met Asn Cys Lys Ser Ser Arg Ser Leu Leu Asn Ser
            20                  25                  30

Arg Ile Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Leu Thr Phe Gly Ala Gly Thr Lys Leu Glu Leu Lys
            100                 105                 110
```

<210> SEQ ID NO 61
<211> LENGTH: 17
<212> TYPE: PRT
<213> ORGANISM: Artificial Sequence
<220> FEATURE:
<223> OTHER INFORMATION: Synthetic

<400> SEQUENCE: 61

```
Lys Ser Ser Arg Ser Leu Leu Asn Ser Arg Ile Arg Lys Asn Tyr Leu
1               5                   10                  15

Ala
```

<210> SEQ ID NO 62
<211> LENGTH: 7
<212> TYPE: PRT
<213> ORGANISM: Artificial Sequence
<220> FEATURE:
<223> OTHER INFORMATION: Synthetic

<400> SEQUENCE: 62

Trp Ala Ser Thr Arg Glu Ser
1               5

<210> SEQ ID NO 63
<211> LENGTH: 8
<212> TYPE: PRT
<213> ORGANISM: Artificial Sequence
<220> FEATURE:
<223> OTHER INFORMATION: Synthetic

<400> SEQUENCE: 63

Lys Gln Ser Tyr Asn Leu Leu Thr
1               5

<210> SEQ ID NO 64
<211> LENGTH: 360
<212> TYPE: DNA
<213> ORGANISM: Artificial Sequence
<220> FEATURE:
<223> OTHER INFORMATION: Synthetic

<400> SEQUENCE: 64

```
gacgtgaagc tggtggagtc tgggggagac ttagtgaagc ctggagggtc cctgaaactc      60
tcctgtgcag cctctggatt cactttcagt agctatatca tgtcttgggt tcgtcagact     120
ccggagaaga ggctggagtg ggtcgcaacc attagtagtg gtggtagttc cacctactat     180
ccagacagtg tgaagggccg attcaccatc tccagagaca atgccaagaa caccctgtac     240
ctgcaaatga gcagtctgaa gtctgaggac acagccatgt attactgtac aagagatgat     300
gattacgacg taaaggtatt tgcttactgg ggccaaggga ctctggtcac tgtctctgca     360
```

<210> SEQ ID NO 65
<211> LENGTH: 120
<212> TYPE: PRT
<213> ORGANISM: Artificial Sequence
<220> FEATURE:
<223> OTHER INFORMATION: Synthesized

<400> SEQUENCE: 65

Asp Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Ile Met Ser Trp Val Arg Gln Thr Pro Glu Lys Arg Leu Glu Trp Val
        35                  40                  45

Ala Thr Ile Ser Ser Gly Gly Ser Ser Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Thr Arg Asp Asp Asp Tyr Asp Val Lys Val Phe Ala Tyr Trp Gly Gln
            100                 105                 110

Gly Thr Leu Val Thr Val Ser Ala
        115                 120

<210> SEQ ID NO 66
<211> LENGTH: 5
<212> TYPE: PRT
<213> ORGANISM: Artificial Sequence

```
<220> FEATURE:
<223> OTHER INFORMATION: Synthetic

<400> SEQUENCE: 66

Ser Tyr Ile Met Ser
1               5

<210> SEQ ID NO 67
<211> LENGTH: 17
<212> TYPE: PRT
<213> ORGANISM: Artificial Sequence
<220> FEATURE:
<223> OTHER INFORMATION: Synthetic

<400> SEQUENCE: 67

Thr Ile Ser Ser Gly Gly Ser Ser Thr Tyr Tyr Pro Asp Ser Val Lys
1               5                   10                  15

Gly

<210> SEQ ID NO 68
<211> LENGTH: 11
<212> TYPE: PRT
<213> ORGANISM: Artificial Sequence
<220> FEATURE:
<223> OTHER INFORMATION: Synthetic

<400> SEQUENCE: 68

Asp Asp Asp Tyr Asp Val Lys Val Phe Ala Tyr
1               5                   10

<210> SEQ ID NO 69
<211> LENGTH: 319
<212> TYPE: DNA
<213> ORGANISM: Artificial Sequence
<220> FEATURE:
<223> OTHER INFORMATION: Synthetic

<400> SEQUENCE: 69
gatatccgga tgactcagtc tccttcactc ctgtctgcat ctgtggggga cagagtcact      60
ctcaactgca aagcaagtca gaatatttat aacagcttag cctggtatca gcaaaagctt     120
ggagaaggtc ccaaagtcct gattttttaat gcaaacagtt tgcaaacggg catcccatca    180
aggttcagtg gcagtggatc tggtacagat ttcacactca ccatcagcag cctgcagcct    240
gaagattttg ccacatattt ctgccagcag ttttatagcg ggtacacgtt tggagctggg    300
accaagctgg aactgaaac                                                  319

<210> SEQ ID NO 70
<211> LENGTH: 106
<212> TYPE: PRT
<213> ORGANISM: Artificial Sequence
<220> FEATURE:
<223> OTHER INFORMATION: Synthesized

<400> SEQUENCE: 70

Asp Ile Arg Met Thr Gln Ser Pro Ser Leu Leu Ser Ala Ser Val Gly
1               5                   10                  15

Asp Arg Val Thr Leu Asn Cys Lys Ala Ser Gln Asn Ile Tyr Asn Ser
                20                  25                  30

Leu Ala Trp Tyr Gln Gln Lys Leu Gly Glu Gly Pro Lys Val Leu Ile
            35                  40                  45

Phe Asn Ala Asn Ser Leu Gln Thr Gly Ile Pro Ser Arg Phe Ser Gly
        50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Phe Tyr Ser Gly Tyr Thr
                 85                  90                  95

Phe Gly Ala Gly Thr Lys Leu Glu Leu Lys
            100                 105
```

<210> SEQ ID NO 71
<211> LENGTH: 106
<212> TYPE: PRT
<213> ORGANISM: Artificial Sequence
<220> FEATURE:
<223> OTHER INFORMATION: Synthetic

<400> SEQUENCE: 71

```
Asp Ile Gln Val Thr Gln Ser Pro Ser Leu Ser Ala Ser Val Gly
  1               5                  10                  15

Asp Arg Val Thr Leu Asn Cys Lys Ala Ser Gln Asn Ile Tyr Asn Ser
             20                  25                  30

Leu Ala Trp Tyr Gln Gln Lys Leu Gly Glu Gly Pro Lys Val Leu Ile
         35                  40                  45

Phe Asn Ala Asn Ser Leu Gln Thr Gly Ile Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Phe Tyr Ser Gly Tyr Thr
                 85                  90                  95

Phe Gly Ala Gly Thr Lys Leu Glu Leu Lys
            100                 105
```

<210> SEQ ID NO 72
<211> LENGTH: 106
<212> TYPE: PRT
<213> ORGANISM: Artificial Sequence
<220> FEATURE:
<223> OTHER INFORMATION: Synthetic

<400> SEQUENCE: 72

```
Asp Ile Val Leu Thr Gln Ser Pro Ser Leu Ser Ala Ser Val Gly
  1               5                  10                  15

Asp Arg Val Thr Leu Asn Cys Lys Ala Ser Gln Asn Ile Tyr Asn Ser
             20                  25                  30

Leu Ala Trp Tyr Gln Gln Lys Leu Gly Glu Gly Pro Lys Val Leu Ile
         35                  40                  45

Phe Asn Ala Asn Ser Leu Gln Thr Gly Ile Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Phe Tyr Ser Gly Tyr Thr
                 85                  90                  95

Phe Gly Ala Gly Thr Lys Leu Glu Leu Lys
            100                 105
```

<210> SEQ ID NO 73
<211> LENGTH: 11
<212> TYPE: PRT
<213> ORGANISM: Artificial Sequence
<220> FEATURE:
<223> OTHER INFORMATION: Synthetic

<400> SEQUENCE: 73

Lys Ala Ser Gln Asn Ile Tyr Asn Ser Leu Ala
1               5                   10

<210> SEQ ID NO 74
<211> LENGTH: 7
<212> TYPE: PRT
<213> ORGANISM: Artificial Sequence
<220> FEATURE:
<223> OTHER INFORMATION: Synthetic

<400> SEQUENCE: 74

Asn Ala Asn Ser Leu Gln Thr
1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic

<400> SEQUENCE: 75

Gln Gln Phe Tyr Ser Gly Tyr Thr
1               5

<210> SEQ ID NO 76
<211> LENGTH: 354
<212> TYPE: DNA
<213> ORGANISM: Artificial Sequence
<220> FEATURE:
<223> OTHER INFORMATION: Synthetic

<400> SEQUENCE: 76
caggtgcagc tgaaggagtc aggacctggt ctggtgcagc cctcacagac cctgtctctc    60
acctgcactg tctctggatt ctcattaacc agcaatggtg taagctgggt tcgccagcct   120
ccaggaaagg gtctggagtg gattgcagca atatcatctg gtggaaccac atattataat   180
tcagcgttca atcccgact gagcatcagc aggaacacct ccaagagcca agttctctta    240
aaaatgaaca gtctgcaaac tgaagacaca gccatgtact tctgtgccag acggtatggg   300
tacgggtggt actttgactt ctggggccca ggaaccatgg tcacagtctc ctca         354

<210> SEQ ID NO 77
<211> LENGTH: 118
<212> TYPE: PRT
<213> ORGANISM: Artificial Sequence
<220> FEATURE:
<223> OTHER INFORMATION: Synthesized

<400> SEQUENCE: 77

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Asn
                20                  25                  30

Gly Val Ser Trp Val Arg Gln Pro Pro Gly Lys Gly Leu Glu Trp Ile
            35                  40                  45

Ala Ala Ile Ser Ser Gly Gly Thr Thr Tyr Tyr Asn Ser Ala Phe Lys
        50                  55                  60

Ser Arg Leu Ser Ile Ser Arg Asn Thr Ser Lys Ser Gln Val Leu Leu
65                  70                  75                  80

Lys Met Asn Ser Leu Gln Thr Glu Asp Thr Ala Met Tyr Phe Cys Ala
            85                  90                  95

Arg Arg Tyr Gly Tyr Gly Trp Tyr Phe Asp Phe Trp Gly Pro Gly Thr
        100                 105                 110

Met Val Thr Val Ser Ser
        115

<210> SEQ ID NO 78
<211> LENGTH: 10
<212> TYPE: PRT
<213> ORGANISM: Artificial Sequence
<220> FEATURE:
<223> OTHER INFORMATION: Synthetic

<400> SEQUENCE: 78

Gly Phe Ser Leu Thr Ser Asn Gly Val Ser
1               5                   10

<210> SEQ ID NO 79
<211> LENGTH: 16
<212> TYPE: PRT
<213> ORGANISM: Artificial Sequence
<220> FEATURE:
<223> OTHER INFORMATION: Synthetic

<400> SEQUENCE: 79

Ala Ile Ser Ser Gly Gly Thr Thr Tyr Tyr Asn Ser Ala Phe Lys Ser
1               5                   10                  15

<210> SEQ ID NO 80
<211> LENGTH: 10
<212> TYPE: PRT
<213> ORGANISM: Artificial Sequence
<220> FEATURE:
<223> OTHER INFORMATION: Synthetic

<400> SEQUENCE: 80

Arg Tyr Gly Tyr Gly Trp Tyr Phe Asp Phe
1               5                   10

<210> SEQ ID NO 81
<211> LENGTH: 318
<212> TYPE: DNA
<213> ORGANISM: Artificial Sequence
<220> FEATURE:
<223> OTHER INFORMATION: Synthetic

<400> SEQUENCE: 81
gacatccggg tgactcagtc tccttcactc ctgtctgcat ctgtgggaga cagagtcact      60
ctcaactgca aaggaagtca gaatatttat aagagcttag cctggtttcg gctaaagcgt     120
ggagaagctc ccaagctcct gatttatgat gcaaacagtt tgcaaacggg catcccatca     180
aggttcagtg gcagtggatc tggtacagat ttcacactca ccatcaccag cctacagcct     240
gaagatgttg ccacatattt ctgccagcag tattatagcg gttacacgtt tggagctggg     300
accaagctgg aactgaaa                                                    318

<210> SEQ ID NO 82
<211> LENGTH: 106
<212> TYPE: PRT
<213> ORGANISM: Artificial Sequence
<220> FEATURE:
<223> OTHER INFORMATION: Synthesized

<400> SEQUENCE: 82

```
Asp Ile Arg Val Thr Gln Ser Pro Ser Leu Leu Ser Ala Ser Val Gly
1               5                   10                  15

Asp Arg Val Thr Leu Asn Cys Lys Gly Ser Gln Asn Ile Tyr Lys Ser
                20                  25                  30

Leu Ala Trp Phe Arg Leu Lys Arg Gly Glu Ala Pro Lys Leu Leu Ile
            35                  40                  45

Tyr Asp Ala Asn Ser Leu Gln Thr Gly Ile Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Val Ala Thr Tyr Phe Cys Gln Gln Tyr Tyr Ser Gly Tyr Thr
                85                  90                  95

Phe Gly Ala Gly Thr Lys Leu Glu Leu Lys
                100                 105
```

<210> SEQ ID NO 83
<211> LENGTH: 318
<212> TYPE: DNA
<213> ORGANISM: Artificial Sequence
<220> FEATURE:
<223> OTHER INFORMATION: Synthetic

<400> SEQUENCE: 83

```
gacatccagg tgactcagtc tccttcactc ctgtctgcat ctgtgggaga cagagtcact    60
ctcaactgca aggaagtca gaatatttat aagagcttag cctggtttcg ctaaagcgt    120
ggagaagctc ccaagctcct gatttatgat gcaaacagtt tgcaaacggg catcccatca   180
aggttcagtg gcagtggatc tggtacagat ttcacactca ccatcaccag cctacagcct   240
gaagatgttg ccacatattt ctgccagcag tattatagcg gttacacgtt tggagctggg   300
accaagctgg aactgaaa                                                  318
```

<210> SEQ ID NO 84
<211> LENGTH: 106
<212> TYPE: PRT
<213> ORGANISM: Artificial Sequence
<220> FEATURE:
<223> OTHER INFORMATION: Synthesized

<400> SEQUENCE: 84

```
Asp Ile Gln Val Thr Gln Ser Pro Ser Leu Leu Ser Ala Ser Val Gly
1               5                   10                  15

Asp Arg Val Thr Leu Asn Cys Lys Gly Ser Gln Asn Ile Tyr Lys Ser
                20                  25                  30

Leu Ala Trp Phe Arg Leu Lys Arg Gly Glu Ala Pro Lys Leu Leu Ile
            35                  40                  45

Tyr Asp Ala Asn Ser Leu Gln Thr Gly Ile Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Val Ala Thr Tyr Phe Cys Gln Gln Tyr Tyr Ser Gly Tyr Thr
                85                  90                  95

Phe Gly Ala Gly Thr Lys Leu Glu Leu Lys
                100                 105
```

<210> SEQ ID NO 85
<211> LENGTH: 11
<212> TYPE: PRT

<210> SEQ ID NO 85
<211> LENGTH: 11 (implied)
<212> TYPE: PRT
<213> ORGANISM: Artificial Sequence
<220> FEATURE:
<223> OTHER INFORMATION: Synthetic

<400> SEQUENCE: 85

Lys Gly Ser Gln Asn Ile Tyr Lys Ser Leu Ala
1               5                   10

<210> SEQ ID NO 86
<211> LENGTH: 7
<212> TYPE: PRT
<213> ORGANISM: Artificial Sequence
<220> FEATURE:
<223> OTHER INFORMATION: Synthetic

<400> SEQUENCE: 86

Asp Ala Asn Ser Leu Gln Thr
1               5

<210> SEQ ID NO 87
<211> LENGTH: 8
<212> TYPE: PRT
<213> ORGANISM: Artificial Sequence
<220> FEATURE:
<223> OTHER INFORMATION: Synthetic

<400> SEQUENCE: 87

Gln Gln Tyr Tyr Ser Gly Tyr Thr
1               5

<210> SEQ ID NO 88
<211> LENGTH: 348
<212> TYPE: DNA
<213> ORGANISM: Artificial Sequence
<220> FEATURE:
<223> OTHER INFORMATION: Synthetic

<400> SEQUENCE: 88
caggtgcagc tgaaggagtc aggacctggt ctggtgcagt cctcacagac cctgtctctc      60
acctgcactg tctctggatt ctcattaacc agtaatggtg taagctgggt tcgccagcct     120
ccaggaaagg gtctggagtg gattgcagca atatcaagtg gtggaagcac atattataat     180
tcagcgttca atcccgact gagcatcagc aggaacacct ccaagagcca agttctctta      240
aaaatgaaca gtctgcaaac tgaagacaca ggcatgtact tctgtgccag acatagaccg     300
ttctactttg attactgggg ccaaggagtc atggtcacag tctcctca                  348

<210> SEQ ID NO 89
<211> LENGTH: 116
<212> TYPE: PRT
<213> ORGANISM: Artificial Sequence
<220> FEATURE:
<223> OTHER INFORMATION: Synthesized

<400> SEQUENCE: 89

Gln Val Gln Leu Lys Glu Ser Gly Pro Gly Leu Val Gln Ser Ser Gln
1               5                   10                  15

Thr Leu Ser Leu Thr Cys Thr Val Ser Gly Phe Ser Leu Thr Ser Asn
            20                  25                  30

Gly Val Ser Trp Val Arg Gln Pro Pro Gly Lys Gly Leu Glu Trp Ile
        35                  40                  45

Ala Ala Ile Ser Ser Gly Gly Ser Thr Tyr Tyr Asn Ser Ala Phe Lys
    50                  55                  60

```
Ser Arg Leu Ser Ile Ser Arg Asn Thr Ser Lys Ser Gln Val Leu Leu
 65                  70                  75                  80

Lys Met Asn Ser Leu Gln Thr Glu Asp Thr Gly Met Tyr Phe Cys Ala
                 85                  90                  95

Arg His Arg Pro Phe Tyr Phe Asp Tyr Trp Gly Gln Gly Val Met Val
            100                 105                 110

Thr Val Ser Ser
            115

<210> SEQ ID NO 90
<211> LENGTH: 10
<212> TYPE: PRT
<213> ORGANISM: Artificial Sequence
<220> FEATURE:
<223> OTHER INFORMATION: Synthetic

<400> SEQUENCE: 90

Gly Phe Ser Leu Thr Ser Asn Gly Val Ser
 1               5                  10

<210> SEQ ID NO 91
<211> LENGTH: 16
<212> TYPE: PRT
<213> ORGANISM: Artificial Sequence
<220> FEATURE:
<223> OTHER INFORMATION: Synthetic

<400> SEQUENCE: 91

Ala Ile Ser Ser Gly Gly Ser Thr Tyr Tyr Asn Ser Ala Phe Lys Ser
 1               5                  10                  15

<210> SEQ ID NO 92
<211> LENGTH: 8
<212> TYPE: PRT
<213> ORGANISM: Artificial Sequence
<220> FEATURE:
<223> OTHER INFORMATION: Synthetic

<400> SEQUENCE: 92

His Arg Pro Phe Tyr Phe Asp Tyr
 1               5

<210> SEQ ID NO 93
<211> LENGTH: 120
<212> TYPE: PRT
<213> ORGANISM: Artificial Sequence
<220> FEATURE:
<223> OTHER INFORMATION: Synthetic

<400> SEQUENCE: 93

Asp Val Lys Leu Val Glu Ser Gly Gly Asp Leu Val Lys Pro Gly Gly
 1               5                  10                  15

Ser Leu Lys Leu Ser Cys Ala Ala Ser Gly Phe Thr Phe Ser Ser Tyr
                20                  25                  30

Ile Met Ser Trp Val Arg Gln Thr Pro Glu Lys Arg Leu Glu Trp Val
            35                  40                  45

Ala Thr Ile Ser Ser Gly Gly Ser Thr Tyr Tyr Pro Asp Ser Val
        50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                85                  90                  95
```

```
Thr Arg Asp Asp Asp Tyr Asp Val Lys Val Phe Ala Tyr Trp Gly Gln
            100                 105                 110

Gly Thr Leu Val Thr Val Ser Ala
        115                 120

<210> SEQ ID NO 94
<211> LENGTH: 120
<212> TYPE: PRT
<213> ORGANISM: Artificial Sequence
<220> FEATURE:
<223> OTHER INFORMATION: Synthetic

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Ser Trp Val Arg Gln Ala Pro Gly Lys Gly Leu Glu Trp Val
        35                  40                  45

Ala Thr Ile Ser Ser Gly Gly Ser Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Asp Asp Asp Tyr Asp Val Lys Val Phe Ala Tyr Trp Gly Gln
            100                 105                 110

Gly Thr Met Val Thr Val Ser Ser
        115                 120

<210> SEQ ID NO 95
<211> LENGTH: 120
<212> TYPE: PRT
<213> ORGANISM: Artificial Sequence
<220> FEATURE:
<223> OTHER INFORMATION: Synthetic

<400> SEQUENCE: 95

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Ser Trp Val Arg Gln Ala Pro Gly Lys Arg Leu Glu Trp Val
        35                  40                  45

Ala Thr Ile Ser Ser Gly Gly Ser Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Asp Asp Asp Tyr Asp Val Lys Val Phe Ala Tyr Trp Gly Gln
            100                 105                 110

Gly Thr Met Val Thr Val Ser Ser
        115                 120

<210> SEQ ID NO 96
<211> LENGTH: 120
<212> TYPE: PRT
<213> ORGANISM: Artificial Sequence
```

-continued

```
<220> FEATURE:
<223> OTHER INFORMATION: Synthetic

<400> SEQUENCE: 96
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ala Ile Phe Gly Val Val Ser His Ile Trp Gly Gln
            100                 105                 110

Gly Thr Met Val Thr Val Ser Ser
            115                 120

```
<210> SEQ ID NO 97
<211> LENGTH: 112
<212> TYPE: PRT
<213> ORGANISM: Artificial Sequence
<220> FEATURE:
<223> OTHER INFORMATION: Synthetic

<400> SEQUENCE: 97
```

Asp Ile Val Met Ser Gln Ser Pro Ser Ser Leu Ala Val Ser Ala Gly
1               5                   10                  15

Glu Lys Val Thr Met Asn Cys Lys Ser Ser Arg Ser Leu Leu Asn Ser
            20                  25                  30

Arg Ile Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Leu Thr Phe Gly Ala Gly Thr Lys Leu Glu Leu Lys
            100                 105                 110

```
<210> SEQ ID NO 98
<211> LENGTH: 112
<212> TYPE: PRT
<213> ORGANISM: Artificial Sequence
<220> FEATURE:
<223> OTHER INFORMATION: Synthetic

<400> SEQUENCE: 98
```

Asp Ile Val Met Thr Gln Ser Pro Asp Ser Leu Ala Val Ser Leu Gly
1               5                   10                  15

Glu Arg Ala Thr Ile Asn Cys Lys Ser Ser Arg Ser Leu Leu Asn Ser
            20                  25                  30

Arg Ile Arg Lys Asn Tyr Leu Ala Trp Tyr Gln Gln Lys Pro Gly Gln
        35                  40                  45

```
Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Leu Thr Phe Gly Gln Gly Thr Lys Val Glu Ile Lys
                100                 105                 110

<210> SEQ ID NO 99
<211> LENGTH: 112
<212> TYPE: PRT
<213> ORGANISM: Artificial Sequence
<220> FEATURE:
<223> OTHER INFORMATION: Synthetic

<400> SEQUENCE: 99

Asp Ile Val Met Thr Gln Ser Pro Asp Ser Leu Ala Val Ser Leu Gly
1               5                   10                  15

Glu Arg Ala Thr Ile Asn Cys Lys Ser Ser Arg Ser Leu Leu Asn Ser
                20                  25                  30

Arg Ile Arg Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Leu Thr Phe Gly Gln Gly Thr Lys Val Glu Ile Lys
                100                 105                 110

<210> SEQ ID NO 100
<211> LENGTH: 113
<212> TYPE: PRT
<213> ORGANISM: Artificial Sequence
<220> FEATURE:
<223> OTHER INFORMATION: Synthetic

<400> SEQUENCE: 100

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
                20                  25                  30

Ser Asp Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asn Leu Pro Trp Thr Phe Gly Gln Gly Thr Lys Val Glu Ile
                100                 105                 110

Lys

<210> SEQ ID NO 101
<211> LENGTH: 116
```

```
<212> TYPE: PRT
<213> ORGANISM: Artificial Sequence
<220> FEATURE:
<223> OTHER INFORMATION: Synthetic

<400> SEQUENCE: 101

Gln Val Gln Leu Lys Glu Ser Gly Pro Gly Leu Val Gln Ser Ser Gln
1               5                   10                  15

Thr Leu Ser Leu Thr Cys Thr Val Ser Gly Phe Ser Leu Thr Ser Asn
            20                  25                  30

Gly Val Ser Trp Val Arg Gln Pro Pro Gly Lys Gly Leu Glu Trp Ile
        35                  40                  45

Ala Ala Ile Ser Ser Gly Gly Ser Thr Tyr Tyr Asn Ser Ala Phe Lys
    50                  55                  60

Ser Arg Leu Ser Ile Ser Pro Asn Thr Ser Lys Ser Gln Val Leu Leu
65                  70                  75                  80

Lys Met Asn Ser Leu Gln Thr Glu Asp Thr Gly Met Tyr Phe Cys Ala
                85                  90                  95

Arg His Arg Pro Phe Tyr Phe Asp Tyr Trp Gly Gln Gly Val Met Val
            100                 105                 110

Thr Val Ser Ser
        115

<210> SEQ ID NO 102
<211> LENGTH: 116
<212> TYPE: PRT
<213> ORGANISM: Artificial Sequence
<220> FEATURE:
<223> OTHER INFORMATION: Synthetic

<400> SEQUENCE: 102

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Ser Asn
            20                  25                  30

Gly Val Ser Trp Val Arg Gln Pro Pro Gly Lys Ala Leu Glu Trp Ile
        35                  40                  45

Ala Ala Ile Ser Ser Gly Gly Ser Thr Tyr Tyr Asn Ser Ala Phe Lys
    50                  55                  60

Ser Arg Leu Thr Ile Ser Arg Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg His Arg Pro Phe Tyr Phe Asp Tyr Trp Gly Gln Gly Thr Leu Val
            100                 105                 110

Thr Val Ser Ser
        115

<210> SEQ ID NO 103
<211> LENGTH: 116
<212> TYPE: PRT
<213> ORGANISM: Artificial Sequence
<220> FEATURE:
<223> OTHER INFORMATION: Synthetic

<400> SEQUENCE: 103

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Ser Asn
```

-continued

```
                 20                  25                  30

Gly Val Ser Trp Val Arg Gln Pro Pro Gly Lys Ala Leu Glu Trp Ile
            35                  40                  45

Ala Ala Ile Ser Ser Gly Gly Ser Thr Tyr Tyr Asn Ser Ala Phe Lys
        50                  55                  60

Ser Arg Leu Ser Ile Ser Arg Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg His Arg Pro Phe Tyr Phe Asp Tyr Trp Gly Gln Gly Thr Leu Val
            100                 105                 110

Thr Val Ser Ser
        115

<210> SEQ ID NO 104
<211> LENGTH: 116
<212> TYPE: PRT
<213> ORGANISM: Artificial Sequence
<220> FEATURE:
<223> OTHER INFORMATION: Synthetic

<400> SEQUENCE: 104

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Ser Asn
                20                  25                  30

Gly Val Ser Trp Val Arg Gln Pro Pro Gly Lys Ala Leu Glu Trp Ile
            35                  40                  45

Ala Ala Ile Ser Ser Gly Gly Ser Thr Tyr Tyr Asn Ser Ala Phe Lys
        50                  55                  60

Ser Arg Leu Thr Ile Ser Arg Asn Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg His Arg Pro Phe Tyr Phe Asp Tyr Trp Gly Gln Gly Thr Leu Val
            100                 105                 110

Thr Val Ser Ser
        115

<210> SEQ ID NO 105
<211> LENGTH: 116
<212> TYPE: PRT
<213> ORGANISM: Artificial Sequence
<220> FEATURE:
<223> OTHER INFORMATION: Synthetic

<400> SEQUENCE: 105

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Ser Ser
                20                  25                  30

Gly Val Ser Trp Val Arg Gln Pro Pro Gly Lys Ala Leu Glu Trp Ile
            35                  40                  45

Ala Ala Ile Ser Ser Gly Gly Ser Thr Tyr Tyr Asn Ser Ala Phe Lys
        50                  55                  60

Ser Arg Leu Thr Ile Ser Pro Asp Thr Ser Lys Ser Gln Val Val Leu
65                  70                  75                  80
```

Thr Met Thr Asn Met Asp Pro Val Asp Thr Ala Thr Tyr Tyr Cys Ala
                85                  90                  95

Arg His Arg Pro Phe Tyr Phe Asp Tyr Trp Gly Gln Gly Thr Leu Val
            100                 105                 110

Thr Val Ser Ser
        115

<210> SEQ ID NO 106
<211> LENGTH: 116
<212> TYPE: PRT
<213> ORGANISM: Artificial Sequence
<220> FEATURE:
<223> OTHER INFORMATION: Synthetic

<400> SEQUENCE: 106

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Ser Gln
            20                  25                  30

Gly Val Ser Trp Val Arg Gln Pro Pro Gly Lys Ala Leu Glu Trp Ile
        35                  40                  45

Ala Ala Ile Ser Ser Gly Gly Ser Thr Tyr Tyr Asn Ser Ala Phe Lys
    50                  55                  60

Ser Arg Leu Thr Ile Ser Pro Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg His Arg Pro Phe Tyr Phe Asp Tyr Trp Gly Gln Gly Thr Leu Val
            100                 105                 110

Thr Val Ser Ser
        115

<210> SEQ ID NO 107
<211> LENGTH: 116
<212> TYPE: PRT
<213> ORGANISM: Artificial Sequence
<220> FEATURE:
<223> OTHER INFORMATION: Synthetic

<400> SEQUENCE: 107

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Ser Asn
            20                  25                  30

Ala Val Ser Trp Val Arg Gln Pro Pro Gly Lys Ala Leu Glu Trp Ile
        35                  40                  45

Ala Ala Ile Ser Ser Gly Gly Ser Thr Tyr Tyr Asn Ser Ala Phe Lys
    50                  55                  60

Ser Arg Leu Thr Ile Ser Arg Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg His Arg Pro Phe Tyr Phe Asp Tyr Trp Gly Gln Gly Thr Leu Val
            100                 105                 110

Thr Val Ser Ser
        115

<210> SEQ ID NO 108

<211> LENGTH: 131
<212> TYPE: PRT
<213> ORGANISM: Artificial Sequence
<220> FEATURE:
<223> OTHER INFORMATION: Synthetic

<400> SEQUENCE: 108

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ile Gly Glu Ser Ala Ser Asp Arg Tyr Cys Ser Gly Gly
            100                 105                 110

Ser Cys Phe Gly Trp Phe Asp Pro Trp Gly Gln Gly Thr Leu Val Thr
        115                 120                 125

Val Ser Ser
    130

<210> SEQ ID NO 109
<211> LENGTH: 106
<212> TYPE: PRT
<213> ORGANISM: Artificial Sequence
<220> FEATURE:
<223> OTHER INFORMATION: Synthetic

<400> SEQUENCE: 109

Asp Ile Gln Val Thr Gln Ser Pro Ser Leu Ser Ala Ser Val Gly
1               5                   10                  15

Asp Arg Val Thr Leu Asn Cys Lys Gly Ser Gln Asn Ile Tyr Lys Ser
            20                  25                  30

Leu Ala Trp Phe Arg Leu Lys Arg Gly Glu Ala Pro Lys Leu Leu Ile
        35                  40                  45

Tyr Asp Ala Asn Ser Leu Gln Thr Gly Ile Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Val Ala Thr Tyr Phe Cys Gln Gln Tyr Tyr Ser Gly Tyr Thr
                85                  90                  95

Phe Gly Ala Gly Thr Lys Leu Glu Leu Lys
            100                 105

<210> SEQ ID NO 110
<211> LENGTH: 106
<212> TYPE: PRT
<213> ORGANISM: Artificial Sequence
<220> FEATURE:
<223> OTHER INFORMATION: Synthetic

<400> SEQUENCE: 110

Asp Ile Gln Met Thr Gln Ser Pro Ser Ser Leu Ser Ala Ser Val Gly
1               5                   10                  15

```
Asp Arg Val Thr Ile Thr Cys Lys Gly Ser Gln Asn Ile Tyr Lys Ser
            20                  25                  30

Leu Ala Trp Phe Gln Gln Lys Pro Gly Lys Val Pro Lys Leu Leu Ile
        35                  40                  45

Tyr Asp Ala Asn Ser Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Tyr Ser Gly Tyr Thr
                85                  90                  95

Phe Gly Gly Gly Thr Lys Val Glu Ile Lys
            100                 105

<210> SEQ ID NO 111
<211> LENGTH: 106
<212> TYPE: PRT
<213> ORGANISM: Artificial Sequence
<220> FEATURE:
<223> OTHER INFORMATION: Synthetic

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Lys Gly Ser Gln Asn Ile Tyr Lys Ser
            20                  25                  30

Leu Ala Trp Phe Gln Leu Lys Pro Gly Lys Val Pro Lys Leu Leu Ile
        35                  40                  45

Tyr Asp Ala Asn Ser Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Tyr Ser Gly Tyr Thr
                85                  90                  95

Phe Gly Gly Gly Thr Lys Val Glu Ile Lys
            100                 105

<210> SEQ ID NO 112
<211> LENGTH: 106
<212> TYPE: PRT
<213> ORGANISM: Artificial Sequence
<220> FEATURE:
<223> OTHER INFORMATION: Synthetic

<400> SEQUENCE: 112

Asp Ile Gln Met Thr Gln Ser Pro Ser Ser Leu Ser Ala Ser Val Gly
1               5                   10                  15

Asp Arg Val Thr Ile Asn Cys Lys Gly Ser Gln Asn Ile Tyr Lys Ser
            20                  25                  30

Leu Ala Trp Phe Gln Gln Lys Pro Gly Lys Val Pro Lys Leu Leu Ile
        35                  40                  45

Tyr Asp Ala Asn Ser Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Tyr Ser Gly Tyr Thr
                85                  90                  95

Phe Gly Gly Gly Thr Lys Val Glu Ile Lys
            100                 105
```

<210> SEQ ID NO 113
<211> LENGTH: 107
<212> TYPE: PRT
<213> ORGANISM: Artificial Sequence
<220> FEATURE:
<223> OTHER INFORMATION: Synthetic

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Pro
                85                  90                  95

Leu Phe Gly Gly Gly Thr Lys Val Glu Ile Lys
            100                 105

<210> SEQ ID NO 114
<211> LENGTH: 118
<212> TYPE: PRT
<213> ORGANISM: Artificial Sequence
<220> FEATURE:
<223> OTHER INFORMATION: Synthetic

<400> SEQUENCE: 114

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Asn
            20                  25                  30

Gly Val Ser Trp Val Arg Gln Pro Pro Gly Lys Gly Leu Glu Trp Ile
        35                  40                  45

Ala Ala Ile Ser Ser Gly Gly Thr Thr Tyr Tyr Asn Ser Ala Phe Lys
    50                  55                  60

Ser Arg Leu Ser Ile Ser Arg Asn Thr Ser Lys Ser Gln Val Leu Leu
65                  70                  75                  80

Lys Met Asn Ser Leu Gln Thr Glu Asp Thr Ala Met Tyr Phe Cys Ala
                85                  90                  95

Arg Arg Tyr Gly Tyr Gly Trp Tyr Phe Asp Phe Trp Gly Pro Gly Thr
            100                 105                 110

Met Val Thr Val Ser Ser
        115

<210> SEQ ID NO 115
<211> LENGTH: 118
<212> TYPE: PRT
<213> ORGANISM: Artificial Sequence
<220> FEATURE:
<223> OTHER INFORMATION: Synthetic

<400> SEQUENCE: 115

Gln Val Thr Leu Lys Glu Ser Gly Pro Val Leu Val Lys Pro Thr Glu
1               5                   10                  15

```
Thr Leu Thr Leu Thr Cys Thr Val Ser Gly Phe Ser Leu Thr Ser Asn
            20                  25                  30

Gly Val Ser Trp Val Arg Gln Pro Gly Lys Ala Leu Glu Trp Ile
        35                  40                  45

Ala Ala Ile Ser Ser Gly Gly Thr Thr Tyr Tyr Asn Ser Ala Phe Lys
50                      55                  60

Ser Arg Leu Thr Ile Ser Arg Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Arg Tyr Gly Tyr Gly Trp Tyr Phe Asp Phe Trp Gly Gln Gly Thr
            100                 105                 110

Leu Val Thr Val Ser Ser
        115

<210> SEQ ID NO 116
<211> LENGTH: 118
<212> TYPE: PRT
<213> ORGANISM: Artificial Sequence
<220> FEATURE:
<223> OTHER INFORMATION: Synthetic

<400> SEQUENCE: 116

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Ser Asn
            20                  25                  30

Gly Val Ser Trp Val Arg Gln Pro Gly Lys Ala Leu Glu Trp Ile
        35                  40                  45

Ala Ala Ile Ser Ser Gly Gly Thr Thr Tyr Tyr Asn Ser Ala Phe Lys
50                      55                  60

Ser Arg Leu Ser Ile Ser Arg Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Arg Tyr Gly Tyr Gly Trp Tyr Phe Asp Phe Trp Gly Gln Gly Thr
            100                 105                 110

Leu Val Thr Val Ser Ser
        115

<210> SEQ ID NO 117
<211> LENGTH: 118
<212> TYPE: PRT
<213> ORGANISM: Artificial Sequence
<220> FEATURE:
<223> OTHER INFORMATION: Synthetic

<400> SEQUENCE: 117

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Ser Ser
            20                  25                  30

Gly Val Ser Trp Val Arg Gln Pro Gly Lys Ala Leu Glu Trp Ile
        35                  40                  45

Ala Ala Ile Ser Ser Gly Gly Thr Thr Tyr Tyr Asn Ser Ala Phe Lys
50                      55                  60

Ser Arg Leu Thr Ile Ser Arg Asp Thr Ser Lys Ser Gln Val Val Leu
65                  70                  75                  80
```

```
Thr Met Thr Asn Met Asp Pro Val Asp Thr Ala Thr Tyr Tyr Cys Ala
                85                  90                  95

Arg Arg Tyr Gly Tyr Gly Trp Tyr Phe Asp Phe Trp Gly Gln Gly Thr
            100                 105                 110

Leu Val Thr Val Ser Ser
            115

<210> SEQ ID NO 118
<211> LENGTH: 118
<212> TYPE: PRT
<213> ORGANISM: Artificial Sequence
<220> FEATURE:
<223> OTHER INFORMATION: Synthetic

<400> SEQUENCE: 118

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Ser Gln
                20                  25                  30

Gly Val Ser Trp Val Arg Gln Pro Pro Gly Lys Ala Leu Glu Trp Ile
            35                  40                  45

Ala Ala Ile Ser Ser Gly Gly Thr Thr Tyr Tyr Asn Ser Ala Phe Lys
        50                  55                  60

Ser Arg Leu Thr Ile Ser Arg Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Arg Tyr Gly Tyr Gly Trp Tyr Phe Asp Phe Trp Gly Gln Gly Thr
            100                 105                 110

Leu Val Thr Val Ser Ser
            115

<210> SEQ ID NO 119
<211> LENGTH: 118
<212> TYPE: PRT
<213> ORGANISM: Artificial Sequence
<220> FEATURE:
<223> OTHER INFORMATION: Synthetic

<400> SEQUENCE: 119

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Ser Asn
                20                  25                  30

Ala Val Ser Trp Val Arg Gln Pro Pro Gly Lys Ala Leu Glu Trp Ile
            35                  40                  45

Ala Ala Ile Ser Ser Gly Gly Thr Thr Tyr Tyr Asn Ser Ala Phe Lys
        50                  55                  60

Ser Arg Leu Thr Ile Ser Arg Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Arg Tyr Gly Tyr Gly Trp Tyr Phe Asp Phe Trp Gly Gln Gly Thr
            100                 105                 110

Leu Val Thr Val Ser Ser
            115
```

```
<210> SEQ ID NO 120
<211> LENGTH: 106
<212> TYPE: PRT
<213> ORGANISM: Artificial Sequence
<220> FEATURE:
<223> OTHER INFORMATION: Synthetic

<400> SEQUENCE: 120
```

Asp Ile Arg Met Thr Gln Ser Pro Ser Leu Ser Ala Ser Val Gly
1               5                   10                  15

Asp Arg Val Thr Leu Asn Cys Lys Ala Ser Gln Asn Ile Tyr Asn Ser
            20                  25                  30

Leu Ala Trp Tyr Gln Gln Lys Leu Gly Glu Gly Pro Lys Val Leu Ile
        35                  40                  45

Pro Asn Ala Asn Ser Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Phe Tyr Ser Gly Tyr Thr
                85                  90                  95

Phe Gly Ala Gly Thr Lys Leu Glu Leu Lys
            100                 105

```
<210> SEQ ID NO 121
<211> LENGTH: 106
<212> TYPE: PRT
<213> ORGANISM: Artificial Sequence
<220> FEATURE:
<223> OTHER INFORMATION: Synthetic

<400> SEQUENCE: 121
```

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Tyr Asn Ser
            20                  25                  30

Leu Ala Trp Tyr Gln Gln Lys Pro Gly Lys Ala Pro Lys Val Leu Ile
        35                  40                  45

Phe Asn Ala Asn Ser Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Tyr Ser Gly Tyr Thr
                85                  90                  95

Phe Gly Gln Gly Thr Lys Leu Glu Ile Lys
            100                 105

```
<210> SEQ ID NO 122
<211> LENGTH: 106
<212> TYPE: PRT
<213> ORGANISM: Artificial Sequence
<220> FEATURE:
<223> OTHER INFORMATION: Synthetic

<400> SEQUENCE: 122
```

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Tyr Asn Ser
            20                  25                  30

Leu Ala Trp Tyr Gln Gln Lys Pro Gly Lys Ala Pro Lys Val Leu Ile
        35                  40                  45

```
Phe Asn Ala Asn Ser Leu Gln Thr Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Tyr Ser Gly Tyr Thr
                 85                  90                  95

Phe Gly Gln Gly Thr Lys Leu Glu Ile Lys
            100                 105

<210> SEQ ID NO 123
<211> LENGTH: 106
<212> TYPE: PRT
<213> ORGANISM: Artificial Sequence
<220> FEATURE:
<223> OTHER INFORMATION: Synthetic

<400> SEQUENCE: 123

Asp Ile Gln Met Thr Gln Ser Pro Ser Ser Leu Ser Ala Ser Val Gly
 1               5                  10                  15

Asp Arg Val Thr Ile Asn Cys Lys Ala Ser Gln Asn Ile Tyr Asn Ser
                 20                  25                  30

Leu Ala Trp Tyr Gln Gln Lys Pro Gly Lys Ala Pro Lys Val Leu Ile
             35                  40                  45

Phe Asn Ala Asn Ser Leu Gln Thr Gly Ile Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Tyr Ser Gly Tyr Thr
                 85                  90                  95

Phe Gly Gln Gly Thr Lys Leu Glu Ile Lys
            100                 105

<210> SEQ ID NO 124
<211> LENGTH: 107
<212> TYPE: PRT
<213> ORGANISM: Artificial Sequence
<220> FEATURE:
<223> OTHER INFORMATION: Synthetic

<400> SEQUENCE: 124

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Arg
                 85                  90                  95

Ser Phe Gly Gln Gly Thr Lys Leu Glu Ile Lys
            100                 105

<210> SEQ ID NO 125
<211> LENGTH: 14
<212> TYPE: PRT
```

<210> SEQ ID NO 125
<211> LENGTH: (not shown)
<212> TYPE: PRT
<213> ORGANISM: Artificial Sequence
<220> FEATURE:
<223> OTHER INFORMATION: Synthetic

<400> SEQUENCE: 125

Trp Val Arg Gln Ala Pro Gly Lys Gly Leu Glu Trp Val Ala
1               5                   10

<210> SEQ ID NO 126
<211> LENGTH: 32
<212> TYPE: PRT
<213> ORGANISM: Artificial Sequence
<220> FEATURE:
<223> OTHER INFORMATION: Synthetic

<400> SEQUENCE: 126

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Thr Arg
            20                  25                  30

<210> SEQ ID NO 127
<211> LENGTH: 11
<212> TYPE: PRT
<213> ORGANISM: Artificial Sequence
<220> FEATURE:
<223> OTHER INFORMATION: Synthetic

<400> SEQUENCE: 127

Trp Gly Gln Gly Thr Met Val Thr Val Ser Ser
1               5                   10

<210> SEQ ID NO 128
<211> LENGTH: 14
<212> TYPE: PRT
<213> ORGANISM: Artificial Sequence
<220> FEATURE:
<223> OTHER INFORMATION: Synthetic

<400> SEQUENCE: 128

Trp Val Arg Gln Ala Pro Gly Lys Arg Leu Glu Trp Val Ala
1               5                   10

<210> SEQ ID NO 129
<211> LENGTH: 15
<212> TYPE: PRT
<213> ORGANISM: Artificial Sequence
<220> FEATURE:
<223> OTHER INFORMATION: Synthetic

<400> SEQUENCE: 129

Trp Tyr Gln Gln Lys Pro Gly Gln Pro Pro Lys Leu Leu Ile Tyr
1               5                   10                  15

<210> SEQ ID NO 130
<211> LENGTH: 32
<212> TYPE: PRT
<213> ORGANISM: Artificial Sequence
<220> FEATURE:
<223> OTHER INFORMATION: Synthetic

<400> SEQUENCE: 130

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 131
<211> LENGTH: 10
<212> TYPE: PRT
<213> ORGANISM: Artificial Sequence
<220> FEATURE:
<223> OTHER INFORMATION: Synthetic

<400> SEQUENCE: 131

Phe Gly Gln Gly Thr Lys Val Glu Ile Lys
1               5                   10

<210> SEQ ID NO 132
<211> LENGTH: 32
<212> TYPE: PRT
<213> ORGANISM: Artificial Sequence
<220> FEATURE:
<223> OTHER INFORMATION: Synthetic

<400> SEQUENCE: 132

Gly Val Pro Asp Arg Phe Thr Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 133
<211> LENGTH: 25
<212> TYPE: PRT
<213> ORGANISM: Artificial Sequence
<220> FEATURE:
<223> OTHER INFORMATION: Synthetic

<400> SEQUENCE: 133

Gln Val Thr Leu Lys Glu Ser Gly Pro Val Leu Val Lys Pro Thr Glu
1               5                   10                  15

Thr Leu Thr Leu Thr Cys Thr Val Ser
            20                  25

<210> SEQ ID NO 134
<211> LENGTH: 14
<212> TYPE: PRT
<213> ORGANISM: Artificial Sequence
<220> FEATURE:
<223> OTHER INFORMATION: Synthetic

<400> SEQUENCE: 134

Trp Val Arg Gln Pro Pro Gly Lys Ala Leu Glu Trp Ile Ala
1               5                   10

<210> SEQ ID NO 135
<211> LENGTH: 32
<212> TYPE: PRT
<213> ORGANISM: Artificial Sequence
<220> FEATURE:
<223> OTHER INFORMATION: Synthetic

<400> SEQUENCE: 135

Arg Leu Thr Ile Ser Arg Asp Thr Ser Lys Ser Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 136
<211> LENGTH: 11
<212> TYPE: PRT

<213> ORGANISM: Artificial Sequence
<220> FEATURE:
<223> OTHER INFORMATION: Synthetic

<400> SEQUENCE: 136

Trp Gly Gln Gly Thr Leu Val Thr Val Ser Ser
1               5                   10

<210> SEQ ID NO 137
<211> LENGTH: 32
<212> TYPE: PRT
<213> ORGANISM: Artificial Sequence
<220> FEATURE:
<223> OTHER INFORMATION: Synthetic

<400> SEQUENCE: 137

Arg Leu Ser Ile Ser Arg Asp Thr Ser Lys Ser Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 138
<211> LENGTH: 32
<212> TYPE: PRT
<213> ORGANISM: Artificial Sequence
<220> FEATURE:
<223> OTHER INFORMATION: Synthetic

<400> SEQUENCE: 138

Arg Leu Thr Ile Ser Arg Asn Thr Ser Lys Ser Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 139
<211> LENGTH: 10
<212> TYPE: PRT
<213> ORGANISM: Artificial Sequence
<220> FEATURE:
<223> OTHER INFORMATION: Synthetic

<400> SEQUENCE: 139

Gly Phe Ser Leu Thr Ser Ser Gly Val Ser
1               5                   10

<210> SEQ ID NO 140
<211> LENGTH: 10
<212> TYPE: PRT
<213> ORGANISM: Artificial Sequence
<220> FEATURE:
<223> OTHER INFORMATION: Synthetic

<400> SEQUENCE: 140

Gly Phe Ser Leu Thr Ser Gln Gly Val Ser
1               5                   10

<210> SEQ ID NO 141
<211> LENGTH: 10
<212> TYPE: PRT
<213> ORGANISM: Artificial Sequence
<220> FEATURE:
<223> OTHER INFORMATION: Synthetic

<400> SEQUENCE: 141

Gly Phe Ser Leu Thr Ser Asn Ala Val Ser
1               5                   10

<210> SEQ ID NO 142
<211> LENGTH: 23
<212> TYPE: PRT
<213> ORGANISM: Artificial Sequence
<220> FEATURE:
<223> OTHER INFORMATION: Synthetic

<400> SEQUENCE: 142

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 143
<211> LENGTH: 15
<212> TYPE: PRT
<213> ORGANISM: Artificial Sequence
<220> FEATURE:
<223> OTHER INFORMATION: Synthetic

<400> SEQUENCE: 143

Trp Phe Gln Gln Lys Pro Gly Lys Val Pro Lys Leu Leu Ile Tyr
1               5                   10                  15

<210> SEQ ID NO 144
<211> LENGTH: 32
<212> TYPE: PRT
<213> ORGANISM: Artificial Sequence
<220> FEATURE:
<223> OTHER INFORMATION: Synthetic

<400> SEQUENCE: 144

Gly Ile Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 145
<211> LENGTH: 10
<212> TYPE: PRT
<213> ORGANISM: Artificial Sequence
<220> FEATURE:
<223> OTHER INFORMATION: Synthetic

<400> SEQUENCE: 145

Phe Gly Gly Gly Thr Lys Val Glu Ile Lys
1               5                   10

<210> SEQ ID NO 146
<211> LENGTH: 15
<212> TYPE: PRT
<213> ORGANISM: Artificial Sequence
<220> FEATURE:
<223> OTHER INFORMATION: Synthetic

<400> SEQUENCE: 146

Trp Phe Gln Leu Lys Pro Gly Lys Val Pro Lys Leu Leu Ile Tyr
1               5                   10                  15

<210> SEQ ID NO 147
<211> LENGTH: 23
<212> TYPE: PRT
<213> ORGANISM: Artificial Sequence
<220> FEATURE:
<223> OTHER INFORMATION: Synthetic

```
<400> SEQUENCE: 147

Asp Ile Gln Met Thr Gln Ser Pro Ser Ser Leu Ser Ala Ser Val Gly
1               5                   10                  15

Asp Arg Val Thr Ile Asn Cys
            20

<210> SEQ ID NO 148
<211> LENGTH: 15
<212> TYPE: PRT
<213> ORGANISM: Artificial Sequence
<220> FEATURE:
<223> OTHER INFORMATION: Synthetic

<400> SEQUENCE: 148

Trp Tyr Gln Gln Lys Pro Gly Lys Ala Pro Lys Val Leu Ile Phe
1               5                   10                  15

<210> SEQ ID NO 149
<211> LENGTH: 32
<212> TYPE: PRT
<213> ORGANISM: Artificial Sequence
<220> FEATURE:
<223> OTHER INFORMATION: Synthetic

<400> SEQUENCE: 149

Gly Ile Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 150
<211> LENGTH: 10
<212> TYPE: PRT
<213> ORGANISM: Artificial Sequence
<220> FEATURE:
<223> OTHER INFORMATION: Synthetic

<400> SEQUENCE: 150

Phe Gly Gln Gly Thr Lys Leu Glu Ile Lys
1               5                   10

<210> SEQ ID NO 151
<211> LENGTH: 5
<212> TYPE: PRT
<213> ORGANISM: Artificial Sequence
<220> FEATURE:
<223> OTHER INFORMATION: Synthetic

<400> SEQUENCE: 151

Ser Asn Gly Val Ser
1               5

<210> SEQ ID NO 152
<211> LENGTH: 5
<212> TYPE: PRT
<213> ORGANISM: Artificial Sequence
<220> FEATURE:
<223> OTHER INFORMATION: Synthetic

<400> SEQUENCE: 152

Ser Ser Gly Val Ser
1               5

<210> SEQ ID NO 153
```

```
<211> LENGTH: 10
<212> TYPE: PRT
<213> ORGANISM: Artificial Sequence
<220> FEATURE:
<223> OTHER INFORMATION: Synthetic

<400> SEQUENCE: 153

Arg Tyr Gly Tyr Gly Trp Tyr Phe Asp Phe
1               5                   10

<210> SEQ ID NO 154
<211> LENGTH: 32
<212> TYPE: PRT
<213> ORGANISM: Artificial Sequence
<220> FEATURE:
<223> OTHER INFORMATION: Synthetic

<400> SEQUENCE: 154

Gly Val Pro Ser Arg Phe Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 155
<211> LENGTH: 25
<212> TYPE: PRT
<213> ORGANISM: Artificial Sequence
<220> FEATURE:
<223> OTHER INFORMATION: Synthetic

<400> SEQUENCE: 155

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 156
<211> LENGTH: 120
<212> TYPE: PRT
<213> ORGANISM: Artificial Sequence
<220> FEATURE:
<223> OTHER INFORMATION: Synthesized

<400> SEQUENCE: 156

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Ser Trp Val Arg Gln Thr Pro Glu Lys Arg Leu Glu Trp Val
        35                  40                  45

Ala Thr Ile Ser Ser Gly Gly Ser Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Thr Arg Asp Asp Asp Tyr Asp Val Lys Val Phe Ala Tyr Trp Gly Gln
            100                 105                 110

Gly Thr Leu Val Thr Val Ser Ser
        115                 120

<210> SEQ ID NO 157
```

```
<211> LENGTH: 120
<212> TYPE: PRT
<213> ORGANISM: Artificial Sequence
<220> FEATURE:
<223> OTHER INFORMATION: Synthesized

<400> SEQUENCE: 157

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Ser Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Asn Gly Gly Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Ser Ala Met Tyr Tyr Cys
                85                  90                  95

Ala Arg Arg Glu Arg Tyr Asp Glu Asn Gly Phe Ala Tyr Trp Gly Gln
            100                 105                 110

Gly Thr Leu Val Thr Val Ser Ala
        115                 120

<210> SEQ ID NO 158
<211> LENGTH: 120
<212> TYPE: PRT
<213> ORGANISM: Artificial Sequence
<220> FEATURE:
<223> OTHER INFORMATION: Synthesized

<400> SEQUENCE: 158

Gln Val Gln Leu Gln Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Leu Tyr Tyr Gly Tyr Arg Tyr Tyr Phe Asp Tyr Trp Gly Gln
            100                 105                 110

Gly Thr Met Val Thr Val Ser Ser
        115                 120

<210> SEQ ID NO 159
<211> LENGTH: 120
<212> TYPE: PRT
<213> ORGANISM: Artificial Sequence
<220> FEATURE:
<223> OTHER INFORMATION: Synthesized

<400> SEQUENCE: 159

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Met Tyr Tyr Cys
                85                  90                  95

Ala Arg Gly Asp Leu Gly Glu Leu Ser His Phe Asp Tyr Trp Gly Gln
            100                 105                 110

Gly Thr Leu Val Thr Val Ser Ser
            115                 120

<210> SEQ ID NO 160
<211> LENGTH: 113
<212> TYPE: PRT
<213> ORGANISM: Artificial Sequence
<220> FEATURE:
<223> OTHER INFORMATION: Synthesized

<400> SEQUENCE: 160

Asp Ile Val Met Thr Gln Ser Pro Ser Ser Leu Ala Val Ser Leu Gly
 1               5                  10                  15

Glu Arg Val Thr Ile Asn Cys Lys Ser Ser Arg Ser Leu Leu Asn Ser
            20                  25                  30

Arg Ile Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Lys Gln
                85                  90                  95

Ser Tyr Asn Leu Leu Thr Phe Gly Gln Gly Thr Lys Val Glu Ile Lys
            100                 105                 110

Arg

<210> SEQ ID NO 161
<211> LENGTH: 113
<212> TYPE: PRT
<213> ORGANISM: Artificial Sequence
<220> FEATURE:
<223> OTHER INFORMATION: Synthesized

<400> SEQUENCE: 161

Asp Ile Val Met Ser Gln Ser Pro Ser Ser Leu Ala Val Ser Ala Gly
 1               5                  10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80
```

-continued

Ile Ser Ser Val Gln Ala Glu Asp Leu Ala Val Tyr Tyr Cys Lys Gln
            85                  90                  95

Ser Tyr Asn Leu Tyr Thr Phe Gly Gly Gly Thr Lys Leu Glu Ile Lys
        100                 105                 110

Arg

<210> SEQ ID NO 162
<211> LENGTH: 114
<212> TYPE: PRT
<213> ORGANISM: Artificial Sequence
<220> FEATURE:
<223> OTHER INFORMATION: Synthesized

<400> SEQUENCE: 162

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ala Ile Tyr Arg
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
            85                  90                  95

Tyr Ser Arg Ile Pro Leu Thr Phe Gly Gly Gly Thr Lys Val Glu Ile
        100                 105                 110

Lys Arg

<210> SEQ ID NO 163
<211> LENGTH: 112
<212> TYPE: PRT
<213> ORGANISM: Artificial Sequence
<220> FEATURE:
<223> OTHER INFORMATION: Synthesized

<400> SEQUENCE: 163

Asp Ile Val Met Thr Gln Ser Pro Asp Ser Leu Pro Val Ser Leu Gly
1               5                   10                  15

Glu Arg Ala Thr Ile Asn Cys Lys Ser Ser Leu Thr Val Leu Ser Thr
            20                  25                  30

Ala Asn His Lys Asn His Leu Ala Trp Tyr Gln Gln Lys Pro Gly Gln
        35                  40                  45

Pro Pro Lys Leu Leu Ile Tyr Trp Ala Ser Leu Arg Ala Ser Gly Val
    50                  55                  60

Pro Asp Arg Phe Thr Gly Ser Gly Ser Gly Thr Asp Phe Thr Leu Thr
65                  70                  75                  80

Ile Ser Ala Leu Gln Ala Glu Asp Val Ala Val Tyr Tyr Cys Gln Gln
            85                  90                  95

Phe Tyr Ser Thr Pro Thr Phe Gly Gln Gly Thr Arg Leu Glu Ile Lys
        100                 105                 110

<210> SEQ ID NO 164
<211> LENGTH: 57
<212> TYPE: DNA
<213> ORGANISM: Artificial Sequence
<220> FEATURE:
<223> OTHER INFORMATION: Synthesized

<400> SEQUENCE: 164
atggagttcg gcctgtcctg gctgttcctg gtggccatcc tgaagggcgt gcagtgc    57

<210> SEQ ID NO 165
<211> LENGTH: 19
<212> TYPE: PRT
<213> ORGANISM: Artificial Sequence
<220> FEATURE:
<223> OTHER INFORMATION: Synthesized

<400> SEQUENCE: 165

Met Glu Phe Gly Leu Ser Trp Leu Phe Leu Val Ala Ile Leu Lys Gly
1               5                   10                  15

Val Gln Cys

<210> SEQ ID NO 166
<211> LENGTH: 57
<212> TYPE: DNA
<213> ORGANISM: Artificial Sequence
<220> FEATURE:
<223> OTHER INFORMATION: Synthesized

<400> SEQUENCE: 166
atggactgga cctggagcat cctttctctg gtggcagcag caacaggtgc ccactcc    57

<210> SEQ ID NO 167
<211> LENGTH: 19
<212> TYPE: PRT
<213> ORGANISM: Artificial Sequence
<220> FEATURE:
<223> OTHER INFORMATION: Synthesized

<400> SEQUENCE: 167

Met Asp Trp Thr Trp Ser Ile Leu Phe Leu Val Ala Ala Ala Thr Gly
1               5                   10                  15

Ala His Ser

<210> SEQ ID NO 168
<211> LENGTH: 66
<212> TYPE: DNA
<213> ORGANISM: Artificial Sequence
<220> FEATURE:
<223> OTHER INFORMATION: Synthesized

<400> SEQUENCE: 168
atggacatgc gcgtgcccgc ccagctgctg ggcctgctga tgctgtgggt gtccggctcc    60
tccggc    66

<210> SEQ ID NO 169
<211> LENGTH: 22
<212> TYPE: PRT
<213> ORGANISM: Artificial Sequence
<220> FEATURE:
<223> OTHER INFORMATION: Synthesized

<400> SEQUENCE: 169

Met Asp Met Arg Val Pro Ala Gln Leu Leu Gly Leu Leu Met Leu Trp
1               5                   10                  15

Val Ser Gly Ser Ser Gly
            20

<210> SEQ ID NO 170

```
<211> LENGTH: 107
<212> TYPE: PRT
<213> ORGANISM: Artificial Sequence
<220> FEATURE:
<223> OTHER INFORMATION: Synthesized

<400> SEQUENCE: 170

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 171
<211> LENGTH: 106
<212> TYPE: PRT
<213> ORGANISM: Artificial Sequence
<220> FEATURE:
<223> OTHER INFORMATION: Synthesized

<400> SEQUENCE: 171

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 172
<211> LENGTH: 330
<212> TYPE: PRT
<213> ORGANISM: Artificial Sequence
<220> FEATURE:
<223> OTHER INFORMATION: Synthesized

<400> SEQUENCE: 172

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Val Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 173
<211> LENGTH: 330
<212> TYPE: PRT
<213> ORGANISM: Artificial Sequence
<220> FEATURE:
<223> OTHER INFORMATION: Synthesized

<400> SEQUENCE: 173

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 174
<211> LENGTH: 330
<212> TYPE: PRT
<213> ORGANISM: Artificial Sequence
<220> FEATURE:
<223> OTHER INFORMATION: Synthesized

<400> SEQUENCE: 174

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

```
Pro Ala Pro Glu Ala Ala Gly Gly Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 175
<211> LENGTH: 219
<212> TYPE: PRT
<213> ORGANISM: Artificial Sequence
<220> FEATURE:
<223> OTHER INFORMATION: Synthesized

<400> SEQUENCE: 175

Asp Ile Val Met Thr Gln Ser Pro Ser Ser Leu Ala Val Ser Leu Gly
1               5                   10                  15
Glu Arg Val Thr Ile Asn Cys Lys Ser Ser Arg Ser Leu Leu Asn Ser
            20                  25                  30
Arg Ile Arg Lys Asn Tyr Leu Ala Trp Tyr Gln Gln Lys Pro Gly Gln
        35                  40                  45
Ser Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Lys Gln
                85                  90                  95
Ser Tyr Asn Leu Leu Thr Phe Gly Gln Gly Thr Lys Val Glu Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
```

```
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215
```

<210> SEQ ID NO 176
<211> LENGTH: 450
<212> TYPE: PRT
<213> ORGANISM: Artificial Sequence
<220> FEATURE:
<223> OTHER INFORMATION: Synthesized

<400> SEQUENCE: 176

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Ser Trp Val Arg Gln Thr Pro Glu Lys Arg Leu Glu Trp Val
        35                  40                  45

Ala Thr Ile Ser Ser Gly Gly Ser Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Thr Arg Asp Asp Asp Tyr Asp Val Lys Val Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

Asn Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 177
<211> LENGTH: 450
<212> TYPE: PRT
<213> ORGANISM: Artificial Sequence
<220> FEATURE:
<223> OTHER INFORMATION: Synthesized

<400> SEQUENCE: 177

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ile Met Ser Trp Val Arg Gln Thr Pro Glu Lys Arg Leu Glu Trp Val
            35                  40                  45

Ala Thr Ile Ser Ser Gly Gly Ser Ser Thr Tyr Tyr Pro Asp Ser Val
50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Thr Arg Asp Asp Asp Tyr Asp Val Lys Val Phe Ala Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

```
Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 178
<211> LENGTH: 116
<212> TYPE: PRT
<213> ORGANISM: Artificial Sequence
<220> FEATURE:
<223> OTHER INFORMATION: Synthetic Peptide

<400> SEQUENCE: 178

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Ser Ser
            20                  25                  30

Gly Val Ser Trp Val Arg Gln Pro Pro Gly Lys Ala Leu Glu Trp Ile
        35                  40                  45

Ala Ala Ile Ser Ser Gly Gly Ser Thr Tyr Tyr Asn Ser Ala Phe Lys
    50                  55                  60

Ser Arg Leu Thr Ile Ser Arg Asp Thr Ser Lys Ser Gln Val Val Leu
65                  70                  75                  80

Thr Met Thr Asn Met Asp Pro Val Asp Thr Ala Thr Tyr Tyr Cys Ala
            85                  90                  95
```

```
Arg His Arg Pro Phe Tyr Phe Asp Tyr Trp Gly Gln Gly Thr Leu Val
            100             105                 110

Thr Val Ser Ser
        115

<210> SEQ ID NO 179
<211> LENGTH: 116
<212> TYPE: PRT
<213> ORGANISM: Artificial Sequence
<220> FEATURE:
<223> OTHER INFORMATION: Synthetic Peptide

<400> SEQUENCE: 179

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Ser Gln
            20                  25                  30

Gly Val Ser Trp Val Arg Gln Pro Pro Gly Lys Ala Leu Glu Trp Ile
            35                  40                  45

Ala Ala Ile Ser Ser Gly Gly Ser Thr Tyr Tyr Asn Ser Ala Phe Lys
        50                  55                  60

Ser Arg Leu Thr Ile Ser Arg Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg His Arg Pro Phe Tyr Phe Asp Tyr Trp Gly Gln Gly Thr Leu Val
            100             105                 110

Thr Val Ser Ser
        115
```